US009056111B1

(12) United States Patent
Larson et al.

(10) Patent No.: US 9,056,111 B1
(45) Date of Patent: Jun. 16, 2015

(54) SELECTIVE EFFLUX INHIBITORS AND RELATED PHARMACEUTICAL COMPOSITIONS AND METHODS OF TREATMENT

(71) Applicants: STC.UNM, Albuquerque, NM (US); UNIVERSITY OF KANSAS, Lawrence, KS (US)

(72) Inventors: Richard Smith Larson, Albuquerque, NM (US); Larry A. Sklar, Albuquerque, NM (US); Bruce S. Edwards, Albuquerque, NM (US); Juan Jacob Strouse, Albuquerque, NM (US); Irena Ivnitski-Steele, Coral Springs, FL (US); Hadya M. Khawaja, Albuquerque, NM (US); Jerec Warren Ricci, Albuquerque, NM (US); Jeffrey Aube, Lawrence, KS (US); Jennifer Elizabeth Golden, Olathe, KS (US); Tuanli Yao, Lawrence, KS (US); Warren S. Weiner, Lawrence, KS (US); Chad E. Schroeder, Lawrence, KS (US)

(73) Assignees: STC.UNM, Albuquerque, NM (US); UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 13/622,651

(22) Filed: Sep. 19, 2012

Related U.S. Application Data

(60) Provisional application No. 61/537,199, filed on Sep. 21, 2011, provisional application No. 61/680,899, filed on Aug. 8, 2012.

(51) Int. Cl.
| | | |
|---|---|---|
| *A01N 43/90* | (2006.01) | |
| *A61K 31/519* | (2006.01) | |
| *C07D 487/00* | (2006.01) | |
| *A61K 31/437* | (2006.01) | |
| *C07D 487/04* | (2006.01) | |

(52) U.S. Cl.
CPC ............. *A61K 31/519* (2013.01); *A61K 31/437* (2013.01); *C07D 487/04* (2013.01)

(58) Field of Classification Search
None
See application file for complete search history.

(56) References Cited

U.S. PATENT DOCUMENTS 8,642,660 B2 * 2/2014 Goldfarb ............ 514/641

FOREIGN PATENT DOCUMENTS

JP  03-204877  * 9/1991 ........... C07D 487/04

OTHER PUBLICATIONS http://pubchem.ncbi.nlm.nih.gov/summary/summary.cgi?sid=88095709, last accessed Feb. 20, 2014.*
http://pubchem.ncbi.nlm.nih.gov/summary/summary.cgi?sid=85752814, last accessed Feb. 20, 2014.*
http://pubchem.ncbi.nlm.nih.gov/summary/summary.cgi?sid=97301789, last accessed Feb. 20, 2014.*
Goldman B: Multidrug resistance: can new drugs help chemotherapy score against cancer? Journal of the National Cancer Institute 2003;95:255-7.
Krishna R, Mayer LD: Multidrug resistance (MDR) in cancer. Mechanisms, reversal using modulators of MDR and the role of MDR modulators in influencing the pharmacokinetics of anticancer drugs. European Journal of Pharmaceutical Sciences 2000;11:265-283.
Mistry P, Plumb J, Eccles S, Watson S, Dale I, Ryder H, Box G, Charlton P, Templeton D, Bevan PB: In vivo efficacy of XR9051, a potent modulator of P-glycoprotein mediated multidrug resistance. British Journal of Cancer 1999;79:1672-1678.
Szakacs G, Varadi A, Ozvegy-Laczka C, Sarkadi B: The role of ABC transporters in drug absorption, distribution, metabolism, excretion and toxicity (ADME-Tox). Drug Discovery Today 2008;13:379-393.
O'Connor R: The pharmacology of cancer resistance. Anticancer Research 2007;27:1267-1272.
Gillet J-P, Efferth T, Remacle J: Chemotherapy-induced resistance by ATP-binding cassette transporter genes. Biochimica et Biophysica Acta 2007;1775:237-262.
Sarkadi B, Homolya L, Szakacs G, Varadi A: Human multidrug resistance ABCB and ABCG transporters: participation in a chemoimmunity defense system. Physiological Reviews 2006;86:1179-1236.
Robey RW, Polgar O, Deeken J, To KW, Bates SE: ABCG2: determining its relevance in clinical drug resistance. Cancer Metastasis Rev. 2007;26:39-57.
Garimella TS, Ross DD, Eiseman JL, Mondick JT, Joseph E, Nakanishi T, Bates SE, Bauer KS: Plasma pharmacokinetics and tissue distribution of the breast cancer resistance protein (BCRP/ABCG2) inhibitor fumitremorgin C in SCID mice bearing T8 tumors. Cancer Chemotherapy and Pharmacology 2005;55:101-109.
Robey RW, Medina-Perez WY, Nishiyama K, Lahusen T, Miyake K, Litman T, Senderowicz AM, Ross DD, Bates SE: Overexpression of the ATP-binding cassette half-transporter, ABCG2 (MXR/BCRP/ABCP1), in flavopiridol-resistant human breast cancer cells. Clinical Cancer Research 2001;7:145-152.
Allen JD, Van Loevezijn A, Lakhai JM, Van der Valk M, Van Tellingen O, Reid G, Schellens JHM, Koomen G-J, Schinkel AH: Potent and specific inhibition of the breast cancer resistance protein multidrug transporter in vitro and in mouse intestine by a novel analogue of fumitremorgin C. Molecular Cancer Therapeutics 2002;1:417-425.

(Continued)

*Primary Examiner* — Jeffrey H Murray
(74) *Attorney, Agent, or Firm* — Henry D. Coleman; R. Neil Sudol

(57) ABSTRACT

The present invention provides pyrazolo[1,5-a]pyrimidine compounds which inhibit cancer-associated transporter proteins, methods of treating or preventing the onset of a cancer-associated transporter protein-mediated disease by administering such compounds, and pharmaceutical compositions comprising such compounds. In one embodiment, the invention provides pyrazolo[1,5-a]pyrimidine efflux inhibitors that are selective toward ABCG2 over ABCB1. Compounds and compositions according to the present invention may be used to treat cancer, including drug resistant (DR) and multiple drug resistant (MDR) cancers.

16 Claims, 28 Drawing Sheets

(56) References Cited

OTHER PUBLICATIONS

Thiessen B, Stewart C, Tsao M, Kamel-Reid S, Schaiquevich P, Mason W, Easaw J, Belanger K, Forsyth P, McIntosh L and others: A phase I/II trial of GW572016 (lapatinib) in recurrent glioblastoma multiforme: clinical outcomes, pharmacokinetics and molecular correlation. Cancer Chemother. Pharmacol. 2010;65:353-361.

Eckford PDW, Sharom FJ: ABC Efflux Pump-Based Resistance to Chemotherapy Drugs. Chemical Reviews 2009;109:2989-3011.

Kawase M, Motohashi N: New multidrug resistance reversal agents. Current Drug Targets 2003;4:31-43.

Broccatelli F, Carosati E, Neri A, Frosini M, Goracci L, Oprea TI, Cruciani G: A Novel Approach for Predicting P-Glycoprotein (ABCB1) Inhibition Using Molecular Interaction Fields. J. Med. Chem. 2011;54:1740-1751.

Tsuruo T, Iida H, Tsukagoshi S, Sakurai Y: Overcoming of vincristine resistance in P388 leukemia in vivo and in vitro through enhanced cytotoxicity of vincristine and vinblastine by verapamil. Cancer Research 1981;41:1967-72.

Yung BYM, Chang FJ, Bor AMS: Modulation of the reversibility of actinomycin D cytotoxicity in HeLa cells by verapamil. Cancer Letters 1991;60:221-7.

Foxwell BMJ, Mackie A, Ling V, Ryffel B: Identification of the multidrug resistance-related P-glycoprotein as a cyclosporine binding protein. Mol. Pharmacol. FIELD Full Journal Title:Molecular Pharmacology 1989;36:543-6.

Twentyman PR, Fox NE, White DJG: Cyclosporin A and its analogs as modifiers of adriamycin and vincristine resistance in a multi-drug resistant human lung cancer cell line. British Journal of Cancer 1987;56:55-7.

Naito M, Yusa K, Tsuruo T: Steroid hormones inhibit binding of Vinca alkaloid to multidrug resistance related P-glycoprotein. Biochemical and Biophysical Research Communications 1989;158:1066-71.

Yang CPH, DePinho SG, Greenberger LM, Arceci RJ, Horwitz SB: Progesterone interacts with P-glycoprotein in multidrug-resistant cells and in the endometrium of gravid uterus. Journal of Biological Chemistry 1989;264:782-8.

Hu Y-P, Chapey C, Robert J: Relationship between the inhibition of azidopine binding to P-glycoprotein by MDR modulators and their efficiency in restoring doxorubicin intracellular accumulation. Cancer Letters 1996;109:203-209.

Wang Ej, Casciano CN, Clement RP, Johnson WW: Two transport binding sites of P-glycoprotein are unequal yet contingent: initial rate kinetic analysis by ATP hydrolysis demonstrates intersite dependence. Biochimica et Biophysica Acta, Protein Structure and Molecular Enzymology 2000;1481:63-74.

Atadja P, Watanabe T, Xu H, Cohen D: PSC-833, a frontier in modulation of P-glycoprotein mediated multidrug resistance. Cancer and Metastasis Reviews 1998;17:163-168.

Seiden MV, Swenerton KD, Matulonis U, Campos S, Rose P, Batist G, Ette E, Garg V, Fuller A, Harding MW and others: A Phase II study of the MDR inhibitor bricodar (INCEL, VX-710) and paclitaxel in women with advanced ovarian cancer Refractory to Paclitaxel Therapy. Gynecologic Oncology 2002;86:302-310.

Toppmeyer D, Seidman AD, Pollak M, Russell C, Tkaczuk K, Verma S, Overmoyer B, Garg V, Ette E, Harding MW and others: Safety and efficacy of the multidrug resistance inhibitor incel (biricodar; VX-710) in combination with paclitaxel for advanced breast cancer refractory to paclitaxel. Clinical Cancer Research 2002;8:670-678.

Germann UA, Shlyakhter D, Mason VS, Zelle RE, Duffy JP, Galullo V, Armistead DM, Saunders JO, Boger J, Harding MW: Cellular and biochemical characterization of VX-710 as a chemosensitizer: reversal of P-glycoprotein-mediated multidrug resistance in vitro. Anti-Cancer Drugs 1997;8:125-140.

Dale IL, Tuffley W, Callaghan R, Holmes JA, Martin K, Luscombe M, Mistry P, Ryder H, Stewart AJ, Charlton P and others: Reversal of P-glycoprotein-mediated multidrug resistance by XR9051, a novel diketopiperazine derivative. British Journal of Cancer 1998;78:885-892.

Stewart A, Steiner J, Mellows G, Laguda B, Norris D, Bevan P: Phase I trial of XR9576 in healthy volunteers demonstrates modulation of P-glycoprotein in CD56+ lymphocytes after oral and intravenous administration. Clinical Cancer Research 2000;6:4186-4191.

Agrawal M, Abraham J, Balis FM, Edgerly M, Stein WD, Bates S, Fojo T, Chen CC: Increased 99mTc-sestamibi accumulation in normal liver and drug-resistant tumors after the administration of the glycoprotein inhibitor, XR9576. Clinical Cancer Research 2003;9:650-656.

Mistry P, Stewart AJ, Dangerfield W, Okiji S, Liddle C, Bootle D, Plumb JA, Templeton D, Charlton P: In vitro and in vivo reversal of P-glycoprotein-mediated multidrug resistance by a novel potent modulator, XR9576. Cancer Research 2001;61:749-758.

Roe M, Folkes A, Ashworth P, Brumwell J, Chima L, Hunjan S, Pretswell I, Dangerfield W, Ryder H, Charlton P: Reversal of P-glycoprotein mediated multidrug resistance by novel anthranilamide derivatives. Bioorganic & Medicinal Chemistry Letters 1999;9:595-600.

Jekerle V, Klinkhammer W, Reilly RM, Piquette-Miller M, Wiese M: Novel tetrahydroisoquinolin-ethyl-phenylamine based multidrug resistance inhibitors with broad-spectrum modulating properties. Cancer Chemotherapy and Pharmacology 2007;59:61-69.

Jekerle V, Klinkhammer W, Scollard DA, Breitbach K, Reilly RM, Piquette-Miller M, Wiese M: In vitro and in vivo evaluation of WK-X-34, a novel inhibitor of P-glycoprotein and BCRP, using radio imaging techniques. International Journal of Cancer 2006;119:414-422.

Hyafil F, Vergely C, Du Vignaud P, Grand-Perret T: In vitro and in vivo reversal of multidrug resistance by GF120918, an acridonecarboxamide derivative. Cancer Research 1993;53:4595-602.

Starling JJ, Shepard RL, Cao J, Law KL, Norman BH, Kroin JS, Ehlhardt WJ, Baughman TM, Winter MA, Bell MG and others: Pharmacological characterization of LY335979: a potent cyclopropyldibenzosuberane modulator of P-glycoprotein. Advances in Enzyme Regulation 1997;37:335-47.

Gerrard G, Payne E, Baker RJ, Jones DT, Potter M, Prentice HG, Ethell M, McCullough H, Burgess M, Mehta AB and others: Clinical effects and P-glycoprotein inhibition in patients with acute myeloid leukemia treated with zosuquidar trihydrochloride, daunorubicin and cytarabine. Haematologica 2004;89:782-790.

Sorbera LA, Castaner J, Silvestre JS, Bayes M: Zosuquidar trihydrochloride: multidrug resistance modulator P-glycoprotein (MDR-1) inhibitor. Drugs of the Future 2003;28:125-136.

Naito M, Matsuba Y, Sato S, Hirata H, Tsuruo T: MS-209, a quinoline-type reversal agent, potentiates antitumor efficacy of docetaxel in multidrug-resistant solid tumor xenograft models. Clinical Cancer Research 2002;8:582-8.

Saeki T, Nomizu T, Toi M, Ito Y, Noguchi S, Kobayashi T, Asaga T, Minami H, Yamamoto N, Aogi K and others: Dofequidar fumarate (MS-209) in combination with cyclophosphamide, doxorubicin, and fluorouracil for patients with advanced or recurrent breast cancer. Journal of Clinical Oncology 2007;25:411-417.

van Zuylen L, Sparreboom A, van der Gaast A, Nooter K, Eskens FALM, Brouwer E, Bol CJ, de Vries R, Palmer PA, Verweij J: Disposition of docetaxel in the presence of P-glycoprotein inhibition by intravenous administration of R101933. European Journal of Cancer 2002;38:1090-1099.

Van Zuylen L, Sparreboom A, Van der Gaast A, Van der Burg MEL, Van Beurden V, Bol CJ, Woestenborghs R, Palmer PA, Verweij J: The orally administered P-glycoprotein inhibitor R101933 does not alter the plasma pharmacokinetics of docetaxel. Clinical Cancer Research 2000;6:1365-1371.

Guns ES, Denyssevych T, Dixon R, Bally MB, Mayer L: Drug interaction studies between paclitaxel (Taxol) and OC144-093—a new modulator of MDR in cancer chemotherapy. European Journal of Drug Metabolism and Pharmacokinetics 2002;27:119-126.

Newman MJ, Rodarte JC, Benbatoul KD, Romano SJ, Zhang C, Krane S, Moran EJ, Uyeda RT, Dixon R, Guns ES and others: Discovery and characterization of OC144-093, a novel inhibitor of P-glycoprotein-mediated multidrug resistance. Cancer Research 2000;60:2964-2972.

(56) References Cited

OTHER PUBLICATIONS

Sarshar S, Zhang C, Moran EJ, Krane S, Rodarte JC, Benbatoul KD, Dixon R, Mjalli AMM: 2,4,5-Trisubstituted imidazoles novel non-toxic modulators of P-glycoprotein mediated multidrug resistance. Part 1. Bioorganic & Medicinal Chemistry Letters 2000;10:2599-2601.
Zhang C, Sarshar S, Moran EJ, Krane S, Rodarte JC, Benbatoul KD, Dixon R, Mjalli AMM: 2,4,5-Trisubstituted imidazoles novel non-toxic modulators of P-glycoprotein mediated multidrug resistance. Part 2. Bioorganic & Medicinal Chemistry Letters 2000;10:2603-2605.
Vezmar M, Georges E: Reversal of MRP-mediated doxorubicin resistance with quinoline-based drugs. Biochemical Pharmacology 2000;59:1245-1252.
Gollapudi S, Kim CH, Tran BN, Sangha S, Gupta S: Probenecid reverses multidrug resistance in multidrug resistance-associated protein-overexpressing HL60/AR and H69/AR cells but not in P-glycoprotein-overexpressing HL60/Tax and P388/ADR cells. Cancer Chemotherapy and Pharmacology 1997;40:150-158.
Stein U, Lage H, Jordan A, Walther W, Bates SE, Litman T, Hohenberger P, Dietel M: Impact of BCRP/MXR, MRP1 and MDR1/P-glycoprotein on thermoresistant variants of atypical and classical multidrug resistant cancer cells. International Journal of Cancer 2002;97:751-760.
Rabindran SK, Ross DD, Doyle LA, Yang W, Greenberger LM: Fumitremorgin C reverses multidrug resistance in cells transfected with the breast cancer resistance protein. Cancer Research 2000;60:47-50.
Rabindran SK, He H, Singh M, Brown E, Collins KI, Annable T, Greenberger LM: Reversal of a novel multidrug resistance mechanism in human colon carcinoma cells by fumitremorgin C. Cancer Research 1998;58:5850-5858.
Liu J, Cui G, Zhao M, Cui C, Ju J, Peng S: Dual-acting agents that possess reversing resistance and anticancer activities: Design, synthesis, MES-SA/Dx5 cell assay, and SAR of Benzyl 1,2,3,5,11,11a-hexahydro-3,3-dimethyl-1-oxo-6H-imidazo[3',4':1,2]pyridin[3,4-b]indol-2-substituted acetates. Bioorganic & Medicinal Chemistry 2007;15:7773-7788.
Burkhart CA, Watt F, Murray J, Pajic M, Prokvolit A, Xue C, Flemming C, Smith J, Purmal A, Isachenko N and others: Small-Molecule Multidrug Resistance-Associated Protein 1 Inhibitor Reversan Increases the Therapeutic Index of Chemotherapy in Mouse Models of Neuroblastoma. Cancer Research 2009;69:6573-6580.
Abe T, Koike K, Ohga T, Kubo T, Wada M, Kohno K, Mori T, Hidaka K, Kuwano M: Chemosensitisation of spontaneous multidrug resistance by a 1,4-dihydropyridine analogue and verapamil in human glioma cell lines overexpressing MRP or MDR1. British Journal of Cancer 1995;72:418-23.
Ivnitski-Steele I, Larson RS, Lovato DM, Khawaja HM, Winter SS, Oprea TI, Sklar LA, Edwards BS: High-throughput flow cytometry to detect selective inhibitors of ABCB1, ABCC1, and ABCG2 transporters. Assay Drug Dev Technol 2008;6:263-276.
Xia CQ, Milton MN, Gan L-S: Evaluation of drug-transporter interactions using in vitro and in vivo models. Current Drug Metabolism 2007;8:341-363.
Sharom FJ: The P-glycoprotein efflux pump: how does it transport drugs? Journal of Membrane Biology 1997;160:161-175.
Vellenga E, Tuyt L, Wierenga B-J, Muller M, Dokter W: Interleukin-6 production by activated human monocytic cells is enhanced by MK-571, a specific inhibitor of the multi-drug resistance protein-1. British Journal of Pharmacology 1999;127:441-448.
Estes DA, Lovato DM, Khawaja HM, Winter SS, Larson RS: Genetic alterations determine chemotherapy resistance in childhood T-ALL: modelling in stage-specific cell lines and correlation with diagnostic patient samples. British Journal of Haematology 2007;139:20-30.
Winter SS, Jiang Z, Khawaja HM, Griffin T, Devidas M, Asselin BL, Larson RS: Identification of genomic classifiers that distinguish induction failure in T-lineage acute lymphoblastic leukemia: a report from the Children's Oncology Group. Blood 2007;110:1429-1438.

Kuckuck FW, Edwards BS, Sklar LA: High throughput flow cytometry. Cytometry 2001;44:83-90.
Ramirez S, Aiken Charity T, Andrzejewski B, Sklar Larry A, Edwards Bruce S: High-throughput flow cytometry: validation in microvolume bioassays. Cytometry 2003;53:55-65.
Data obtained from Luceome Biotechnologies using the KinaseSeeker™ assay. For information on the assay principle and method prt, Jester BW, Cox KJ, Gaj A, Shomin CD, Porter JR, Ghosh I: A Coiled-Coil Enabled Split-Luciferase Three-Hybrid System: Applied Toward Profiling Inhibitors of Protein Kinases. J. Am. Chem. Soc. 2010;132:11727-11735.
Mayur YC, Peters GJ, Prasad VVSR, Lemos C, Sathish NK: Design of new drug molecules to be used in reversing multidrug resistance in cancer cells. Current Cancer Drug Targets 2009;9:298-306.
Seelig A, Gatlik-Landwojtowicz E: Inhibitors of multidrug efflux transporters: their membrane and protein interactions. Mini-Reviews in Medicinal Chemistry 2005;5:135-151.
Shapiro AB, Ling V: Positively cooperative sites for drug transport by P-glycoprotein with distinct drug specificities. European Journal of Biochemistry 1997;250:130-137.
Lugo MR, Sharom FJ: Interaction of LDS-751 and Rhodamine 123 with P-Glycoprotein: Evidence for Simultaneous Binding of Both Drugs. Biochemistry 2005;44:14020-14029.
Malkhandi J, Ferry DR, Boer R, Gekeler V, Ise W, Kerr DJ: Dexniguldipine-HCl is a potent allosteric inhibitor of [3H] vinblastine binding to P-glycoprotein of CCRF ADR 5000 cells. European Journal of Pharmacology, Molecular Pharmacology Section 1994;288:105-14.
Allen JD, Jackson SC, Schinkel AH: A mutation hot spot in the Bcrp1 (Abcg2) multidrug transporter in mouse cell lines selected for doxorubicin resistance. Cancer Research 2002;62:2294-2299.
Mitomo H, Kato R, Ito A, Kasamatsu S, Ikegami Y, Kii I, Kudo A, Kobatake E, Sumino Y, Ishikawa T: A functional study on polymorphism of the ATP-binding cassette transporter ABCG2: critical role of arginine-482 in methotrexate transport. Biochemical Journal 2003;373:767-774.
Ozvegy-Laczka C, Koblos G, Sarkadi B, Varadi A: Single amino acid (482) variants of the ABCG2 multidrug transporter: major differences in transport capacity and substrate recognition. Biochimica et Biophysica acta 2005;1668:53-63.
Winter SS, Lovato DM, Khawaja HM, Edwards BS, Steele ID, Young SM, Oprea TI, Sklar LA, Larson RS: High-throughput screening for daunorubicin-mediated drug resistance identifies mometasone furoate as a novel ABCB1-reversal agent. J. Biomol. Screening 2008;13:185-193.
Sarkadi, B., Homolya, L., Szakacs, G., Varadi, A.: Human multidrug resistance ABCB and ABCG transporters: Participation in a chemoimmunity defense system. Physiol Rev 2006;86:1179-1236.
Krishna, R., Mayer, L. D.: Multidrug resistance (MDR) in cancer. Mechanisms, reversal using modulators of MDR and the role of MDR modulators in influencing the pharmacokinetics of anticancer drugs. Eur J Pharm Sci. 2000;11:265-283.
Gillet, J.-P., Efferth, T., Remacle, J.: Chemotherapy-induced resistance by ATP-binding cassette transporter genes. Biochim Biophys Acta 2007;1775:237-262.
Szakacs, G., Varadi, A., Ozvegy-Laczka, C., Sarkadi, B.: The role of ABC transporters in drug absorption, distribution, metabolism, excretion and toxicity (ADME-Tox). Drug Discov Today 2008;13:379-393.
Eckford, P. D. W., Sharom, F. J.: ABC efflux pump-based resistance to chemotherapy drugs. Chem Rev 2009;109:2989-3011.
Atadja, P., Watanabe, T., Xu, H., Cohen, D.: PSC-833, a frontier in modulation of P-glycoprotein mediated multidrug resistance. Cancer Metastasis Rev 1998;17:163-168.
Germann, U. A., Shlyakhter, D., Mason, V. S., Zelle, R. E., Duffy, J. P., Galullo, V., et al.: Cellular and biochemical characterization of VX-710 as a chemosensitizer: Reversal of P-glycoprotein-mediated multidrug resistance in vitro. Anti-Cancer Drugs 1997;8:125-140.
Dale, I. L., Tuffley, W., Callaghan, R., Holmes, J. A., Martin, K., Luscombe, M., et al.: Reversal of P-glycoprotein-mediated multidrug resistance by XR9051, a novel diketopiperazine derivative. Br J Cancer 1998;78:885-892.

(56) References Cited

OTHER PUBLICATIONS

Mistry, P., Stewart, A. J., Dangerfield, W., Okiji, S., Liddle, C., Bootle, D., et al.: In vitro and in vivo reversal of P-glycoprotein-mediated multidrug resistance by a novel potent modulator, XR9576. Cancer Res 2001;61:749-758.

Stewart, A., Steiner, J., Mellows, G., Laguda, B., Norris, D., Bevan, P.: Phase I trial of XR9576 in healthy volunteers demonstrates modulation of P-glycoprotein in CD56+ lymphocytes after oral and intravenous administration. Clin Cancer Res 2000;6:4186-4191.

Jekerle, V., Klinkhammer, W., Scollard, D. A., Breitbach, K., Reilly, R. M., Piquette-Miller, M., et al.: In vitro and in vivo evaluation of WK-X-34, a novel inhibitor of P-glycoprotein and BCRP, using radio imaging techniques. Int J Cancer 2006;119:414-422.

Hyafil, F., Vergely, C., Du Vignaud, P., Grand-Perret, T.: In vitro and in vivo reversal of multidrug resistance by GF120918, an acridonecarboxamide derivative. Cancer Res 1993;53:4595-4602.

Gerrard, G., Payne, E., Baker, R. J., Jones, D. T., Potter, M., Prentice, H. G., et al.: Clinical effects and P-glycoprotein inhibition in patients with acute myeloid leukemia treated with zosuquidar trihydrochloride, daunorubicin and cytarabine. Haematologica 2004;89:782-790.

Saeki, T., Nomizu, T., Toi, M., Ito, Y., Noguchi, S., Kobayashi, T., et al.: Dofequidar fumarate (MS-209) in combination with cyclophosphamide, doxorubicin, and fluorouracil for patients with advanced or recurrent breast cancer. J Clin Oncol 2007;25:411-417.

van Zuylen, L., Sparreboom, A., van der Gaast, A., Nooter, K., Eskens, F. A. L. M., Brouwer, E., et al.: Disposition of docetaxel in the presence of P-glycoprotein inhibition by intravenous administration of R101933. Eur J Cancer 2002;38:1090-1099.

Guns, E. S., Denyssevych, T., Dixon, R., Bally, M. B., Mayer, L.: Drug interaction studies between paclitaxel (Taxol) and OC144-093—A new modulator of MDR in cancer chemotherapy. Eur J Drug Metab Pharmacokinet 2002;27:119-126.

Allen, J. D., Van Loevezijn, A., Lakhai, J. M., Van der Valk, M., Van Tellingen, O., Reid, G., et al.: Potent and specific inhibition of the breast cancer resistance protein multidrug transporter in vitro and in mouse intestine by a novel analogue of fumitremorgin C. Mol Cancer Ther 2002;1:417-425.

Rabindran, S. K., Ross, D. D., Doyle, L. A., Yang, W., Greenberger, L. M.: Fumitremorgin C reverses multidrug resistance in cells transfected with the breast cancer resistance protein. Cancer Res 2000;60:47-50.

Abe, T., Koike, K., Ohga, T., Kubo, T., Wada, M., Kohno, K., et al.: Chemosensitisation of spontaneous multidrug resistance by a 1,4-dihydropyridine analogue and verapamil in human glioma cell lines overexpressing MRP or MDR1. Br J Cancer 1995;72:418-423.

Robey, R. W., Polgar, O., Deeken, J., To, K. W., Bates, S. E.: ABCG2: Determining its relevance in clinical drug resistance. Cancer Metastasis Rev 2007;26:39-57.

Garimella, T. S., Ross, D. D., Eiseman, J. L., Mondick, J. T., Joseph, E., Nakanishi, T., et al.: Plasma pharmacokinetics and tissue distribution of the breast cancer resistance protein (BCRP/ABCG2) inhibitor fumitremorgin C in SCID mice bearing T8 tumors. Cancer Chemother Pharmacol 2005;55:101-109.

Robey, R. W., Medina-Perez, W. Y., Nishiyama, K., Lahusen, T., Miyake, K., Litman, T., et al.: Overexpression of the ATP-binding cassette half-transporter, ABCG2 (MXR/BCRP/ABCP1), in flavopiridol-resistant human breast cancer cells. Clin Cancer Res 2001;7:145-152.

Thiessen, B., Stewart, C., Tsao, M., Kamel-Reid, S., Schaiquevich, P., Mason, W., et al.: A phase I/II trial of GW572016 (lapatinib) in recurrent glioblastoma multiforme: Clinical outcomes, pharmacokinetics and molecular correlation. Cancer Chemother Pharmacol 2010;65:353-361.

Mistry, P., Plumb, J., Eccles, S., Watson, S., Dale, I., Ryder, H., et al.: In vivo efficacy of XR9051, a potent modulator of P-glycoprotein mediated multidrug resistance. Br J Cancer 1999;79:1672-1678.

Vellenga, E., Tuyt, L., Wierenga, B.-J., Muller, M., Dokter, W.: Interleukin-6 production by activated human monocytic cells is enhanced by MK-571, a specific inhibitor of the multi-drug resistance protein-1. Br J Pharmacol 1999;127:441-448.

Burkhart, C. A., Watt, F., Murray, J., Pajic, M., Prokvolit, A., Xue, C., et al.: Small-molecule multidrug resistance-associated protein 1 inhibitor reversan increases the therapeutic index of chemotherapy in mouse models of neuroblastoma. Cancer Res 2009;69:6573-6580.

Estes, D. A., Lovato, D. M., Khawaja, H. M., Winter, S. S., Larson, R. S.: Genetic alterations determine chemotherapy resistance in childhood T-ALL: modelling in stage-specific cell lines and correlation with diagnostic patient samples. Br J Haematol 2007;139:20-30.

Kuckuck, F. W., Edwards, B. S., Sklar, L. A.: High throughput flow cytometry. Cytometry 2001;44:83-90.

Ramirez, S., Aiken Charity, T., Andrzejewski, B., Sklar Larry, A., Edwards Bruce, S.: High-throughput flow cytometry: validation in microvolume bioassays. Cytometry 2003;53:55-65.

Ivnitski-Steele, I., Larson, R. S., Lovato, D. M., Khawaja, H. M., Winter, S. S., Oprea, T. I., et al.: High-throughput flow cytometry to detect selective inhibitors of ABCB1, ABCC1, and ABCG2 transporters. Assay Drug Dev Technol 2008;6:263-276.

Winter, S. S., Lovato, D. M., Khawaja, H. M., Edwards, B. S., Steele, I. D., Young, S. M., et al.: High-throughput screening for daunorubicin-mediated drug resistance identifies mometasone furoate as a novel ABCB1-reversal agent. J Biomol Screen 2008;13:185-193.

\* cited by examiner

Reagents: (a) methyl 3-(furan-2-yl)-3-oxopropanoate, AcOH, 100 °C, 2 h; (b) POCl₃, BnEt₃NCl, PhNMe₂, CH₃CN, 80 °C, 16 h; (c) furan-3-yl(piperazin-1-yl)methanone, DIPEA, CH₃CN, 100 °C, 16 h; (d) diethylmalonate, 21% NaOEt, EtOH, 80 °C, 3h, 75%; (e) POCl₃, N,N-dimethylaniline, 115 °C, 16 h, 42%; (f) potassium aryltrifluoroborate salt, Pd(OAc)₂, RuPhos, Na₂CO₃, EtOH, MW, 90 °C, 6 h.

SID 85240370

ABC B1 $EC_{50}$ = 6.18 μM
ABC G2 $EC_{50}$ = 0.96 μM (6.4x)
ABC B1 $CR_{50}$ = 0.70 μM
ABC G2 $CR_{50}$ = 0.14 μM

Figure 4. Validated hit resulting from preliminary commercial SAR effort

Figure 5. Focus of SAR expansion efforts based on primary efflux data.

Commercial hit

SID 85240370

ABC B1 $EC_{50}$ = 6.18 μM
ABC G2 $EC_{50}$ = 0.96 μM (6.4x)

Synthesized Analogue

SID 88095709

ABC B1 $EC_{50}$ = 4.65 μM
ABC G2 $EC_{50}$ = 0.13 μM (36x)

ABC B1 EC$_{50}$ = 9.40 µM
ABC G2 EC$_{50}$ = 2.30 µM (4.1x)

SID 97301790

Commercial hit — SID 85240370
Synthesized Analogue — SID 88095709
Synthesized Analogue — SID 97301789

|  | ABC B1 | ABC G2 | B1: G2 Fold | ABC B1 | ABC G2 | B1: G2 Fold | ABC B1 | ABC G2 | B1: G2 Fold |
|---|---|---|---|---|---|---|---|---|---|
| EC$_{50}$ | 6.18 µM | 0.96 µM | 6.4 x | 4.65 µM | 0.13 µM | 36 x | 50.00 µM | 0.21 µM | 233 x |
| CR$_{50}$ | 0.25 µM | 0.14 µM | 1.8x | 0.55 µM | 0.31 µM | 1.8x | 0.02 µM | 0.09 µM | 0.22 x |
| TD$_{50}$ | 6.77 µM | 6.00 µM |  | 5.52 µM | 18.31 µM |  | > 100 µM | > 100 µM |  |
| TD$_{50}$/CR$_{50}$ | toxic | toxic |  | toxic | 59 |  | 5495 | 1176 |  |

FIGURE 11
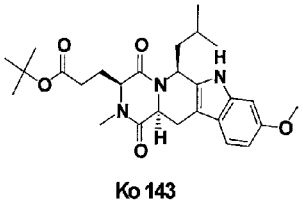
|        | ABCB1    | ABCG2   |
|--------|----------|---------|
| EC50   | 0.6 μM   | 2.3 μM  |
| CR50   | 0.01 μM  | 0.7 μM  |
| TD50   | 2.0 μM   | 21.4 μM |
|        | ABCB1   | ABCG2    |
|--------|---------|----------|
| EC50   | 4.4 μM  | 0.8 μM   |
| CR50   | 2.2 μM  | 3.6 μM   |
| TD50   | 7.0 μM  | >100 μM  |
|        | ABCB1    | ABCG2    |
|--------|----------|----------|
| EC50   | >50 μM   | >50 μM   |
| CR50   | 20.4 μM  | 57.4 μM  |
| TD50   | 20.4 μM  | 57.4 μM  |
XR 9051     Reversan     MK 571
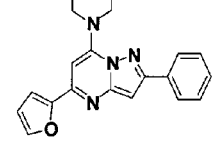
Ko 143     SID 88095709     SID 85752814     SID 97301789
|        | ABCB1    | ABCG2   |
|--------|----------|---------|
| EC50   | >50 μM   | 13.6 μM |
| CR50   | 1.0 μM   | 5.9 μM  |
| TD50   | 2.8 μM   | 20 μM   |
|        | ABCB1   | ABCG2   |
|--------|---------|---------|
| EC50   | 4.7 μM  | 0.1 μM  |
| CR50   | 0.6 μM  | 0.3 μM  |
| TD50   | 5.5 μM  | 18 μM   |
|        | ABCB1    | ABCG2    |
|--------|----------|----------|
| EC50   | 6.5 μM   | 2.5 μM   |
| CR50   | 1.2 μM   | 0.4 μM   |
| TD50   | >100 μM  | >100 μM  |
|        | ABCB1    | ABCG2    |
|--------|----------|----------|
| EC50   | >50 μM   | 0.2 μM   |
| CR50   | 0.02 μM  | 0.09 μM  |
| TD50   | >100 μM  | >100 μM  |

Structure & Activities:

| Compound SID | Efflux Inhibition ||| Chemoreversal ||
|---|---|---|---|---|---|
| | Target ABCG2 $EC_{50}$ | Anti-target ABCB1 $EC_{50}$ | Fold Selective | ABCG2 Mitoxantrone Potentiation | ABCB1 Daunorubicin Potentiation |
| 88095709 | 130 nM | 4.65 µM | ~ 36 | $CR_{50}$ = 310 nM $TD_{50}$ = 18.3 µM | $CR_{50}$ = 550 nM $TD_{50}$ = 5.52 µM |
| 85752814 | 2.54 µM | 6.49 µM | ~ 3 | $CR_{50}$ = 410 nM $TD_{50}$ = >100 µM | $CR_{50}$ = 1.18 µM $TD_{50}$ = >100 µM |
| 97301789 | 210 nM | >50 µM | > 238 | $CR_{50}$ = 20 nM $TD_{50}$ = >100 µM | $CR_{50}$ = 90 nM $TD_{50}$ = >100 µM |

Table 1. SAR expansion on initial hit SID 85240370.

* S = synthesized; P = purchased    a = % Response

FIGURE 15

Table 2. Continuation of SAR expansion on initial hit SID 85240370.

| Entry | SID/CID | Internal Center Number | * | R1 | R2 | R3 | R4 | Potency (uM) mean (n = # replicates) ABC B1 $IC_{50}$ uM (% Res)$^a$ | n | ABC G2 $IC_{50}$ uM (% Res)$^a$ | n | Selectivity B1:G2 | Potentiation Assays ABC B1 $CR_{50}$ (uM) | $TD_{50}$ (uM) | $TD_{50}/CR_{50}$ | ABC G2 $CR_{50}$ (uM) | $TD_{50}$ (uM) | $TD_{50}/CR_{50}$ |
|---|---|---|---|---|---|---|---|---|---|---|---|---|---|---|---|---|---|---|
| 1 | CID44623844 / SID87550709 | KUC104228N | S | 4-Br-Ph | phenyl | H | CO-3-furan | 1.31 (1.7) | 2 | 0.75 (93) | 2 | 1.7 | not tested | not tested | | not tested | not tested | |
| 2 | CID44640183 / SID88095704 | KUC104486N | S | 2-MeO-Ph | phenyl | H | CO-3-furan | 2.17 (130) | 2 | 0.45 (107) | 2 | 4.8 | 0.45 | 4.57 | toxic | 0.49 | 6.50 | toxic |
| 3 | CID44623840 / SID87550708 | KUC104227N | S | 3-MeO-Ph | phenyl | H | CO-3-furan | 2.26 (136) | 4 | 1.14 (118) | 5 | 2.0 | not tested | not tested | | not tested | not tested | |
| 4 | CID44807592 / SID87357359 | KUC104140N | S | 4-MeO-Ph | phenyl | H | CO-3-furan | 1.44 (170) | 5 | 1.16 (94) | 5 | 1.2 | 0.23 | 5.54 | toxic | 0.38 | >100 | 263 |
| 5 | CID44640176 / SID88095711 | KUC104493N | S | 2-MeO-Ph | phenyl | H | CO-2-furan | 3.00 (121) | 2 | 1.03 (101) | 2 | 2.9 | not tested | not tested | | not tested | not tested | |
| 6 | CID44968166 / SID90944695 | KUC104560N | S | 3-MeO-Ph | phenyl | H | CO-2-furan | 4.77 (135) | 2 | 1.40 (113) | 2 | 3.4 | not tested | not tested | | not tested | not tested | |
| 7 | CID492424 / SID85240373 | UNM-0000306232 | P | 4-Cl-Ph | phenyl | H | CO-2-furan | 3.63 (80) | 2 | 1.37 (67) | 2 | 2.6 | not tested | not tested | | not tested | not tested | |
| 8 | CID45105079 / SID92123922 | KUC105312N | S | 3-Me-Ph | phenyl | H | CO-2-furan | 3.88 (102) | 3 | 2.46 (46) | 3 | 1.0 | not tested | not tested | | not tested | not tested | |
| 9 | CID44640179 / SID88095712 | KUC104494N | S | 2-MeO-Ph | phenyl | H | CO-phenyl | 2.31 (158) | 2 | 0.76 (11) | 2 | 2.9 | not tested | not tested | | not tested | not tested | |
| 10 | CID44968164 / SID90944697 | KUC104562N | S | 3-F-Ph | phenyl | H | CO-phenyl | 4.34 (130) | 2 | 2.27 (123) | 2 | 1.9 | not tested | not tested | | not tested | not tested | |
| 11 | CID44968158 / SID90944698 | KUC104563N | S | 4-F-Ph | phenyl | H | CO-phenyl | 3.99 (124) | 2 | 2.03 (111) | 2 | 2.0 | not tested | not tested | | not tested | not tested | |
| 12 | CID44640177 / SID88095708 | KUC104491N | S | phenyl | 2-furan | H | CO-3-furan | 4.65 (112) | 5 | 0.13 (99) | 4 | 35.8 | 0.55 | 5.52 | toxic | 0.31 | 18.30 | 59 |
| 13 | CID46905002 / SID99361146 | KUC106875N | S | phenyl | 2-MeO-Ph | H | CO-3-furan | 4.52 (116) | 1 | 3.65 (99) | 2 | 1.2 | 0.17 | 3.73 | toxic | 0.68 | 7.62 | toxic |
| 14 | CID46905009 / SID99361144 | KUC106873N | S | phenyl | 4-MeO-Ph | H | CO-3-furan | 4.55 (127) | 1 | 2.37 (84) | 2 | 1.9 | not tested | not tested | | not tested | not tested | |
| 15 | CID46904993 / SID99361147 | KUC106876N | S | phenyl | 2-F-Ph | H | CO-3-furan | 5.61 (133) | 1 | 0.56 (95) | 1 | 10.0 | not tested | not tested | | not tested | not tested | |
| 16 | CID46905008 / SID99361145 | KUC106874N | S | phenyl | 3-F-Ph | H | CO-3-furan | 7.07 (145) | 1 | 1.69 (112) | 2 | 4.2 | not tested | not tested | | not tested | not tested | |
| 17 | CID46904994 / SID99361149 | KUC106878N | S | phenyl | 4-F-Ph | H | CO-3-furan | 11.62 (102) | 1 | 6.45 (109) | 2 | 1.8 | not tested | not tested | | not tested | not tested | |
| 18 | CID46905006 / SID99361157 | KUC106886N | S | phenyl | tBut | H | CO-3-furan | 5.62 (94) | 1 | 25.90 (104) | 2 | 0.2 | not tested | not tested | | not tested | not tested | |

* S = synthesized; P = purchased
$^a$ = % Response

FIGURE 16

Table 3. Summary of modifications for R1.

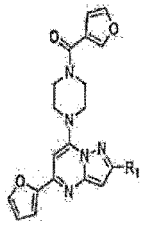

| Entry | SID/CID | Internal Center Number | * | R1 | Efflux Assay Potency (uM) mean (n = # replicates) ABC B1 | | | | Selectivity B1:G2 Efflux | Potentiation Assays ABC B1 | | | ABC G2 | | |
|---|---|---|---|---|---|---|---|---|---|---|---|---|---|---|---|
| | | | | | n | IC₅₀ uM (% Res)ᵃ | n | IC₅₀ uM (% Res)ᵃ | | CR₅₀ (uM) | TD₅₀ (uM) | TD₅₀/CR₅₀ | CR₅₀ (uM) | TD₅₀ (uM) | TD₅₀/CR₅₀ |
| 1 | SID88095709 CID44640177 | KUC104491N | S | phenyl | 5 | 4.65 (112) | 4 | 0.13 (98) | 35.8 | 0.55 | 5.52 | toxic | 0.31 | 18.30 | 59 |
| 2 | SID99376135 CID46912088 | KUC106905N | S | t-butyl | 1 | 3.31 (89) | 1 | 1.97 (102) | 1.7 | not tested | not tested | | not tested | not tested | |
| 3 | SID99361154 CID46905003 | KUC106883N | S | 2-thiophene | 1 | 8.42 (107) | 2 | 1.56 (100) | 5.4 | not tested | not tested | | not tested | not tested | |
| 4 | SID99361155 CID46905000 | KUC106884N | S | 2-furan | 2 | 1.70 (84) | 2 | 2.35 (99) | 0.7 | 0.19 | 1.93 | toxic | 1.21 | >100 | 83 |
| 5 | SID92123918 CID45105077 | KUC105308N | S | 3-Cl-phenyl | 4 | 6.42 (112) | 5 | 2.55 (84) | 2.5 | 0.53 | 8.53 | toxic | 1.38 | 10.80 | toxic |
| 6 | SID99361153 CID46904995 | KUC106882N | S | 4-Cl-phenyl | 1 | 41.54 (79) | 2 | 1.89 (101) | 22.0 | not tested | not tested | | not tested | not tested | |
| 7 | SID99361150 CID46905004 | KUC106879N | S | 2-MeO-phenyl | 1 | 5.57 (124) | 2 | 2.76 (104) | 2.0 | not tested | not tested | | not tested | not tested | |
| 8 | SID92764890 CID45281176 | KUC105432N | S | 3-MeO-phenyl | 4 | 7.40 (89) | 5 | 2.26 (78) | 3.3 | 0.47 | 5.52 | toxic | 1.00 | >100 | 100 |
| 9 | SID93619266 CID45489721 | KUC105733N | S | 4-MeO-phenyl | 4 | 3.45 (51) | 4 | 0.89 (68) | 3.9 | 5.77 | >100 | 17 | 0.76 | >100 | 131 |
| 10 | SID99361151 CID46905007 | KUC106880N | S | 3-Me-phenyl | 1 | 3.45 (123) | 1 | 0.58 (103) | 6.0 | not tested | not tested | | not tested | not tested | |
| 11 | SID99361152 CID46904998 | KUC106881N | S | 4-Me-phenyl | 1 | 11.27 (109) | 1 | 5.19 (102) | 2.2 | not tested | not tested | | not tested | not tested | |
| 12 | SID88095710 CID44640180 | KUC104492N | S | 3-(2-furyl)-phenyl | 4 | 3.97975 (100) | 5 | 0.93 (82) | 4.3 | not tested | not tested | | not tested | not tested | |

* S = synthesized; P = purchased
ᵃ = % Response

Table 4. Summary of modifications for R2.

FIGURE 18

Table 5. Summary of modifications for R4.

| Entry | SID/CID | Internal Center Number | * | R4 | Efflux Assay Potency (uM) mean (n = # replicates) | | | | Selectivity B1:G2 Efflux | Potentiation Assays | | | | | |
|---|---|---|---|---|---|---|---|---|---|---|---|---|---|---|---|
| | | | | | ABC B1 | | ABC G2 | | | ABC B1 | | | ABC G2 | | |
| | | | | | n | IC₅₀ uM (% Res)ᵃ | n | IC₅₀ uM (% Res) | | CR₅ (uM) | TD₅₀ (uM) | TD₅₀/ CR₅ | CR₅ (uM) | TD₅₀ (uM) | TD₅₀/ CR₅ |
| 1 | SID88095709 / CID44640177 | KUC104491N | S | CO-3-furan | 5 | 4.65 (112) | 4 | 0.13 (98) | 35.8 | 0.55 | 5.52 | toxic | 0.31 | 18.30 | 59 |
| 2 | SID96022056 / CID46173049 | KUC105787N | S | CO-2-furan | 4 | 6.57 (68) | 4 | 2.77 (71) | 2.4 | not tested | not tested | | not tested | not tested | |
| 3 | SID96022058 / CID46173055 | KUC105789N | S | CO-3-thiophene | 4 | 4.93 (58) | 4 | 1.38 (48) | 3.6 | not tested | not tested | | not tested | not tested | |
| 4 | SID96022057 / CID46173043 | KUC105788N | S | CO-phenyl | 3 | 5.56 (61) | 4 | 1.62 (62) | 3.4 | not tested | not tested | | not tested | not tested | |
| 5 | SID96022050 / CID46173050 | KUC105781N | S | CO-3-(2-Me-furan) | 3 | 11.9 (58) | 3 | 2.33 (65) | 5.1 | not tested | not tested | | not tested | not tested | |
| 6 | SID96022052 / CID46173047 | KUC105783N | S | CO-3-(2,4-diMe-furan) | 3 | 7.32 (54) | 3 | 3.68 (63) | 2.0 | not tested | not tested | | not tested | not tested | |
| 7 | SID96022053 / CID46173046 | KUC105784N | S | CO-3-(2,5-diMe-furan) | 4 | 12 (74) | 4 | 3.37 (65) | 3.6 | not tested | not tested | | not tested | not tested | |
| 8 | SID96022054 / CID46173052 | KUC105785N | S | CO-3-benzofuran | 2 | 8.83 (78) | 4 | 2.84 (42) | 3.1 | not tested | not tested | | not tested | not tested | |
| 9 | SID96022055 / CID46173053 | KUC105786N | S | COCH₃ | 2 | 3.63 (71) | 3 | 0.52 (52) | 6.9 | 0.19 | 10.10 | toxic | 0.93 | >100 | 108 |
| 10 | SID93619269 / CID45489722 | KUC105736N | S | CH₂-phenyl | 4 | 8.99 (84) | 4 | 3.07 (66) | 2.9 | not tested | not tested | | not tested | not tested | |
| 11 | SID93619263 / CID45489719 | KUC105730N | S | CO₂-benzyl | 2 | 50 (NA) | 4 | 2.71 (59) | 18.5 | not tested | not tested | | not tested | not tested | |

* S = synthesized; P = purchased
ᵃ = % Response

FIGURE 19

Table 6. Summary of piperazine and combined R4 modifications (X)

| Entry | SID/CID | Internal Center Number | * | X | Efflux Assay Potency (uM) mean (n = # replicates) | | | | Selectivity B1:G2 Efflux | Potentiation Assays | | | | | |
|---|---|---|---|---|---|---|---|---|---|---|---|---|---|---|---|
| | | | | | ABC B1 | | ABC G2 | | | ABC B1 | | | ABC G2 | | |
| | | | | | n | IC₅₀ uM (% Res)ᵃ | n | IC₅₀ uM (% Res)ᵃ | | CR₅₀ (uM) | TD₅₀ (uM) | TD₅₀/CR₅₀ | CR₅₀ (uM) | TD₅₀ (uM) | TD₅₀/CR₅₀ |
| 1 | SID88095709 / CID44640177 | KUC104491N | S | 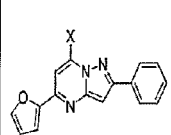 | 5 | 4.65 (112) | 4 | 0.13 (98) | 35.8 | 0.55 | 5.52 | toxic | 0.31 | 18.30 | 59 |
| 2 | SID93619270 / CID45489714 | KUC105737N | S | 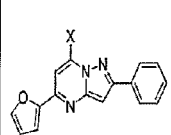 | 2 | 23.56 (66) | 2 | 5.71 (58) | 4.1 | not tested | not tested | | not tested | not tested | |
| 3 | SID93619259 / CID45489720 | KUC105726N | S | 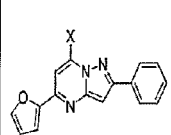 | 3 | 50.00 | 2 | 8.88 (52) | 5.6 | not tested | not tested | | not tested | not tested | |
| 4 | SID93619262 / CID45489718 | KUC105729N | S | 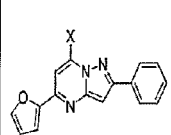 | 2 | 11.92 (80) | 3 | 25.47 (81) | 0.5 | not tested | not tested | | not tested | not tested | |
| 5 | SID93619261 / CID45489715 | KUC105728N | S | 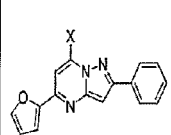 | 3 | 17.54 (65) | 3 | 13.05 (82) | 1.3 | not tested | not tested | | not tested | not tested | |
| 6 | SID96022048 / CID46173045 | KUC105779N | S | 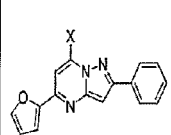 | 2 | 13.06 (69) | 4 | 5.43 (63) | 2.4 | not tested | not tested | | not tested | not tested | |
| 7 | SID93619264 / CID45489712 | KUC105731N | S | 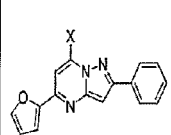 | 2 | 27.67 (84) | 2 | 7.68 (83) | 3.6 | not tested | not tested | | not tested | not tested | |
| 8 | SID93619268 / CID45489716 | KUC105735N | S | 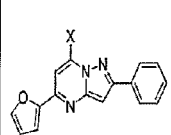 | 4 | 4.06 (68) | 4 | 1.64 (66) | 2.5 | not tested | not tested | | not tested | not tested | |
| 9 | SID96022049 / CID46173044 | KUC105780N | S | 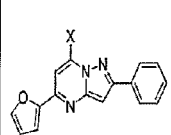 | 4 | 50.00 | 2 | 8.03 (24) | 6.2 | not tested | not tested | | not tested | not tested | |
| 10 | SID96022051 / CID46173054 | KUC105782N | S | 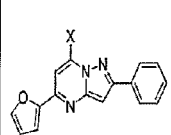 | 4 | 19.14 (76) | 4 | 2.26 (66) | 8.5 | not tested | not tested | | not tested | not tested | |
| 11 | SID97301786 / CID46245506 | KUC105882N | S | 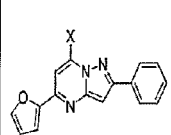 | 3 | 3.27 (87) | 4 | 4.65 (48) | 0.7 | not tested | not tested | | not tested | not tested | |

* S = synthesized; P = purchased
ᵃ = % Response

FIGURE 20

Table 7. Analogues with R1 – R4 substitution patterns in combination.

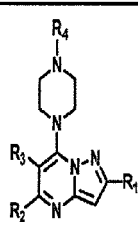

| Entry | SID/CID | Internal Center Number | * | R1 | R2 | R3 | R4 | Efflux Assay Potency (uM) mean (n = # replicates) ABC B1 | | ABC G2 | | Selectivity B1:G2 Efflux | Potentiation Assays ABC B1 | | | ABC G2 | | |
|---|---|---|---|---|---|---|---|---|---|---|---|---|---|---|---|---|---|---|
| | | | | | | | | n | IC₅₀ uM (% Res) | n | IC₅₀ uM (% Res) | | CR₅₀ (uM) | TD₅₀ (uM) | TD₅₀/CR₅₀ | CR₅₀ (uM) | TD₅₀ (uM) | TD₅₀/CR₅₀ |
| 1 | SID88095709 / CID44640177 | KUC104491N | S | phenyl | 2-furyl | H | CO-3-furan | 5 | 4.65 (112) | 4 | 0.13 (98) | 35.8 | 0.55 | 5.52 | toxic | 0.31 | 18.30 | 59 |
| 2 | SID99376136 / CID46912089 | KUC106906N | S | 3-Cl-phenyl | 2-furyl | H | COCH₃ | 1 | 0.80 (113) | 2 | 0.56 (127) | 1.4 | 0.08 | 17.60 | 232 | 0.58 | >100 | 174 |
| 3 | SID99376137 / CID46912090 | KUC106907N | S | 3-MeO-phenyl | 2-furyl | H | COCH₃ | 1 | 1.64 (66) | 2 | 1.9 (121) | 0.9 | 0.32 | 49.30 | 155 | 1.18 | >100 | 85 |
| 4 | SID99376134 / CID46912091 | KUC106904N | S | 4-Me-phenyl | 2-furyl | H | CH₂-3-furan | 1 | 8.7 (114) | 2 | 2.67 (64) | 3.3 | 0.35 | 12.50 | toxic | 1.68 | 57.90 | 34 |
| 5 | SID87557810 / CID44629743 | KUC104249N | S | phenyl | methyl | methyl | CO-3-furan | 5 | 1.63 (33) | 5 | 2.18 (94) | 0.7 | not tested | not tested | | not tested | not tested | |
| 6 | SID97301789 / CID46245505 | KUC105885N | S | 3-MeO-phenyl | methyl | methyl | CH₂-3-furan | 3 | 50.00 | 4 | 0.21 (82) | 233.2 | 0.02 | >100 | 5495 | 0.09 | >100 | 1176 |

* S = synthesized; P = purchased
a = % Response

FIGURE 21

Table 8. Percent of activity remaining for various kinases when inhibited by SID 88095709.

| Entry | Kinase | Family | %Activity Remaining | Entry | Kinase | Family | %Activity Remaining |
|---|---|---|---|---|---|---|---|
| 1 | AKT1(Full Length) | AGC | 84.4 | 26 | MLK3 | TKL | 100.0 |
| 2 | AMPK-a1 | CAMK | 100.0 | 27 | MST2 | STE | 100.0 |
| 3 | AURKA | Other | 91.7 | 28 | p38-g | CMGC | 100.0 |
| 4 | AURKB | Other | 100.0 | 29 | PAK1 | STE | 100.0 |
| 5 | BLK | TK | 100.0 | 30 | PDGFRB | TK | 100.0 |
| 6 | CAMK1 | CAMK | 85.7 | 31 | PDK1 | AGC | 100.0 |
| 7 | CAMK1G | CAMK | 97.4 | 32 | PIM1 | CAMK | 100.0 |
| 8 | CAMK2B | CAMK | 100.0 | 33 | PIM2 | CAMK | 75.5 |
| 9 | CAMKK1 | Other | 100.0 | 34 | PKA | AGC | 100.0 |
| 10 | CHEK1 | CAMK | 100.0 | 35 | PKC-e | AGC | 100.0 |
| 11 | CLK1 | CMGC | 100.0 | 36 | PKG1 | AGC | 100.0 |
| 12 | CLK2 | CMGC | 96.3 | 37 | PLK4 | Other | 99.2 |
| 13 | DDR2 | TK | 100.0 | 38 | PRKD3 | CAMK | 100.0 |
| 14 | FLT1 | TK | 87.9 | 39 | PTK2 | TK | 100.0 |
| 15 | FLT2 | TK | 100.0 | 40 | PTK2B | TK | 100.0 |
| 16 | FLT3 | TK | 99.6 | 41 | RPS6KA1 | AGC | 100.0 |
| 17 | FYN | TK | 100.0 | 42 | RPS6KA4 | AGC | 100.0 |
| 18 | GSK3-a | CMGC | 100.0 | 43 | SIK1 | CAMK | 94.9 |
| 19 | IGFR1 | TK | 100.0 | 44 | SIK2 | CAMK | 99.5 |
| 20 | IKK-e | Other | 100.0 | 45 | SLK | STE | 100.0 |
| 21 | ITK | TK | 100.0 | 46 | SNARK | CAMK | 100.0 |
| 22 | LYN | TK | 93.9 | 47 | SYK | TK | 100.0 |
| 23 | MARK1 | CAMK | 100.0 | 48 | TNK2 | TK | 100.0 |
| 24 | MET | TK | 100.0 | 49 | VEGFR2 | TK | 100.0 |
| 25 | MLK1 | TKL | 84.2 | 50 | YSK1 | STE | 100.0 |

HRMS data for SID 88095709; HRMS m/z calculated for $C_{25}H_{22}N_5O_3$ [M$^+$ + H] 440.1717, found 440.1715

(Example 2)

FIGURE 26
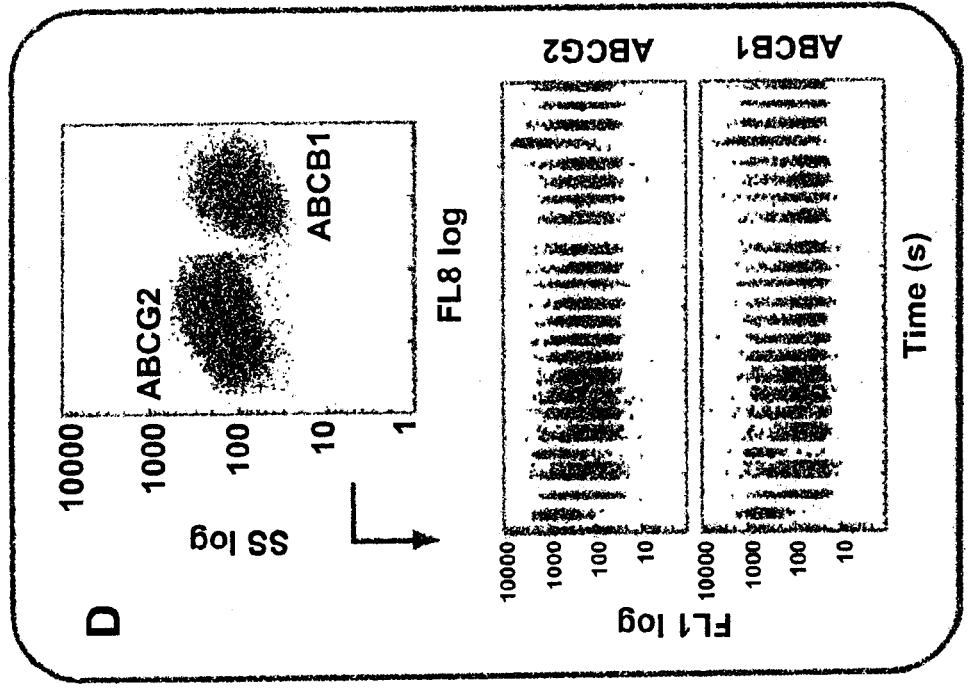
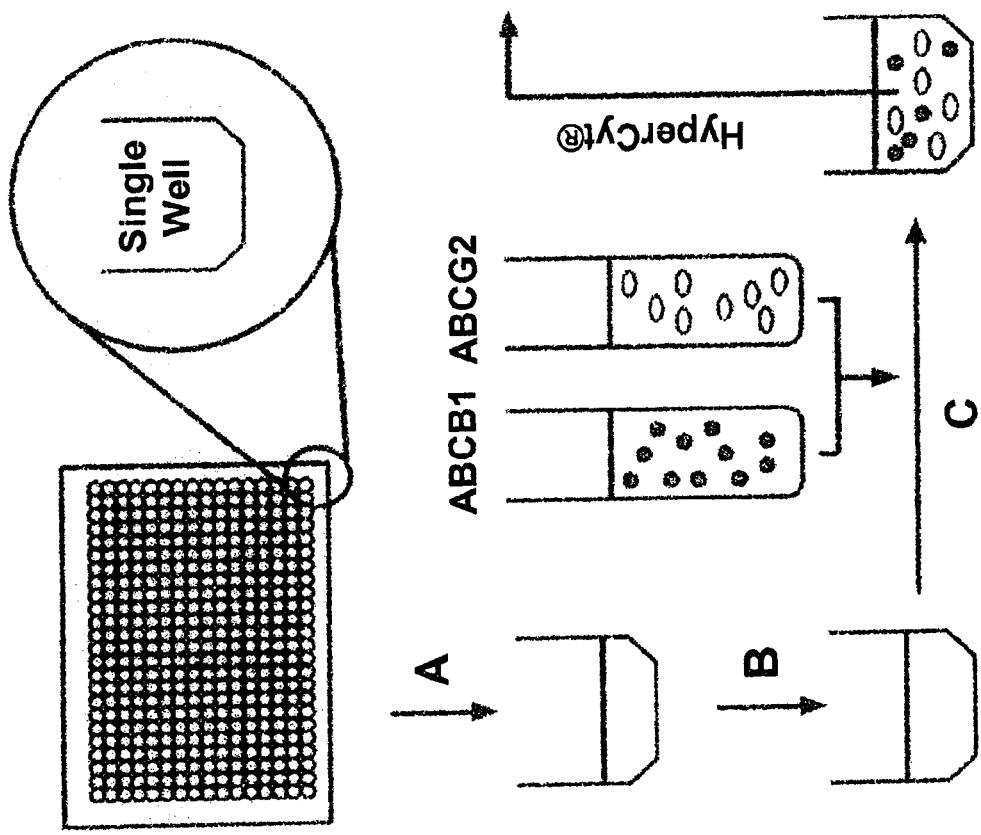

(Example 3)

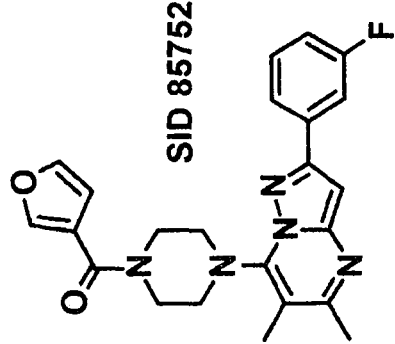
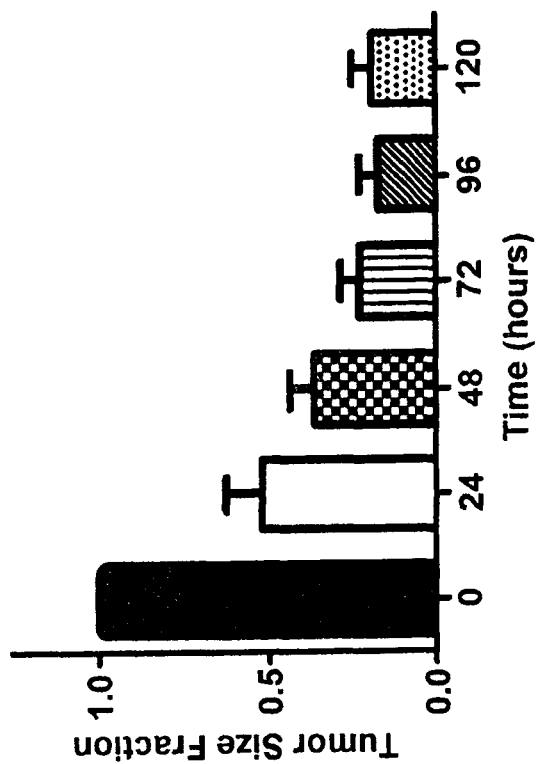
FIGURE 31

SELECTIVE EFFLUX INHIBITORS AND RELATED PHARMACEUTICAL COMPOSITIONS AND METHODS OF TREATMENT

This application claims priority from U.S. Provisional Application Ser. No. 61/537,199, entitled "Selective Efflux Inhibitors and Related Pharmaceutical Compositions and Methods of Treatment, filed Sep. 21, 2011, and U.S. Provisional Application Ser. No. 61/680,899, entitled "Selective ATP-binding Cassette Sub-Family G Member 2 Efflux Inhibitor Revealed Via High Throughput Flow Cytometry", filed Aug. 8, 2012, the entire contents of which are hereby incorporated by reference in their entirety.

RELATED APPLICATIONS AND FEDERALLY SPONSORED RESEARCH

The present invention was made with government support under Grant Nos. 5R01CA114589-01, 1RO3MH081228-01A1, U54 MH084690 and U54HG005031 awarded by the National Institutes of Health (NIH). Consequently, the Government has certain rights in this invention.

FIELD OF THE INVENTION

The present invention provides novel compounds which inhibit cancer-associated transporter proteins, methods of treating or preventing the onset of a cancer-associated transporter protein-mediated disease by administering such compounds, and pharmaceutical compositions comprising such compounds. In one embodiment, the invention provides novel pyrazolo[1,5-a]pyrimidine efflux inhibitors that are selective toward ABCG2 over ABCB1.

BACKGROUND OF THE INVENTION

More than 48 members of the ABC transporter superfamily have been identified and three major subfamilies (ABCB, ABCC, and ABCG) are related to human multidrug resistance (MDR) and influence oral absorption and disposition of a wide variety of drugs, and as a result their expression levels have important consequences for susceptibility to drug-induced side effects, interactions, and treatment efficacy. The specific subclass members ABCB1 (MDR1/Pgp), ABCC1 (MRP1), and ABCG2 (BCRP) are known to significantly influence the efficacy of drugs and have unambiguously been shown to contribute to cancer multidrug resistance.[1-2] Although a large number of compounds have been identified possessing ABC transporter inhibitory properties, only a few of these agents are appropriate candidates for clinical use as MDR reversing agents.[3-4] Dual treatment with ABC transporter inhibitors in conjunction with chemotherapeutics is a common treatment strategy to circumvent MDR in cancers.[5-6] However, the failure of current classes provide ample justification for identifying new classes of modulators and exploring the biology around them. These efflux pumps are expressed in many human tumors where they likely contribute to resistance to chemotherapy treatment. ABCB1, ABCC1, and ABCG2 are highly expressed in the gut, liver, and kidneys and they may restrict the oral bioavailability of administered drugs. ABCB1 and ABCG2 are also expressed in the epithelia of the brain and placenta and also in stem cells, where they perform a barrier function.[7] More specifically, ABCG2 relevance as a clinical target has been well documented.[8] This includes a mouse model using a human ovarian xenograft with Igrove1/T8 tumors,[9] a system utilizing flavopiridol-resistant human breast cancer cells,[10] an FTC/Ko 143 inhibition in vitro and mouse intestine model,[11] and a phase I/II trial with lapatinib in glioblastoma multiforme.[12]

Early clinical failures with ABCB1 inhibitors initially resulted in diminished enthusiasm. However, progress over the last decade has renewed activity in the field and a variety of modulators have been identified. ABC efflux transporter inhibition is now in its third generation with the majority of focus still on ABCB1. It has been observed that a large number of structurally and functionally diverse compounds act as substrates or modulators of these pumps with numerous publications dedicated to the subject.[13-16] A subset of these compounds will be discussed here. The first-generation of chemosensitizers were discovered from already approved drugs and included the calcium channel blocker verapamil (as well asnicardipine), cyclosporin A, and progesterone but dose-related toxicity and other adverse effects (i.e. solubility limitations) prevented progress into the clinic.[17-24] Second and third generation inhibitors were drawn predominantly from the derivatization of first-generation molecules as well as from combinatorial chemistry targeted primarily at ABCB1. Some of the higher profile examples include:the cyclosporin A derivative valspodar (PSC-833)[25]; Vertex Pharmaceuticals' biricodar (VX-710)[26-28]; the anthranilamide based modulators XR9051[29], tariquidar (XR9576)[30-32], XR9577[33-34], and WK-X-34[34][35]; the acridonecarboxamidederivativeelacridar (GF120918)[36]; the heteroaryloxypropanolamineszosuquidar (LY335979)[37-39] and dofequidar (MS-209)[40-41] (and the structurally related laniquidar (R101933)[42-43]), and diarylimidazoleontogen (OC144-093, ONT-093)[44-47]. The late generation inhibitors tended to be more potent and less toxic than the first-generation compounds, however, multiple issues remain.

Although much of the work to date is targeted at ABCB1, the selectivity profile of these inhibitors is significantly varied. Valspodar, tariquidar, elacridar, zosuquidar and ontogeny have been reported to be selective (though not necessarily specific) for ABCB1.[25-28,30-31,40] Those specific for ABCC1 include the quinoline based MK571 and the uricosuric drug probenecide.[48-49] Although there is significant progress with ABCB1 inhibitors, similar progress has not been made with ABCG2 inhibitors. The Aspergillusfumigatusmycotoxinfumitremorgin C (FTC) and its analogs Ko 132, Ko 134, and Ko 143 have been demonstrated to be selective inhibitors for ABCG2.[11,50-52] Other imidazoline and β-carboline amino acid benzyl ester conjugates analogous to FTC were labeled 'dual-acting' due to a cytotoxicity that was coupled to their resistance reversing activity.[53] Examples of cross pump inhibitors include verapamil, cyclosporin A, dofequidar, and reversanfor ABCB1/ABCC1 and biricodar and nicardipine-for ABCB1/ABCC1/ABCG2.[28,54-56]

Structural information for all mammalian ABC transporter family members is relatively sparse, with ABCB1 being the most extensively studied. The presence of multiple, potentially overlapping, binding sites and possible interactions between them may account for diverse specificity of structurally and functionally unrelated modulators and substrates. This polyspecificity also raises questions as to which substrate should be used to demonstrate inhibitory potential of a new chemical entity. In order to understand the mechanism and to design more effective modulators, great effort has been made to study the interaction of substrates and modulators with these transporters.[57] It was shown that most ABCB1 inhibitors are additionally substrates of the efflux pump.[58] It is important to not only evaluate inhibitor potency in a given transporter, but also to profile its activity with other transporters as well as its interrelationship with substrate drugs. For instance, strong inhibition of ABCB1 by drugs like cyclosporine or verapamil in in vitro models proved to be limited in in vivo studies due to toxic pharmacological effects of the inhibitors.[2] Our recent work further demonstrated differential cross-reactivity of inhibitors across ABCB1, ABCC1, and ABCG2 transporters and we demonstrated cross-reactivity of both these inhibitors across all three transporters, which could help explain such severe toxicity effects.[5,6] Such interactions can be quite complex, since the array of substrate/non-substrate and inhibitor/non-inhibitor is further clouded by the possibility of multiple interaction sites and unwarranted cytotoxicity.

Several of the afformentioned small molecule inhibitors were selected to help profile the compounds of interest in vitro (FIG. 1). Compounds were chosen specifically for their reported selectivity profiles. The sub-micromolar modulator of ABCB1 XR9051 (a precursor to tariquidar) has been shown to reverse resistance to cytotoxic drugs such as doxorubicin and vincristine.[3,29] The previously mentioned MK 571 is documented as a specific inhibitor of ABCC1.[59] For direct comparison of selective inhibition of ABCG2 both FTC and Ko 143 were chosen.[11,50-52] Also, the pyrazolopyrimidine reversan, with a similar core to our inhibitor class, was identified as an active inhibitor of ABCB1 and ABCC1.[54]

SUMMARY OF THE INVENTION

The present invention relates to compounds which inhibit cancer-associated transporter proteins and methods of treatment that use such compounds to mediate a variety of disease states, in particular cancer, and especially drug resistant (DR) and multiple drug resistant (MDR) cancer. In one embodiment, the invention provides novel pyrazolo[1,5-a]pyrimidine efflux inhibitors that are selective toward ABCG2 over ABCB1. These compounds have low in vitro cellular toxicity, are soluble, and are stable.

Accordingly, the invention provides a compound of formula (I), or an enantiomer, diastereomer, tautomer, or pharmaceutically-acceptable salt or hydrate thereof:

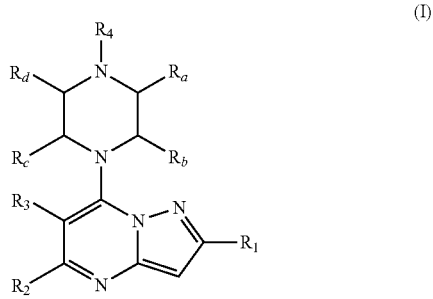

(I)

wherein
$R_1$ is selected from the group consisting of substituted or unsubstituted alkyl, substituted or unsubstituted alkylene, substituted or unsubstituted alkynyl, substituted or unsubstituted heterocycloalkyl, substituted or unsubstituted aryl, substituted or unsubstituted heteroaryl, substituted or unsubstituted arylalkyl, and substituted or unsubstituted heteroarylalkyl;
$R_2$ and $R_4$ are independently selected from the group consisting of hydrogen, halogen, hydroxy, carboxyl, acyl, amino, amide, substituted or unsubstituted alkyl, substituted or unsubstituted alkylene, substituted or unsubstituted alkynyl, substituted or unsubstituted heterocycloalkyl, substituted or unsubstituted aryl, substituted or unsubstituted heteroaryl, substituted or unsubstituted arylalkyl, and substituted or unsubstituted heteroarylalkyl;
$R_3$ is selected from the group consisting of hydrogen, halogen, hydroxy, carboxyl, acyl, amino, amide, substituted or unsubstituted alkyl, substituted or unsubstituted alkylene, or substituted or unsubstituted alkynyl; and wherein
$R_a$, $R_b$, $R_c$, and $R_d$ are independently selected from the group consisting of hydrogen, halogen, hydroxy, carboxyl, oxo, acyl, amino, amide, substituted or unsubstituted alkyl, substituted or unsubstituted alkylene, or substituted or unsubstituted alkynyl, or one or more of $R_a$, $R_b$, $R_c$, and $R_d$, together with the carbon ring atom to which it is bound, forms carbonyl.

In a preferred embodiment of the compounds of formula (I), $R_1$ is selected from the group consisting of substituted or unsubstituted aryl, $R_2$ is selected from the group consisting of substituted or unsubstituted alkyl, substituted or unsubstituted aryl, and substituted or unsubstituted heteroaryl, $R_3$ is selected from the group consisting of hydrogen and substituted or unsubstituted alkyl, $R_4$ is either (1) an acyl group which includes either a substituted or unsubstituted aryl or a substituted or unsubstituted heteroaryl moiety, or (2) is a substituted or unsubstituted arylalkyl or a substituted or unsubstituted heteroarylalkyl, and $R_a$, $R_b$, $R_c$, and $R_d$ are hydrogen.

In a more preferred embodiment of the compounds of formula (I), $R_1$ is substituted or unsubstituted phenyl, $R_2$ is a substituted or unsubstituted $C_1$-$C_3$ alkyl or is a substituted or unsubstituted heteroaryl, $R_3$ is hydrogen, $R_4$ is $R_xR_y$, where $R_x$ is bound to the nitrogen ring atom and is either carbonyl or $CH_2$ and $R_y$ is a 5 or 6-membered, substituted or unsubstituted heteroaryl, and $R_a$, $R_b$, $R_c$, and $R_d$ are hydrogen.

In a still more preferred embodiment of the compounds of formula (I), $R_1$ is substituted or unsubstituted phenyl, $R_2$ is a substituted or unsubstituted 5 or 6-membered heteroaryl, $R_3$ is hydrogen, $R_4$ is $R_xR_y$, where $R_x$ is bound to the nitrogen ring atom and is either carbonyl or $CH_2$ and $R_y$ is a 5 or 6-membered, substituted or unsubstituted heteroaryl, and $R_a$, $R_b$, $R_c$, and $R_d$ are hydrogen.

In an even more preferred embodiment of the compounds of formula (I), $R_1$ is substituted or unsubstituted phenyl, $R_2$ is a substituted or unsubstituted furan, $R_3$ is hydrogen, $R_4$ is $R_xR_y$, where $R_x$ is bound to the nitrogen ring atom and is either carbonyl or $CH_2$ and $R_y$ is substituted or unsubstituted furan, and $R_a$, $R_b$, $R_c$, and $R_d$ are hydrogen.

In another preferred embodiment, the invention provides a compound of formula (I), or an enantiomer, diastereomer, tautomer, or pharmaceutically-acceptable salt or hydrate thereof, wherein the compound is:

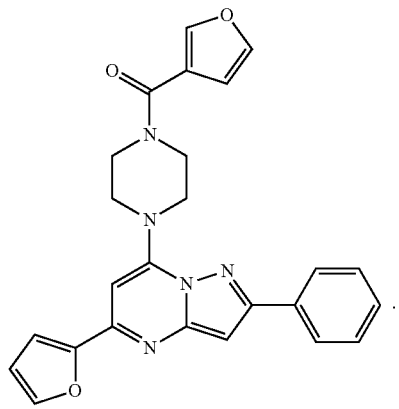

SID 88095709

In another preferred embodiment, the invention provides a compound of formula (I), or an enantiomer, diastereomer, tautomer, or pharmaceutically-acceptable salt or hydrate thereof, wherein the compound is:

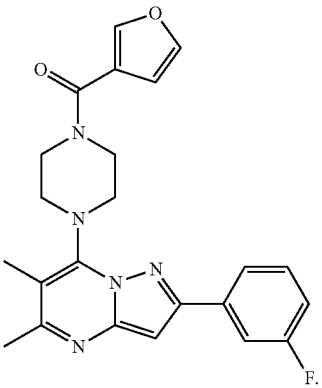

SID 85752814

In another preferred embodiment, the invention provides a compound of formula (I), or an enantiomer, diastereomer, tautomer, or pharmaceutically-acceptable salt or hydrate thereof, wherein the compound is:

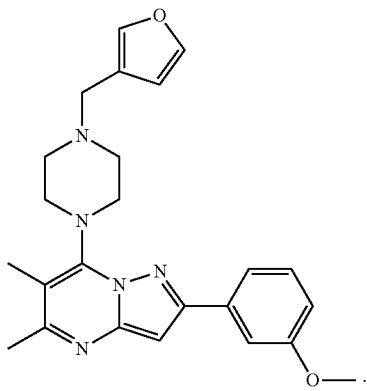

SID 97301789

In another preferred embodiment, the invention provides a compound of formula (I), or an enantiomer, diastereomer, tautomer, or pharmaceutically-acceptable salt or hydrate thereof, wherein $R_1$ and $R_2$ are substituted or unsubstituted phenyl, $R_3$ is hydrogen, $R_4$ is CO-3-pyridyl, and $R_a$, $R_b$, $R_c$, and $R_d$ are hydrogen.

In another preferred embodiment, the invention provides a compound of formula (I), or an enantiomer, diastereomer, tautomer, or pharmaceutically-acceptable salt or hydrate thereof, wherein $R_1$ is 3-Cl-phenyl, $R_2$ is phenyl, $R_3$ is hydrogen, $R_4$ is CO-3-pyridyl, and $R_a$, $R_b$, $R_c$, and $R_d$ are hydrogen.

In another preferred embodiment, the invention provides a compound of formula (I), or an enantiomer, diastereomer, tautomer, or pharmaceutically-acceptable salt or hydrate thereof, wherein $R_1$ is phenyl, $R_2$ is 2-F-phenyl, $R_3$ is hydrogen, $R_4$ is CO-3-furyl, and $R_a$, $R_b$, $R_c$, and $R_d$ are hydrogen.

In another preferred embodiment, the invention provides a compound of formula (I), or an enantiomer, diastereomer, tautomer, or pharmaceutically-acceptable salt or hydrate thereof, wherein $R_1$ is 3-Cl-phenyl, $R_2$ is 3-pyridyl, $R_3$ is hydrogen, $R_4$ is CO-3-furyl, and $R_a$, $R_b$, $R_c$, and $R_d$ are hydrogen.

In another preferred embodiment, the invention provides a compound of formula (I), or an enantiomer, diastereomer, tautomer, or pharmaceutically-acceptable salt or hydrate thereof, wherein $R_1$ is phenyl, $R_2$ is 3-MeO-phenyl, $R_3$ is hydrogen, $R_4$ is CO-3-furyl, and $R_a$, $R_b$, $R_c$, and $R_d$ are hydrogen.

In another preferred embodiment, the invention provides a compound of formula (IA), or an enantiomer, diastereomer, tautomer, or pharmaceutically-acceptable salt or hydrate thereof:

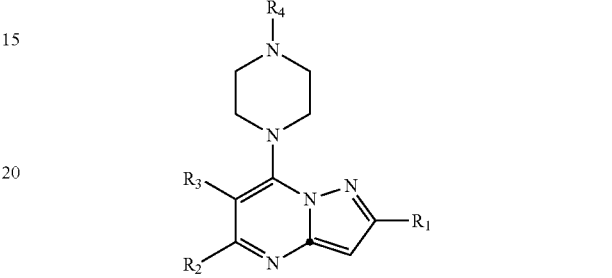

(IA)

wherein $R_1$, $R_2$, $R_3$ and $R_4$ are as defined for formula (I).

In another preferred embodiment, the invention provides a compound of formula (IA), or an enantiomer, diastereomer, tautomer, or pharmaceutically-acceptable salt or hydrate thereof, wherein $R_1$ is substituted or unsubstituted phenyl; $R_2$ is alkyl (preferably methyl), substituted or unsubstituted phenyl or a substituted or unsubstituted five-membered heteroaryl containing one or two ring heteroatoms selected from the group consisting of O and N; $R_3$ is hydrogen or alkyl (preferably methyl); and $R_4$ is alkyl-phenyl or an acyl group containing either a substituted or unsubstituted phenyl or a five-membered, substituted or unsubstituted heteroaryl containing one or two ring heteroatoms selected from the group consisting of O and N.

In another preferred embodiment, the invention provides a compound of formula (IA), or an enantiomer, diastereomer, tautomer, or pharmaceutically-acceptable salt or hydrate thereof, wherein $R_1$ is phenyl substituted by either halogen (most preferably Cl or F) or lower alkoxy (most preferably methoxy), or $R_1$ is unsubstituted phenyl; $R_2$ is alkyl (preferably methyl), phenyl substituted by either halogen (most preferably F) or lower alkoxy (most preferably methoxy), or $R_2$ is furyl; $R_3$ is hydrogen or alkyl (most preferably methyl); and $R_4$ is alkyl-phenyl, benzoyl substituted by halogen (most preferably Cl) or lower alkoxy (most preferably methoxy), or $R_4$ is furoyl.

In another preferred embodiment, the invention provides a compound of formula (IA), or an enantiomer, diastereomer, tautomer, or pharmaceutically-acceptable salt or hydrate thereof, wherein $R_1$ is unsubstituted phenyl; $R_2$ is phenyl substituted by either halogen (most preferably F) or lower alkoxy (most preferably methoxy), or $R_2$ is furyl; $R_3$ is hydrogen; and $R_4$ is benzoyl substituted by either halogen (most preferably Cl) or lower alkoxy (most preferably methoxy), or $R_4$ is furoyl.

In one aspect of the invention, a compound of formulae (I) or (IA), or an enantiomer, diastereomer, tautomer, or pharmaceutically-acceptable salt or hydrate thereof, is administered to a patient in need thereof to treat or prevent the onset of a cancer-associated transporter protein mediated disease.

In another aspect of the invention, a compound of formula (I) or (IA), or an enantiomer, diastereomer, tautomer, or pharmaceutically-acceptable salt or hydrate thereof, and an adjuvant anti-cancer therapy, are co-administered to a patient in need thereof to treat or prevent the onset of a cancer-associated transporter protein mediated disease.

In still another aspect, the invention provides a method of treating a patient who suffers from a tumor containing ABCG2 resistant tumor cells by administering to the patient a pharmaceutically effective amount of a compound of formulae (I) or (IA), or an enantiomer, diastereomer, tautomer, or a pharmaceutically-acceptable salt or hydrate thereof. In certain aspects, the patient's tumor has proven non-responsive to chemotherapy prior to treatment.

Pharmaceutical compositions which comprise an effective amount of a compound of formula (I) or (IA) or as otherwise disclosed in the present application, or an enantiomer, diastereomer, tautomer, or pharmaceutically-acceptable salt or hydrate thereof, are also provided. In some embodiments, these pharmaceutical compositions include an effective amount at least one additional anti-cancer agent, especially as otherwise described herein, optionally in combination with a pharmaceutically acceptable carrier, additive or excipient.

These and other aspects of the invention are described further hereinafter in the detailed description of the invention.

BRIEF DESCRIPTION OF THE FIGURES

FIG. 11 summarizes a comparison of known compounds to SID 88095709, 85752814, and 97301789.

FIG. 15 shows Table 2, which summarizes a continuation of SAR expansion on initial hit SID 85240370.

FIG. 16 shows Table 3, which summarizes a series of modifications of formula (I) variable $R_1$.

FIG. 18 shows Table 5, which summarizes a series of modifications of formula (I) variable $R_4$.

FIG. 19 shows Table 6, which summarizes piperazine and combined $R_4$ modifications (X).

FIG. 20 shows Table 7, which summarizes analogues with $R_1$-$R_4$ substitution patterns in combination.

FIG. 21 shows Table 8, which summarizes the percent of activity remaining for various kinases when inhibited by SID 88095709.

FIG. 26 (Example 2). General scheme for the duplex HTS flow cytometric screening campaign. (A) In 384 well format, 1 µM JC-1 in PBS is added to the assay wells. (B) A volume of 100 nL of test compound is added to each well via pintool transfer (final concentration of 6.6 µM). (C) A 3×10$^6$ cells mL$^{-1}$ mixture of both cell lines is added to each well. The ABCB1 cell line was previously color-coded with CellTrace™ Far Red DDAO-SE prior to mixture with the unlabeled ABCG2 line. (D) Flow cytometric data of light scatter and fluorescence emission at 530+/−20 nm (488 nm excitation, FL1) and 665+/−10 nm (633 nm excitation, FL8) are then collected via HyperCyt®. Each population is gated in FL8 allowing for analysis of FL1 in individual time bins for each cell line. The JC-1 retention can then be quantified as an indication of efflux inhibition by test compound(s). The FL1 versus time excerpt shown represents 24 binned wells of a 384 well plate.

FIG. 31 (Example 3). Time course of injection of 100 nM Topotecan in conjunction with 500 nM compound SAI 85752814 into mice (n=5). Chemotherapeutic (topotecan) resistant Igrov1/T8 cells over-expressing ATP Binding Cassette G2 (ABCG2) were xenografted subcutaneously into the hind limbs of CB-17/SCID mice. The mice were injected intra-tumorally with 100 nM topotecan in conjunction with 500 nM compound #37 (SID 85752814) every 24 hours. The affect of this combination therapy is shown above a period of 5 days (120 hours). Tumor size was reduced by 81% ($p<0.001$). No reduction in size was observed in tumors treated with either 100 nM topotecan or 500 nM compound #37 alone.

DEFINITIONS

Figure 1:
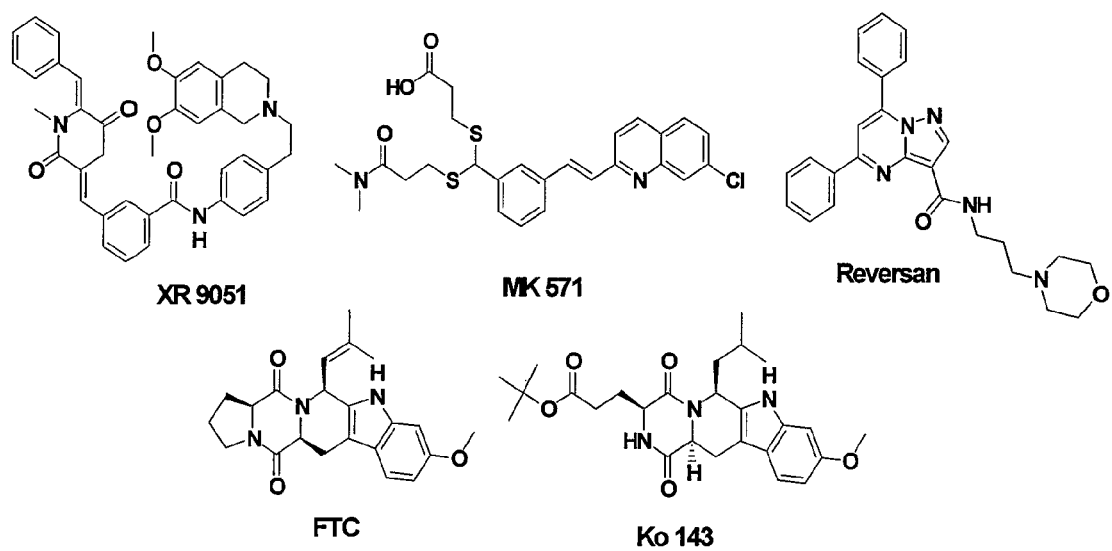
FIG. 1 depicts structures of small molecules chosen for direct experimental comparison in connection with the making of the claimed, invention.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

"Alkyl" refers to a fully saturated monovalent radical containing carbon ($C_1$-$C_{12}$) and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. "Alkenyl" refers to an unsaturated aliphatic hydrocarbon containing at least one double bond. "Alkynyl" means an unsaturated aliphatic hydrocarbon containing at least one triple bond. Preferred alkylene groups include $C_1$-$C_6$ alkylene groups. Other terms used to indicate substitutent groups in compounds according to the present invention are as conventionally used in the art.

"Aryl" or "aromatic", in context, refers to a substituted or unsubstituted monovalent aromaticradical having a single ring (e.g., benzene) or multiple condensed rings (e.g., naphthyl, anthracenyl, phenanthryl) and can be can be bound to the compound according to the present invention at any position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, pyridyl, furanyl, thiene, thiazole, pyridine, pyrimidine, pyrazine, triazole, oxazole, indole or fused ring systems (bicyclic, tricyclic), among others, which may be substituted or unsubstituted as otherwise described herein.

The term "cyclic" shall refer to an optionally substituted carbocyclic or heterocyclic group, preferably a 5- or 6-membered ring or fused rings (two or three rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred carbocyclic groups are unsaturated, and include phenyl groups, among other groups. Preferred heterocyclic groups are heteroaryl or heteroaromatic.

The term "heterocyclic group" as used throughout the present specification refers to an aromatic or non-aromatic cyclic group having 3 to 14 atoms, preferably 5 to 14 atoms forming the cyclic ring(s) and including at least one hetero atom such as nitrogen, sulfur or oxygen among the atoms forming the cyclic ring, which is an aromatic heterocyclic group (also, "heteroaryl" or "heteroaromatic") in the former case and a "non-aromatic heterocyclic group" in the latter case. Specific examples of the heterocyclic group therefore include specific examples of the aromatic heterocyclic group and specific examples of the non-aromatic heterocyclic group, both of which groups fall under the rubric "heterocyclic group" as otherwise described herein. Among the heterocyclic groups which may be mentioned for use in the present invention within context include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 14-membered heterocyclic groups and all subsets of heterocyclic groups (including non-heteroaromatic or heteroaromatic) subsumed under the definition of heterocyclic group.

Among the heterocyclic groups for use in the present invention may preferably include pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, pyridine-N-oxide, thiophene, benzothiophene, thiazole, benzothiazole, quinoline, quinazoline, cinnoline and carbostyryl, and even more preferably thiazole, quinoline, quinazoline, cinnoline and carbostyryl, among others.

Among the bicyclic or tricyclic heterocyclic groups which may be used in the present invention include indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "substituted" shall mean substituted at a carbon (or nitrogen) position within context, hydroxyl, carboxyl, cyano (CN), nitro ($NO_2$), halogen (preferably, 1, 2 or 3 halogens, especially on an alkyl, especially a methyl group such as a trifluoromethyl), thiol, an optionally substituted alkyl, alkene or alkyne group (preferably, $C_1$-$C_6$, $C_2$-$C_6$, more preferably $C_1$-$C_3$, $C_2$-$C_3$), optionally substituted aryl (especially optionally substituted phenyl or benzyl), optionally substituted heterocyclic (especially optionally substituted heteroaryl for example, pyridyl (2-, 3-, 4-), pyrimidinyl, thienyl (2- or 3-), furanyl (2- or 3-), alkoxy (preferably, $C_1$-$C_6$ alkyl or aryl), optionally substituted ether (preferably, $C_1$-$C_{10}$ alkyl ether, alkenylether, alkynyl ether or aryl ether, including phenyl or benzyl ether), acyl (preferably $C_2$-$C_8$ acyl which may include an aryl substituted acyl), optionally substituted ester (preferably, $C_1$-$C_6$ alkyl or aryl) including alkylene, alkenyl or alkynyl ester (alkylene attachment to compound), ketoester (carbonyl attachment to compound) or hydroxyester (oxygen attachment to compound), thioether (preferably, $C_1$-$C_6$ alkyl or aryl), thioester (preferably $C_1$-$C_6$ alkyl or aryl), amine (including a five- or six-membered cyclic alkylene amine, including an optionally substituted $C_1$-$C_6$ alkyl amine (e.g., monoalkanolamine) or an optionally substituted $C_1$-$C_6$ dialkyl amine (e.g. dialkanolamine), alkanol (preferably, $C_1$-$C_6$ alkyl or aryl), or alkanoic acid (preferably, $C_1$-$C_6$ alkyl or aryl), optionally substituted carboxyamide (carbonyl attached to the carbon atom with one or two substituents on the amine group—preferably H or an optionally substituted $C_1$-$C_6$ alkyl group), amido group (amine group with H or $C_1$-$C_3$ alkyl group attached to the carbon atom with a single group, preferably H or an optionally substituted $C_1$-$C_6$ alkyl group on the keto group) or an optionally substituted urethane group (with either the amine or the O-carboxy group attached to a carbon atom to which the urethane is a substituent—the amine group being substituted with one or two H or one or two $C_1$-$C_6$ alkyl groups). Preferably, the term "substituted" shall mean within the context of its use alkyl, alkoxy, halogen, hydroxyl, carboxylic acid, cyano, ether, ester, acyl, nitro, amine (including mono- or di-alkyl substituted amines) and amide, as otherwise described above. Any substitutable position in a compound according to the present invention may be substituted in the present invention. Preferably no more than 5, more preferably no more than 3 substituents are present on a single ring or ring system. Preferably, the term "unsubstituted" shall mean substituted with one or more H atoms. It is noted that in describing a substituent, all stable permutations of the substituent are intended.

Preferred substituents for use in the present invention include, for example, F, Cl, CN, $NO_2$, $CH_3$, $CH_2OH$, $CH_2CH_3$, $CH_2OCH_3$, $CF_3$, $CO_2CH_3$, optionally substituted thienyl, optionally substituted furanyl (especially $CH_2OCH_2$-furanyl), optionally substituted pyridyl (especially CH₂OCH₂-pyridyl), optionally substituted pyrimidyl and optionally substituted phenyl, including benzyl (CH₂OCH₂-phenyl).

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single small molecule as disclosed herein, but in certain instances may also refer to stereoisomers and/or optical isomers (including racemic mixtures) of disclosed compounds. The term compound or "agent" includes active metabolites of compounds and/or pharmaceutically active salts thereof.

The term "inhibitor" is used herein to refer to any compound which inhibits cancer-associated transporter proteins (e.g. especially inhibition of ABCG2, but also, in certain instances, ABCC1 or ABCB1, or inhibition which is selective toward ABCG2 over ABCB1 or which produces an inhibition of ABCB1 transporter protein by any mechanism, direct or indirect, whether it be by inhibition of the interaction of ABCG2 and/or ABCB1 transporter proteins with their intended receptor or other target or whether it be by inhibition of the expression of ABCG2 and/or ABCB1 transporter proteins).

The term "effective amount" is used throughout the specification to describe concentrations or amounts of compounds or other components which are used in amounts, within the context of their use, to produce an intended effect according to the present invention. The compound or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where compounds are used in combination, each of the compounds is used in an effective amount, wherein an effective amount may include a synergistic amount. In many instances, the term effective amount refers to that amount which inhibits expression of ABCG2 and/or ABCB1 transporter proteins and consequently, results in a diminution of resistance to a therapeutic approach, to symptoms or results in an actual cure of a disease state such as cancer, which cancer may include drug resistant cancer, especially a multiple drug resistant (MDR) cancer, a cancer such as a leukemia or a cancerous tumor, especially including T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, among others.

In the present invention all compounds are used in effective amounts to provide activity relevant to the use of the compound. In combination therapy, the cancer-associated transporter protein-inhibiting compounds (e.g. ABCG2 and/or ABCB1 transporter protein inhibitors) and the anticancer agent are both used in effective amounts. The amount of compound used in the present invention may vary according to the nature of the compound, the age and weight of the patient and numerous other factors which may influence the bioavailability and pharmacokinetics of the compound, the amount of compound which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "cancer-associated transporter protein mediated disease" is used throughout the specification to describe a disease which is mediated through the action or overexpression of any cancer-related transporter protein, e.g. any or all of the ABCG2, ABCC1 and ABCB1 transporter proteins, or where the overexpression of such transporter proteins occurs in conjunction with the disease state. Diseases which may be treated according to the present invention include a cancerous disease state, in particular, a drug resistant cancer, a multiple drug resistant cancer, a leukemia or related hematopoietic cancer, including T-ALL and related leukemias, especially drug resistant (multiple) leukemias, such as T-ALL, and numerous cancerous tumors as otherwise described herein. These diseases may include any one or more of hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, T-lineage acute lymphoblastic leukemia (T-ALL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia. Other cancers, including cancerous tumors, which may be treated using the present invention include for example, stomach (especially including gastric stromal cells), colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, skin cancer, including melanoma and non-melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others. Additional cancers which may be particularly responsive to therapeutic methods according to the present invention include for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, breast cancer, Ewing's sarcoma, osteosarcoma and undifferentiated high-grade sarcomas, among others.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all cancerous disease states and embraces or encompasses the pathological process associated with cancer, including hematopoietic cancers, numerous cancerous tumors and their metastasis.

A "hematopoietic neoplasm" or "hematopoietic cancer" is a neoplasm or cancer of hematopoeitic cells of the blood or lymph system and includes disease states such as Hodgkin's disease, non-Hodgkin's lymphoma, leukemias, including non-acute and acute leukemias, such as acute myelogenous leukemia, acute lymphocytic leukemia, acute promyelocytic leukemia (APL), adult T-cell leukemia, T-lineage acute lymphoblastic leukemia (T-ALL), basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia, among others.

The present method may be used to treat all cancers (including drug resistant and multiple drug resistant cancers), especially the above hematopoietic and tumorigenic cancers which exhibit an overexpression of ABCG2 and/or ABCB1 transporter proteins. While T-ALL and especially multiple drug resistant T-ALL are particularly relevant disease targets for the methods of the present invention, virtually any cancer implicating any cancer-related transporter protein, e.g. any or all of the ABCG2, ABCC1 and ABCB1 transporter proteins, or where any of the ABCG2, ABCC1 and ABCB1 transporter proteins are implicated in instilling drug resistance or multiple drug resistance to the cancer and/or tumor is an appropriate target of the present therapeutic methods and compositions according to the present invention. Cancers which are particularly response to the present invention include T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, breast cancer, Ewing's sarcoma, osteosarcoma and undifferentiated high-grade sarcomas, among others. Other cancers which may be treated according to the present invention include for example, stomach (especially including gastric stromal cells), colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, skin cancer, including melanoma and non-melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, including drug resistant (DR) and multiple drug resistant (MDR) forms of each of these cancers.

The term "prophylactic" is used to describe the use of a compound described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of the present compounds or a carrier, additive or excipient which is not unacceptably toxic to the subject to which it is administered.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascetic and solid tumors.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

DETAILED DESCRIPTION OF THE INVENTION

The present disclosure provides novel small molecules that inhibit cancer-related transporter proteins, e.g. ABCG2, ABCC1 and ABCB1 transporter proteins, in cancer disease states, especially hematopoietic cancers and cancerous tumors as otherwise described herewith especially including those which are drug resistant, especially those disease states which are drug resistant as a consequence of overexpression of ABCG2, ABCC1 or ABCB1 transporter protein. Various cancers as otherwise described herein may be treated using the methods of the present invention, especially including cancers exhibiting multiple drug resistance. Particularly responsive cancers to the present methods include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, breast cancer, Ewing's sarcoma, osteosarcoma and undifferentiated high-grade sarcomas, among others.

The present invention also relates to an identification of the unexpected activity of compounds which are well known in the art, but have heretofore not been known to be inhibitors of ABCG2, ABCC1 and ABCB1. Methods of making these compounds and incorporating these compounds into pharmaceutical compositions are well known in the art. Pharmaceutically acceptable salts prepared from the active compounds are readily prepared. The present invention is not limited in any way by the method of synthesis of compounds, but encompasses all small molecules otherwise identified that may be produced by any suitable method of synthesis. Compounds may be synthesized step-wise by first synthesizing various synthons and then condensing the synthons together to produce compounds according to the invention. The synthesis of compounds according to the present invention is well within the routine skill of the person of ordinary skill. If desired, intermediates and products may be purified by chromatography and/or recrystallization. Starting materials, intermediates and reagents are either commercially available or may be prepared by one skilled in the art using methods described in the relevant chemical literature. Most of the compounds which are used therapeutically in the present invention are known in the art, as are the methods of their synthesis.

The present invention includes, where applicable, the compositions comprising the pharmaceutically acceptable salts, in particular, acid or base addition salts of compounds of the present invention. The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds of the present invention may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient. Compounds according to the present invention may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The amount compound which is used in the present invention, whether that compound is an ABCG2, ABCC1 or ABCB1 transporter protein inhibitor or an anticancer compound is that amount effective within the context of the administration of the compound(s). A suitable oral dosage for a compound of the present invention would be in the range of about 0.01 mg to 10 g or more per day, preferably about 0.1 mg to about 1 g per day. In parenteral formulations, a suitable dosage unit may contain from about 0.1 to about 250-500 mg of said compounds, which may be administered continuously or from one to four times per day, whereas for topical administration, formulations containing 0.01 to 1% or more by weight active ingredient are preferred. It should be understood, however, that the dosage administered from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like. Immediate release, intermediate release and sustained and/or controlled release formulations are contemplated by the present invention.

The pharmaceutical formulations/preparations according to the present invention can be prepared in a conventional manner and finished dosage forms can be solid dosage forms, for example, tablets, dragees, capsules, and other like oral dosage forms, or liquid dosage forms, for example solutions, suspensions, emulsions and the like.

The pharmaceutical formulations/preparations may be subjected to conventional pharmaceutical operations such as sterilization. Further, the pharmaceutical preparations may contain conventional additives and excipients such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous (saline) or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chlorobutanol or phenylethyl alcohol, among numerous others.

In certain aspects according to the present invention, where various cancers are to be treated, the compounds may be co-administered with at least one other anti-cancer agent such as antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cisplatin. By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anticancer agents produces a synergistic (i.e., more than additive) result which is unexpected.

Additional compounds which may be used in combination with the compounds uncovered in the present invention include for example: adriamycin, anastrozole, arsenic trioxide, asparaginase, azacytidine, BCG Live, bevacizumab, bexarotene capsules, bexarotene gel, bleomycin, bortezombi, busulfan intravenous, busulfan oral, calusterone, campothecin, capecitabine, carboplatin, carmustine, carmustine with polifeprosan 20 implant, celecoxib, cetuximab, chlorambucil, cisplatin, cladribine, clofarabine, cyclophosphamide, cytarabine, cytoxan, cytarabine liposomal, dacarbazine, dactinomycin, actinomycin D, dalteparin sodium, darbepoetin alfa, dasatinib, daunorubicin liposomal, daunorubicin, daunomycin, decitabine, denileukin, denileukin diftitox, dexrazoxane, dexrazoxane, docetaxel, doxorubicin, doxorubicin liposomal, dromostanolone propionate, eculizumab, Elliott's B Solution, epirubicin, epirubicin hcl, epoetin alfa, erlotinib, estramustine, etoposide phosphate, etoposide VP-16, exemestane, fentanyl citrate, filgrastim, floxuridine (intraarterial), fludarabine, fluorouracil 5-FU, fulvestrant, gefitinib, gemcitabine, gemcitabine hcl, gemicitabine, gemtuzumab ozogamicin, goserelin acetate, goserelin acetate, histrelin acetate, hydroxyurea, ibritumomab tiuxetan, idarubicin, ifosfamide, imatinib mesylate, interferon alfa 2a, interferon alfa-2b, irinotecan, lapatinib ditosylate, lenalidomide, letrozole, leucovorin, leuprolide acetate, levamisole, lomustine CCNU, meclorethamine, nitrogen mustard, megestrol acetate, melphalan L-PAM, mercaptopurine 6-MP, mesna, methotrexate, methoxsalen, mitomycin C, mitotane, mitoxantrone, nandrolone phenpropionate, nelarabine, nofetumomab, oprelvekin, oxaliplatin, paclitaxel, paclitaxel protein-bound particles, palifermin, pamidronate, panitumumab, pegademase, pegaspargase, pegfilgrastim, peginterferon alfa-2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide VM-26, testolactone, thalidomide, thioguanine 6-TG, thiotepa, topotecan, topotecan hcl, toremifene, tositumomab, tositumomab/I-131 tositumomab, trastuzumab, tretinoin ATRA, uracil mustard, valrubicin, vinblastine, vincristine, vinorelbine, vorinostat, zoledronate, zoledronic acid and mixtures thereof.

In a pharmaceutical composition aspect of the present invention at least one compound selected from the group consisting of bepridil, lidoflazine, nicardipine, propafenone, rescinnamine, GBR 12909, ellipticine, hexestrol, loxapine, pimozide, acacetin, mometasone furoate or its active 6-β-hydroxy metabolite, ketoconazole and cyclosporin A, and mixtures thereof or their pharmaceutically acceptable salts (preferably, bepridil, nicardipine, propafenone, rescinnamine, ketoconazole, cyclosporine A, loxapine, pimozide, acacetin, mometasone furoate, its active 6β-hydroxy metabolite and mixtures thereof) is combined with at least one compound according to the present invention and an additional anticancer compound (agent) in an effective amount in combination with a pharmaceutically acceptable carrier, additive or excipient to treat cancer, or to reduce the likelihood of an occurrence, a recurrence or metastasis of any one or more of the cancers specifically identified in the present application.

The above identified compound(s) may be combined with at least one agent selected from the group consisting of antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cisplatin for the treatment of cancer, as otherwise described herein. Additional agents which may be combined in pharmaceutical compositions according to the present invention include, for example, adriamycin, anastrozole, arsenic trioxide, asparaginase, azacytidine, BCG Live, bevacizumab, bexarotene capsules, bexarotene gel, bleomycin, bortezombi, busulfan intravenous, busulfan oral, calusterone, campothecin, capecitabine, carboplatin, carmustine, carmustine with polifeprosan 20 implant, celecoxib, cetuximab, chlorambucil, cisplatin, cladribine, clofarabine, cyclophosphamide, cytarabine, cytoxan, cytarabine liposomal, dacarbazine, dactinomycin, actinomycin D, dalteparin sodium, darbepoetin alfa, dasatinib, daunorubicin liposomal, daunorubicin, daunomycin, decitabine, denileukin, denileukin diftitox, dexrazoxane, dexrazoxane, docetaxel, doxorubicin, doxorubicin liposomal, dromostanolone propionate, eculizumab, Elliott's B Solution, epirubicin, epirubicin hcl, epoetin alfa, erlotinib, estramustine, etoposide phosphate, etoposide VP-16, exemestane, fentanyl citrate, filgrastim, floxuridine (intraarterial), fludarabine, fluorouracil 5-FU, fulvestrant, gefitinib, gemcitabine, gemcitabine hcl, gemicitabine, gemtuzumab ozogamicin, goserelin acetate, goserelin acetate, histrelin acetate, hydroxyurea, ibritumomab tiuxetan, idarubicin, ifosfamide, imatinib mesylate, interferon alfa 2a, interferon alfa-2b, irinotecan, lapatinib ditosylate, lenalidomide, letrozole, leucovorin, leuprolide acetate, levamisole, lomustine CCNU, meclorethamine, nitrogen mustard, megestrol acetate, melphalan L-PAM, mercaptopurine 6-MP, mesna, methotrexate, methoxsalen, mitomycin C, mitotane, mitoxantrone, nandrolone phenpropionate, nelarabine, nofetumomab, oprelvekin, oxaliplatin, paclitaxel, paclitaxel protein-bound particles, palifermin, pamidronate, panitumumab, pegademase, pegaspargase, pegfilgrastim, peginterferon alfa-2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide VM-26, testolactone, thalidomide, thioguanine 6-TG, thiotepa, topotecan, topotecan hcl, toremifene, tositumomab, tositumomab/I-131 tositumomab, trastuzumab, tretinoin ATRA, uracil mustard, valrubicin, vinblastine, vincristine, vinorelbine, vorinostat, zoledronate, zoledronic acid and mixtures thereof.

Alternative pharmaceutical compositions according to the present invention may comprise an effective amount of a compound according to the present invention and at least one compound selected from the group consisting of bepridil, nicardipine, propafenone, rescinnamine, ketoconazole, cyclosporine A, loxapine, pimozide, acacetin, mometasone furoate, its active 6β-hydroxy metabolite and mixtures thereof, or their pharmaceutically acceptable salts and mixtures thereof (preferably, including at least mometasone furoate, its active 6β-hydroxy metabolite or a pharmaceutically acceptable salt thereof), in combination with one or more anticancer agents as otherwise disclosed herein and in particular, at least one compound selected from the group consisting of anthracyclines (daunorubin, doxorubicin, epirubicin, idarubicin, and valrubicin), the vinca alkaloids (vincristine, vinblastine, vindesine and vinorelbine), taxanes (paclitaxel or taxol, and docetoxel or taxotere), epidopodophyllotoxins (etoposide or VP-16 and tenoposide), nelarabine and imatinib, or a pharmaceutically acceptable salt thereof, among others.

At the first onset of cancer or at the first indication that a patient is at risk for the occurrence or recurrence of cancer, for example because of the isolation and analysis of precancerous cells or other conditions which evidence that a precancerous condition may worsen into a cancer disease state or alternatively, metastasize to other tissue, an effective amount of at least one ABCB1 inhibitor as otherwise described herein is coadministered with at least one anticancer agent as described herein to treat the patient for a time and in a manner which is appropriate for avoiding the cancer or metastasis of the cancer and/or causing the cancer to go into remission or at least to extend the life of the patient. Although the present method may be used quite effectively to treat cancers which are drug resistant and especially those exhibiting multiple drug resistance, the present method is used to treat any cancer in order to reduce the likelihood that a cancer will develop drug resistance during treatment, reduce the likelihood that the cancer will recur and reduce the likelihood that should such cancer recur, that the recurring cancer is drug resistant or will exhibit multiple drug resistance.

Thus, the present compounds and compositions may be used quite effectively to treat cancers, especially those which are drug resistant or exhibit multiple drug resistance and which provide an exceptionally effective treatment modality to reduce the risk of occurrence, recurrence and/or metastasis of a cancer, especially a drug resistant cancer or a cancer which exhibits multiple drug resistance.

The invention also provides methods of treatment useful for treating diseases in which transporter proteins mediate the disease state in particular cancer, especially drug resistant (DR) and multiple drug resistant (MDR) cancer. The treatment of cancer, including the treating of various leukemias, especially T-lineage acute lymphoblastic leukemia, especially forms which are multiple drug resistant, are important features of the present invention. Pharmaceutical compositions which comprise novel pyrazolo[1,5-a]pyrimidine efflux inhibitors are also provided; in some embodiments these compositions include at least one additional anticancer agent, optionally in combination with a pharmaceutically acceptable carrier, additive or excipient.

The invention is described further in the following examples, which are illustrative and in no way limiting.

EXAMPLES

Example 1

Efflux Inhibitors with Varying Selectivity Toward ABCG2 Over ABCB1

Experimental Overview

Although many mechanisms exist, resistance of tumors to cancer therapy drugs is the principal reason for treatment failure and the majority of clinical and experimental data indicates that multidrug transporters such ABCB1 (Pgp, MDR1) and ABCG2 (BCRP, MRP1)) play a leading role by preventing cytotoxic intracellular drug concentrations. Inhibition of the function of these drug efflux pumps presents a promising approach to treat cancer using existing drugs. To date, clinical trials with such adjuvant therapies have been relatively unsuccessful. One likely contributing factor to these failed clinical applications is limited understanding of specific substrate/inhibitor/pump interactions. We have identified selective efflux inhibitors by profiling multiple ABC transporter efflux pumps against a library of small molecules could result in molecular probes that could further explore such interactions. Using JC-1 as a dual-pump fluorescent reporter substrate in our primary screening protocol we observed a piperazine substituted pyrazolo[1,5-a]pyrimidine substructure with promise for selective efflux inhibition. As a result of a focused structure activity relationship driven chemistry effort we describe below efflux inhibitors with varying selective toward ABCG2 over ABCB1. These compounds have low in vitro cellular toxicity, as well as adequate solubility and stability under appropriate experimental conditions. To our knowledge, low nanomolar chemoreversal activity coupled with direct evidence of efflux inhibition for ABCG2 inhibitors is unprecedented. The compounds also appear to have an IP landscape with space to operate. In vitro chemotherapeutic potentiation further illustrates the utility of the compounds and other related members. The scaffold and analogs show promise for extention into in vitro animal models. In fact, preliminary studies in our ABCG2 over-expressing tumor indicate that the at least two of the compounds significantly reduces tumor size in combination with the chemotherapeutic topotecan. Tumors that were grown for 4 weeks effectively disappeared by the fourth day of treatment.

Materials and Methods

General Information:

The ABCB1 over-expressing drug-resistant cell line, CCRF-Adr 5000, and itsparental CCRF-CEM cells were kindly provided by Dr. T. Efferth (Pharmaceutical Biology, German Cancer Research Center, Heidelberg, Germany). We have previously described the generation of the Jurkat-DNR ABCB1 over-expressing cell line.[60] We have also developed and previously characterized a SupT1-vincristine (Vin) drug-resistant cell line that selectively over-expresses ABCC1.[61] Ovarian Ig-MXP3(ABCG2) and its parental Igrov 1-sensitive cells were kindly provided by Dr. D. Ross (Department of Medicine, University of Maryland Greenebaum Cancer Center, Baltimore, Md.). Cells are grown in RPMI-1640 medium supplemented with 10% fetal bovine serum (FBS, Hyclone, Logan, Utah), 2 mM L-glutamine, 10 mM HEPES, 10 U/mL-penicillin, 10 µg/mLstreptomycin, and 4 µg/mLciprofloxacin. Selective pressure for the ABCB1 over-expressing CCRF-ADR 5000 and Jurkat-DNR cells is maintained by growth in 20 nMdaunorubicin (DNR). Selective pressure for the ABCG2 over-expressing Ig-MXP3 cells is maintained by treatment with 340 nMmitoxantrone (MTX) for 1 hr. prior to harvest. Selective pressure for the ABCC1 over-expressing SupT1-Vin cells is maintained by growth in 150 nM vincristine (Vin).

The fluorescent reporter dye JC-1 and cell type differentiation dye CellTrace™ Far Red DDAO-SE were obtained from Invitrogen™ (Eugene, Oreg.). Nicardipine hydrochloride, daunorubicin hydrochloride, mitoxantronedihydrochloride, vincristine sulfate, and Fumitremorgin C were purchased from Sigma-Aldrich (St. Louis, Mo.). XR9051, reversan, MK 571, and Ko 143 were purchased from Tocris Bioscience (St. Louis, Mo.). Compounds ordered for SAR by commerce were purchased from ChemDiv (San Diego, Calif.) and Ryan Scientific (Mt. Pleasant, S.C.). Unless otherwise indicated, all compound solutions were maintained and diluted in DMSO prior to addition to assay wells. Final DMSO concentrations were no more than 1% v/v. A Biomek® NX Multichannel (Beckman-Coulter, Fullerton, Calif.) was used for all cell and compound solution transfers for volumes greater than 1 µL. Low volume transfers (100 nL) were done via pintool (V&P Scientific, Inc., San Diego, Calif.). Compound dose response plates were generated with the Biomek® NX Span-8 (Beckman-Coulter, Fullerton, Calif.).

The HyperCyt® high throughput flow cytometry platform (IntelliCyt™, Albuquerque, N. Mex.) was used to sequentially sample cells from 384-well microplates (2 µL/sample) for flow cytometer presentation at a rate of 40 samples per minute.[62-63] Flow cytometric analysis was performed on a CyAn™ flow cytometer (Beckman-Coulter, Fullerton, Calif.). The resulting time-gated data files were analyzed with HyperView® software to determine compound activity in each well. Inhibition response curves were fitted by Prism® software (GraphPad Software, Inc., San Diego, Calif.) using nonlinear least-squares regression in a sigmoidal dose response model with variable slope, also known as the four-parameter logistic equation. This type of time-gated flow cytometric data analysis was described in detail for a previous ABC transporter screen from our group.[56]

$^1$H and $^{13}$C NMR spectra were recorded on a Bruker AM 400 spectrometer (operating at 400 and 101 MHz respectively) or Bruker AM 500 spectrometer (operating at 500 and 125 MHz respectively) in $CDCl_3$ with 0.03% TMS as an internal standard or DMSO-$d_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 mL/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3H-tetrafluoropropoxy) phosphazine; and a make-up solvent of 90:10:0.1 MeOH:Water:Formic Acid which was introduced to the LC flow prior to the source to assist ionization. The melting point was determined on a Stanford Research Systems OptiMelt apparatus.

Primary Assay:
Single Point, Duplex:

The assay is conducted in 384-well format microplates in a total volume of 15.1 µL dispensed sequentially as follows: 1) JC-1 substrate (10 µL/well); 2) test compound (100 nL/well); 3) drug-resistant cells (5 µL/well). CCRF-Adr cells (ABCB1) are color-coded with 0.5 ng/mLCellTrace™ Far Red DDAO-SE for 15 minutes at room temperature, washed twice by centrifugation, and then combined with unlabeled Ig-MXP3 cells (ABCG2) in the assay buffer. Final in-well concentration of test compound is 6.6 µM, JC-1 concentration is ~1 µM, and the cell concentration is 3×10$^6$ cells/mL (1:1 ratio of the two cell types). Nicardipine is used as an on plate control for both pumps at 50 µM. The plate contents are mixed, rotated end-over-end at 4 RPM and 25° C. for 10 minutes, and then cell samples are immediately analyzed. Approximately 2 µL volumes from each well are collected at a rate of approximately 40 samples per minute. This results in analysis of approximately 1,000 cells of each cell type from each well. Flow cytometric data of light scatter and fluorescence emission at 530+/−20 nm (488 nm excitation, FL1) and 665+/−10 nm (633 nm excitation, FL8) are collected.

Dose Response, Single-Plex:

The assay provider's ABCB1 over-expressing Jurkat-DNR cell line is used for confirmatory follow up instead of the CCRF-Adr cells. Each cell line (Jurkat-DNR and Ig-MXP3) is run separately against all compounds (no differential cell staining) in dose response. The assay is conducted in 384-well format in a total volume of 15.1 µL. Cells and reagents are added sequentially as follows: 1) PBS buffer (5 µL/well); 2) test compound (100 nL/well); 3) drug-resistant cells (10 µL/well) pre-stained with the JC-1 substrate at 1 µM. Final in-well concentrations of test compound range from 50 µM to 69 nM over an 18 point dose response and the cell concentration is 1×10$^6$ cells/mL. Nicardipine (50 µM) is added to each plate as a pan-inhibition positive control. The plate is rotated end-over-end at 4 RPM and 25° C. for 30 minutes and then cell samples are analyzed and flow cytometric data of light scatter and fluorescence emission at 530+/−20 nm (488 nm excitation, FL1) are collected.

Chemoreversal assay:

Cells (ABCB1, Jurkat-DNR or ABCG2 Ig-MXP3) are incubated with the test compound (3 order of magnitude concentration range) over a 3-day and 7-day period in the presence of the inhibitor and chemotherapeutic (ABCB1, DNR or ABCG2 MTX), such that a cell concentration of at least 1×10$^5$ cells/mL is maintained. Cell viability is determined by trypan blue staining and enumeration under light microscopy. At day 3, wells with greater than 2×10$^5$ cells are refreshed, to include readjustment of chemotherapeutic and inhibitor concentration. A chemoreversal index (Chemoreversal 50, $CR_{50}$) is determined from the viability assessment. Using a similar approach, a direct cytotoxicity index (Toxic Dose 50, $TD_{50}$) is determined by assessment of cell death of cells grown in media alone. Results are compared with the survival of parental cells in the presence of the selective agent (chemotherapeutic; 100% cell death), as well as survival of drug-resistant cells in the presence of the chemotherapeutic drug (control yields 100% viability). The difference between the $CR_{50}$ and the $TD_{50}$ give an approximation of the in vitro therapeutic index for the test compound.

In Vivo Animal Study Methods:
Model Design:

Specific-pathogen-free adult CB-17 female SCID mice (5-6 weeks of age) weighing 20-25 g, are purchased. Briefly, ABCG2 over-expressing Igrov1/T8 cells are injected (5×10$^6$ cells/mouse). Prior to injection, Igrov1/T8 cells are maintained in topotecan in order to assure continuous expression of ABCG2. Tumors are allowed to grow for 3-4 weeks or until tumor volumes are greater than ~100 cubic millimeters, at which time they are stratified into treatment groups. Treatment is administered and we observe the size of the tumor and weight of the mouse over a 7 day period. At the end of 7 days, we: 1) sacrifice the animal; 2) measure and weigh the tumor (if present); 3) analyze the histology of the tumor as well as other organs for evidence of toxicity; and 4) measure the expression of ABCG2 receptors on the tumor to determine if in vivo growth has altered ABCG2 expression. In our initial studies, we have generally observed high survival at 4 weeks (>90%) which escalates rapidly with near 100% mortality by 6 weeks. This approach is well described elsewhere.[9]

In the proposed experimentation, three groups of mice will be studied: 1) mice with Igrov11T8 tumors and injected with ABCG2 inhibitor; 2) mice with Igrov11T8 tumors that are sham injected; and 3) mice with parental cells that are not resistant to topotecan. In the first set of studies, we will determine the optimal dose of the ABCG2 inhibitor using primarily Group 1 mice. Using the in vitro cell killing data as a guide, we will test 6 doses of the ABCG2 inhibitor (SID 103911215) over 2 logs of final blood concentration (10 nM to 1 µM). In order to assure statistical significance, we will study 5 mice in each group. Results will be compared against one group of mice from Groups 2 and 3. The reduction of the size of the tumor will be used as the principal factor in determining the optimal dose, although toxicity will also be considered.

In the second set of studies, we will employ all three groups of mice using the optimal dose of ABCG2 inhibitor for Group 1. We will examine mice for overall survival at 6 weeks (including tumor size and body weight), acute toxicity due to the administration of the ABCG2 inhibitor, and tumors to make sure that the level of ABCG2 expression is not altered by in vivo growth.

Acute Toxicity:

Since prior information regarding the acute toxicity of the ABCG2 inhibitor is not available, body weight and histology of liver, kidneys, spleen, lungs, and heart will be obtained and analyzed. In addition to standard histologic stains, immunohistochemical stains to detect apoptosis will be obtained in order to compare organs and toxicity from sham and ABCG2 injected animals.

ABCG2 Expression by RT-PCR:

We will also measure the RNA expression of ABCG2 by RT-PCR in 10 tumors from treated and sham-injected mice in order to measure the effects of in vivo growth and treatment on the expression of ABCG2 in these tumors. Finally, we will perform limited toxicity studies and any acute toxicity leading to cell necrosis or other histologic change will be observed. Pharmacokinetic sampling and analysis will be performed in subsequent studies outside of this proposal.

Regulatory:

Mice will be studied and maintained in accordance with guidelines of our Institutional Animal Research Committee at UNM HSC. We have already obtained IACUC approval.

Figure 2:
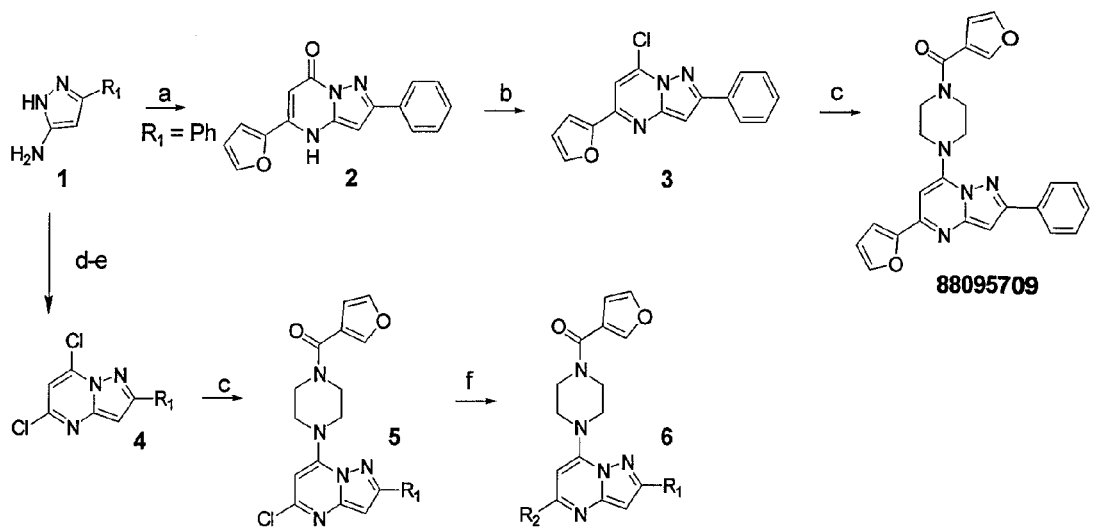
FIG. 2 illustrates a general synthetic route useful in making compounds of the invention.

Representative Synthesis and Chemical Characterization:

SID 88095709 and many analogues are synthesized by the method shown (sequence a-c, FIG. 2). Commercial or readily-obtained substituted aminopyrazoles 1 are treated with the appropriate dialkylmalonate or β-ketoester to give intermediate 2, followed by chlorination to afford the pyrazolo[1,5-a]pyrimidine core intermediate 3. Installation of the piperazine moiety afforded SID 88095709 compound directly. In some cases, a Suzuki or Molander type coupling was preferred to install aryl functionality at a late stage in the synthesis (see sequence d-f). With minor modification (including utilizing different starting materials and/or intermediates), the compounds according to the present invention are readily afforded.

5-(furan-2-yl)-2-phenylpyrazolo[1,5-a]pyrimidin-7(4H)-one(2)

A mixture of 3-phenyl-1H-pyrazol-5-amine (1: 0.318 g, 2.0 mmol, 1.0 eq) and methyl 3-(furan-2-yl)-3-oxopropanoate (0.370 g, 2.2 mmol, 1.10 eq) was heated in acetic acid (2.0 mL) at 100° C. for 4 hr. After cooling down to rt, the precipitate was collected by filtration. The precipitate was rinsed with EtOH (15 mL) and dried under air to afford 5-(furan-2-yl)-2-phenylpyrazolo[1,5-a]pyrimidin-7(4H)-one (0.358 g, 65%) as a white solid. $^1$H-NMR (400 MHz, DMSO-$d_6$) δ 12.70 (s, 1H), 8.06 (m, 1H), 8.00 (m, 1H), 7.98 (m, 1H), 7.51-7.47 (m, 3H), 7.44-7.42 (m, 1H), 6.81 (dd, J=3.7, 1.8 Hz, 1H), 6.64 (s, 1H), 6.15 (s, 1H).

7-chloro-5-(furan-2-yl)-2-phenylpyrazolo[1,5-a]pyrimidine (3)

A mixture of 5-(furan-2-yl)-2-phenylpyrazolo[1,5-a]pyrimidin-7(4H)-one (0.277 g, 1.0 mmol, 1.0 eq), POCl$_3$ (0.613 g, 4.0 mmol, 4.0 eq), N-benzyl-N,N,N-triethylethanaminium chloride (0.456 g, 2.0 mmol, 2.0 eq) and N,N-dimethylaniline (0.121 g, 1.0 mmol, 1.0 eq) in acetonitrile (5.0 mL) was heated at 80° C. for 4 hr. The completed reaction was diluted with CHCl$_3$ (20 mL), washed with H$_2$O (10 mL), and the separated organic layers were dried (MgSO$_4$) and concentrated. The residue was purified by chromatography (Biotage25 g, EtOAc/Hexane) to afford 7-chloro-5-(furan-2-yl)-2-phenylpyrazolo[1,5-a]pyrimidine (0.247 g, 84%) as a yellow solid. $^1$H-NMR (400 MHz, CDCl$_3$) δ 7.97-7.94 (m, 2H), 7.56 (m, 1H), 7.43-7.39 (m, 2H), 7.36-7.34 (m, 1H), 7.19 (s, 1H), 7.17 (dd, J=3.5, 0.5 Hz, 1H), 6.97 (s, 1H), 6.54 (dd, J=3.5, 1.7 Hz, 1H).

(4-(5-(furan-2-yl)-2-phenylpyrazolo[1,5-a]pyrimidin-7-yl)piperazin-1-yl)(furan-3-yl)methanone (SID 88095709)

A mixture of 7-chloro-5-(furan-2-yl)-2-phenylpyrazolo[1,5-a]pyrimidine (0.148 g, 0.5 mmol, 1.0 eq), furan-3-yl(piperazin-1-yl)methanone (0.180 g, 1.0 mmol, 2.0 eq,) and N-ethyl-N-isopropylpropan-2-amine (0.129 g, 1.0 mmol, 2.0 eq) in acetonitrile (5.0 mL) was heated at 100° C. for 3 hr. The completed reaction was purified by chromatography (Biotage 25 g, EtOAc/Hexane) to afford (4-(5-(furan-2-yl)-2-phenylpyrazolo[1,5-a]pyrimidin-7-yl)piperazin-1-yl)(furan-3-yl)methanone (0.218 g, 99%) as a white solid. $^1$H-NMR (400 MHz, CDCl$_3$) δ 8.03-8.00 (m, 2H), 7.83 (m, 1H), 7.62 (m, 1H), 7.52-7.47 (m, 3H), 7.45-7.41 (m, 1H), 7.23 (dd, J=3.5, 0.7 Hz, 1H), 6.93 (s, 1H), 6.65 (m, 1H), 6.62 (dd, J=3.5, 1.8 Hz, 1H), 6.60 (s, 1H), 4.08 (b, 4H), 3.92 (b, 4H). $^{13}$C NMR (125 MHz, CDCl$_3$) δ 164.1, 155.4, 152.4, 151.8, 150.1, 148.5, 144.3, 143.8, 143.2, 132.9, 129.0, 128.7, 126.4, 120.6, 112.6, 110.9, 110.1, 92.9, 88.9, 48.3. LCMS retention time: 3.20 min; purity at 215 nm=100%. HRMS m/z calculated for $C_{24}H_{27}N_5O_2$ ([M+H]$^+$): 440.1717. found 440.1715.

Solubility:

Aqueous solubility was measured in phosphate buffered saline (PBS) at room temperature (23° C.). PBS by definition is 137 mMNaCl, 2.7 mMKCl, 10 mM sodium phosphate dibasic, 2 mM potassium phosphate monobasic and a pH of 7.4. The solubility of SID 88095709 was determined to be 0.51 µg/mL.[64]

Applying a flow cytometrickinetic solubility protocol,[65] we were also able to compare solubility across primary, secondary, and profiling buffer conditions in house. This method evaluates precipitation as a function of side scatter changes (above thebuffer baseline); we observed 2 µg/mL solubility in PBS alone. This is approximately three fold higher than reported above; however, our protocol uses 1% DMSO as compared to 0.1%. Such changes in the concentration of DMSO can significantly increase overall solubility of a compound. The presence of fetal bovine serum also affects compound availability and in the primary assay screening buffer (6.7% FBS in PBS, 1% DSMO) the precipitation was inhibited slightly with no particulate noted at 3 µg/mL. The growth media indicated in the methods section (RPMI with 10% FBS, 1% DMSO) showed no precipitate forming at 6 µg/mL. It should also be noted that compounds with poor solubility at high concentrations (i.e. nicardipine above 50 µM) tend to show a response drop-off in the primary dose response conditions and this phenomenon was not significantly observed with the SID 88095709 or related compounds. In general, we are confident that compound availability is sufficient for the concentration ranges discussed for this scaffold set in our described biological systems.

Figure 3:
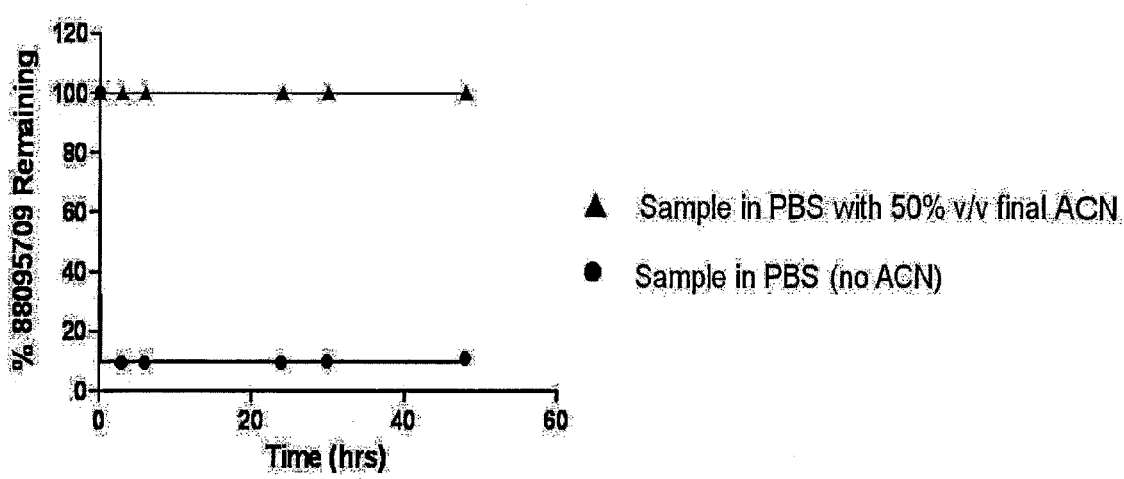
FIG. 3 depicts the aqueous stability of compound SID 88095709 in PBS and no acetonitrile (closed circles), and the aqueous stability of compound SID 88095709 in PBS with the addition of acetonitrile (50% v/v final, closed triangles). Reagents: (a) methyl 3-(furan-2-yl)-3-oxopropanoate, AcOH, 100° C., 2 h; (b) POCl3, BnEt3NCl, PhNMe2, CH3CN, 80° C., 16 h; (c) furan-3-yl(piperazin-1-yl)methanone, DIPEA, CH3CN, 100° C., 16 h; (d) diethylmalonate, 21% NaOEt, EtOH, 80° C., 3 h, 75%; (e) POCl3, N,N-dimethylaniline, 115° C., 16 h, 42%; (f) potassium aryltrifluoroborate salt, Pd(OAc)2, RuPhos, Na2CO3, EtOH, MWI, 90° C., 6 h.

Stability:

Aqueous stability was measured at room temperature (23° C.) in PBS (no antioxidants or other protectants and DMSO concentration below 0.1%). The stability of SID 88095709, determined as the percent of compound remaining after 48 hours, was 10%.[64] Stability data are depicted as a graph showing the loss of compound with time over a 48 hour period with a minimum of 6 time points and provide the percent remaining compound at end of the 48 hours (FIG. 3, closed circles).

It has been reported by several MLPCN partners and our collaborators at the Sanford-Burnham Institute who perform this assay, that the conditions for the stability assay as described above is fundamentally unreliable for compounds that exhibit moderate to poor aqueous solubility. Given the low solubility of SID 88095709 (0.51 µg/mL, reported in Section C above), the stability experiment was repeated with the addition of acetonitrile (50% v/v final) which has been reported to routinely resolve any contributions due to insolubility. The stability data under these conditions overlain in the FIG. 3 and is also depicted as a graph showing the loss of compound with time over a 48 hour period with a minimum of 6 time points and provide the percent remaining compound at end of the 48 hours (FIG. 3, closed triangles). The addition of acetonitrile appears to have solubilized the compound and provided a more accurate reading of the stability, which is now 100% remaining after 48 hours.

Results

Summary of Screening Results:

A total of 194,394 compounds were tested in the primary single point assay conditions with 200 and 130 actives noted in ABCB1 and ABCG2 respectively. Compounds were deemed active if the percent inhibition was greater than 80%. Activity was determined on the basis of the median fluorescence intensity (MFI) of JC-1. Percent inhibition was calculated as 100×[1−(MFI_PC−MFI Test)/(MFI_PC−MFI_NC)] in which MFI Test, MFI_PC and MFI_NC represent the MFI of cells in wells containing test compound, the average MFI of cells in positive control wells (maximum fluorescence intensity) and the average MFI of cells in negative control wells (minimum fluorescence intensity), respectively. The ACTIVITY_SCORE is equal to the calculated percent inhibition, except when percent inhibition is greater than 100 and less than 0.

A subsequent Small Molecule Repository cherry pick resulted in single point confirmatory testing of 273 compounds resulting in 18 and 16 actives in ABCB1 and ABCG2, respectively. Innate fluorescence of test compound was subtracted out based on MFI of unstained cells before calculation of percent inhibition of efflux pump activity. The following equations were used to calculate percent inhibition: % Inhibition=100×(FluorDelta_Sample−FluorDelta_NC)/(FluorDelta_PC−FluorDelta_NC) in which FluorDelta_Sample (FluorDelta=MFI_JC-1−MFI_non-JC-1 in which MFI_JC-1 are the MFI of cells in wells in the presence of JC-1 and MFI_non-JC-1 are the MFI of cells in wells without JC-1) are the differences of JC-1 minus non-JC-1 from wells with test compound, FluorDelta_NC are differences from negative control wells (cells with DMSO, minimum fluorescence intensity) and FluorDelta_PC are differences from nicardipine positive control wells. These dose response of % Inhibition data were fitted via GraphPad Prism to a sigmoidal dose response curve with variable hillslope:% Inhibition=Bottom+(Top-Bottom)/(1+10^((Log EC50-Log Cmpd)*HillSlope)) where Log Cmpd is the log of compound concentration in micromolar and Top-Bottom is the FIT—PERCENT_SPAN. Prism reports estimated values and fitted statistics for the four parameters (Bottom, Top, Hillslope and $EC_{50}$). Dose response fits assessed as decent were those with Residual square <0.5, Hillslope<5, Standard deviation of estimated Log $EC_{50}$<3, and standard deviation of top/estimate for top <0.5. Only the fits that passed this filter were reported. The activity score was calculated based on two weighted criteria; $EC_{50}$<10 micromolar and FIT—PERCENT_SPAN >20% by the following equation:Activity Score=75*($EC_{50}$Cutoff−$EC_{50}$)/$EC_{50}$Cutoff+25*(Span−SpanCutoff)/SpanCutoff. Active compounds have activity scores greater than 52, inactive compounds have scores less than 52. Values above 100 or below 0 were adjusted to 100 or 0 respectively.

Figure 4:
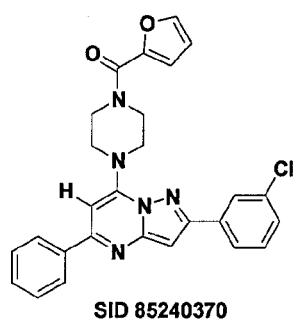
FIG. 4 shows that SID 85240370 had attractive efflux potency towards ABCG2 and marginal selectivity over ABCB1.

Structure Activity Relationship Information:

SAR by Commerce:

Limited SAR was revealed through the first round of cherry pick analysis, and about a third of the compounds were observed to be fluorescent artifacts. However, preliminary secondary screening efforts confirmed activity of several compounds including MLS000527783 (SID 17388272) with which micromolar potentiation and low toxicity was observed, but little pump specificity (data not shown). Resupply of this compound (new SID 85752814) confirmed the efflux inhibition, and a series of compounds similar in structure was ordered around this SMR hit. These 31 compounds were tested in dose response in two over-expressing cell lines: Jurkat-DNR (ABCB1) and Ig-MXP3 (ABCG2). Expansion of this piperazine substituted pyrazolo[1,5-a]pyrimidine substructure resulted in a selectivity profile significantly biased toward ABCG2. Of the hits that were identified through this commercial SAR endeavor, SID 85240370 had attractive efflux potency towards ABCG2 and marginal selectivity over ABCB1 (FIG. 4). The KU SCC launched an SAR campaign aimed at further understanding the origin of potency and selectivity and set out to optimize the compound profile to meet the appropriate criteria for potency (<1 µM) and selectivity (>10 fold) in the efflux assay. Compounds meeting these criteria were then screened in a subsequent chemoreversal assay, a cell killing secondary assay that shows potentiation of specific chemotherapeutics for each cell line as compared to the compound's inherent toxicity. The chemoreversal assays quantitatively show the potentiation of known killing agents for each cell line with efflux inhibitory compounds.

Chemoreversal potency criteria were set such that micromolar potentiation is desired and the $TD_{50}$/$CR_{50}$ ratio must be >10 with overall toxicity >15 µM. One compound was found to meet these secondary assay criteria for ABCB1, while 5 compounds matching this profile were identified for ABCG2. Structure activity relationships remained unclear at this stage. As compared to the efflux inhibition activity for SID 85240370, selectivity in the potentiation assay maintained a slight selectivity for ABCG2 with $CR_{50}$=0.14 µM vs. 0.70 µM in ABCB1. However, there was significant toxicity noted for both cell lines ($TD_{50}$=6.0 and 3.2 µM for ABCG2 and ABCB1 respectively). With these preliminary results in hand, an extensive SAR initiative was undertaken.

Figure 5:
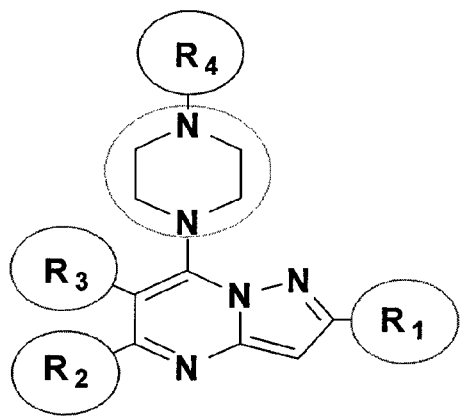
FIG. 5 illustrates how, in SAR studies, the pyrazolo[1,5-a]pyrimidine core was preserved, and the exchange of the peripheral substituents were surveyed, as depicted by the highlighted regions.

SAR by Synthesis:

A total of 165 compounds were assessed in the primary efflux assay and of these, 126 were synthesized by the KU SCC. A subset of compounds relating to the parent scaffold were purchased and assessed as part of the HTS effort at UNMCMD, prior to the KU SCC involvement. Of the ~30 commercial compounds assessed by the UNMCMD, a few showed modest ABCG2 selectivity (FIG. 4, SID 85240370), but gaps in the collection did not resolve the structural functionality responsible for any significant efflux potency or selectivity towards ABCG2 or ABCB1. Due to the diversity of structural changes present in the commercial set, additional compounds were needed to construct meaningful SAR, and this was done using the primary efflux data as it was more readily obtainable. The commercial set contained several members with conserved functionality that provided the basis for establishing a methodical SAR assessment. The pyrazolo[1,5-a]pyrimidine core was preserved, and exchange of the peripheral substituents were surveyed as depicted by the highlighted regions in FIG. 5. Several compounds of the purchased collection contained a 3-chlorophenyl substituent at R1, which also reflected the R1 moiety present in hit SID 85240370. As such, initially a series of compounds were prepared with these features maintained while adjusting R2-R4 (Table 1).

One compound cluster was constructed with R1-R3 groups identical to that of the parent hit SID 85240370 (entries 3-18) while modulating R4. Notably, the substitution of the acyl-2 furan for acyl-3-furan (entry 4) produced an enhancement in selectivity for ABCG2 (8.6-fold), predominately due to erosion of ABCB1 potency, while only modestly attenuating ABCG2 potency as compared to the parent hit. Improved ABCG2 potency was achieved with installation of an acyl-3-pyridine; however, the selectivity deteriorated essentially to pan inhibition (entry 13). Following incorporation of the acyl-3-furan as the more optimal R4 substituent, a survey was then done on the R2 group while holding constant R1 and R3 (entries 19-25). Substantial potency for ABCG2 was gained when R4 was 3-pyridine (entry 23); however, once again, selectivity was negatively impacted.

Alterations in the 3-chlorophenyl R1 substituent were then made while assessing several R4 head groups, specifically toggling between acyl-2-furan, acyl-3-furan, or benzoyl functionalities (entries 1-11, Table 2). No substantial improvements were noted with these changes; however, when R1 was changed from 3-chlorophenyl to phenyl, and R2 was varied (entries 12-18), it was discovered that a 2-furan at R2 in concert with the optimized acyl-3-furan afforded a significant boost in both ABCG2 potency as well as overall ABCG2 selectivity (entry 12, SID 88095709, ABCB1 $EC_{50}$=4.65 µM; ABCG2 $EC_{50}$=0.13 µM, selectivity=36 fold).

Figure 6:
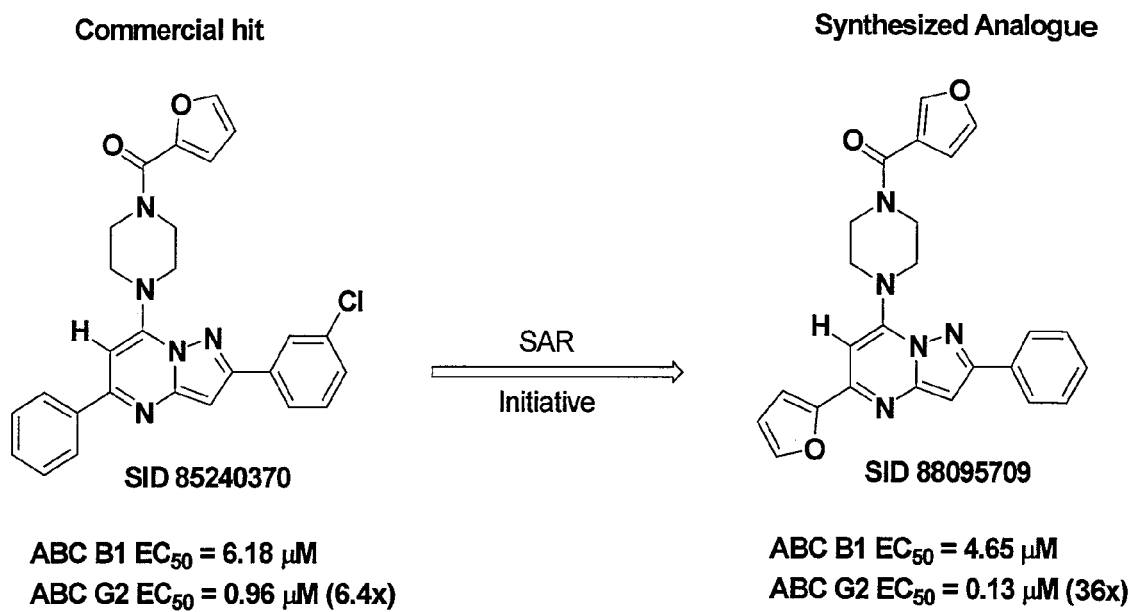
FIG. 6 illustrates SAR-based modification of parent hit SID 85240370 to a new lead, SID 88095709.

With this information in hand, the team followed up with an SAR effort aimed at demonstrating supportive SAR for compounds bearing an R2=2-furyl group while also attempting to improve upon the profile of the new lead, SID 88095709 (FIG. 6).

The new lead scaffold, represented by SID 88095709, was further studied by adjusting physiochemical and spatial elements in R1 (Table 3).

Switching out the phenyl ring of the lead with a t-butyl group erased much of the gains towards ABCG2 selectivity (entry 2, Table 3). Traditional phenyl replacements such as thiophene or furan were tolerated, but only led to modest selectivity and potencies. The installation of a 4-chlorophenyl substituent led to a reduced impact on ABCB1, resulting in selectivity in the efflux assay of 22-fold (entry 6); however, the change also marginalized the potency on ABCG2. Renovating the phenyl substituent with electron donating groups did not appear to be beneficial.

An examination of 2-furan replacements at R2 was also undertaken (Table 4). Simple alkyl units such as methyl or t-butyl degraded potency and fold-selectivity for both transporters. Notably, use of t-butyl actually reversed selectivity for ABCB1, albeit at the expense of potency (entry 5).

Some R2 revisions resulted in impressive ABCG2 selectivities and potencies. The choice of 2-F-phenyl (entry 10) slightly degraded potency for ABCB1 as compared to the parent (entry 1), leading to a 10-fold selectivity in favor of ABCG2. For the fluorinated series (entries 10-12), the potency for both transporters decreased as the fluorine atom was migrated from the 2- to 3- to 4-position of the aromatic R2 ring. Interestingly, the use of the use of a 3-MeO-phenyl group impeded potency for ABCB1 activity while retaining submicromolar ABCG2 potency on par with the parent, leading to an improved 83-fold selectivity between the transporters (entry 8). In this series (entries 7-9), however, a trend was not observed as the substituent was shifted from each position. Additional compounds prepared with the 3-MeO-phenyl group at R2 did not show a consistent SAR (data not shown).

Figure 7:
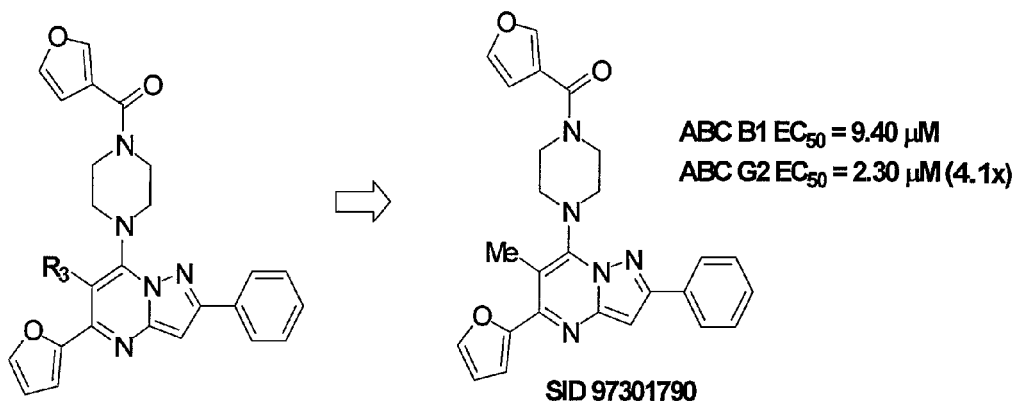
FIG. 7 illustrates the effect of $R_3$ alkyl substitution on compounds of the invention.

The commercial set of compounds contained a few scaffolds bearing a methyl group at R3. SAR generated in the early phases demonstrated some benefit to the presence of small alkyl groups at R3; however, this was highly dependent on the identity of groups at R1, R2 and R4. For the purposes of expanding the SAR around SID 88095709, one analogue was prepared to quickly evaluate the effect of this substitution pattern in concert with our chosen functionalities at R1, R2 and R4 (FIG. 7). ABCB1 potency was encouragingly impaired, but not without also effecting G2, resulting in a marginal selectivity profile.

Attention was then turned to investigating the effect of different R4 functionality appended to the piperazine (Table 5). In earlier SAR sets, activity was found to be sensitive to the identity of R4 and the pairing of groups at R2 and R3. In the context of our new lead, SID 88095709, we wanted to better understand the effect of R4 with the chosen substituents. It was confirmed that an acyl-3-furan was preferred to an acyl-2-furan (entry 2), and simple alkyl substitution of the 3-furan (entries 5-7) or a larger benzofuran (entry 8), while tolerated, did not reveal any benefits. However, the most influential effects on ABCB1 were observed when the acyl furan was exchanged for abenzyl ester (entry 11). While ABCG2 potency was compromised compared to the lead, ABCB1 potency was completely lost, yielding a selectivity of ~19 fold. In a more aggressive effort, the entire "top piece" of the scaffold, consisting of the piperazine and the R4 group, was modified (Table 6). Ring-opened piperazine equivalents, truncated amino groups, piperidine amides, ring-expanded amines (not shown) and various structural variations on a theme did not produce a profile superior to that which had already been observed.

In the process of evaluating these structural modifications, several compounds were prepared singly to target possible oversights in SAR, as every possible R1-R4 combination cannot be prepared and assessed in a timely way. Others were targeted as a means of inserting the best combinations as gleaned from the preceding generations of SAR. These compounds were more recently pursued for specific structural combinations summarized in Table 7. Data obtained early on had indicated that the acetyl group at R4 was more advantageous than other changes that had been surveyed (including the benzyl ester modification), though later refinement of these data does not now stand out as particular SAR of interest. Based on the information in hand at the time, substituted phenyl derivatives possessing a disparate electronic nature at R1 were incorporated with the acetyl R4 group in place (entries 2 and 3). No advantages were found.

We were interested in also surveying the effect of reducing the carbonyl of the R4 head group to give an amine in place of the amide when some of the preferred R1-R3 substituents were incorporated (entry 4) and, as an experimental one-off compound, in other pockets of SAR that seemed to be unrelated but were still interesting (entry 6). While the effect did not enhance the profile in the case of the most closely related analogue to the lead SID 88095709 (entry 4, SID 99376134), a profound effect was observed for the alternatively substituted compound with SID 97301789 (entry 6). As previously mentioned, the combination of R1-R4 has been found to radically influence the profile of the compounds towards ABCB1 or ABCG2. For example, methylation at R2 and R3 in concert with previously surveyed R1 and R4 moieties delivered an analogue which amounts to pan inhibition (entry 5). The combination effect cannot be underestimated, as shown with entry 6, in which methylation at R2 and R3, in concert with the newly discovered R4 head group of $CH_2$-3-furan, led to a 233-fold selectivity for G2 with comparable potency to the lead compound and abolished activity for ABCB1 in the efflux assay! The improved selectivity observed with the $CH_2$-3-furan in the R4 position could be due to a number of effects. Removal of the carbonyl of the parental acyl-3-furan R4 group confers basicity to the head group that was previously missing. Removal of the carbonyl also changes the conformation of the R4 group in relation of the piperidine ring ($sp^a$ hybridization) versus when the amide of the parent is intact ($sp^2$ hybridization). Although these aspects are likely not the only contributors to the observed benefits in selectivity, as a previously screened benzyl R4 group did not result in analogous improvements. Still, these effects are advantageous only when put in play with a select group of R1-R3 substitutions.

Figure 8:
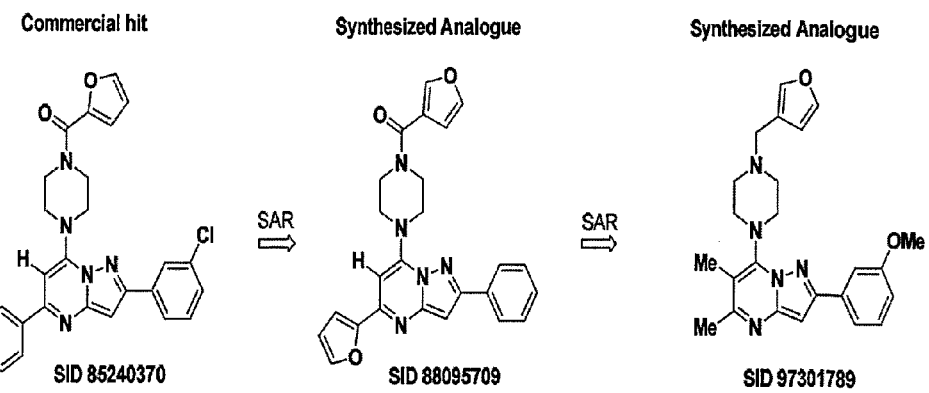
FIG. 8 depicts refinement of structure based on efflux and associated potentiation and toxicity data.
Figure 9:
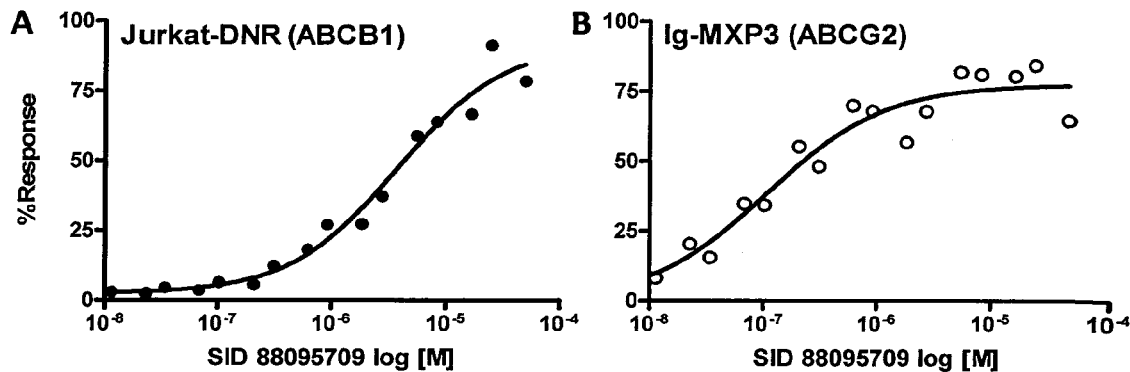
FIG. 9 illustrates efflux inhibition and chemotherapeutic potentiation of SID 88095709. 9A) A representative curve showing efflux inhibition of ABCB1 in Jurkat-DNR cells (closed circles). The average IC$_{50}$ (n=3) is 4.7±0.5 µM. 9B) A representative curve showing efflux inhibition of ABCG2 in Ig-MXP3 cells (open circles). The average IC$_{50}$ (n=2) is 0.13±0.30 µM. 9C) Potentiation of DNR mediated killing in Jurkat-DNR cells with SID 88095709 (n=2 per data point). The CR$_{50}$ (closed triangles) is 0.55 µM while the TD$_{50}$ (closed squares) is 5.5 µM. Minimum allowable toxicity is set at 15 thus the toxicity here is below the cut-off. 9D) Potentiation of MTX mediated killing in Ig-MXP3 cells (n=2 per data point). The CR$_{50}$ (open triangles) is 0.31 µM while the TD$_{50}$ (open squares) is 18.3 µM. The minimum toxicity and the CR$_{50}$/TD$_{50}$ ratio (equal to 59) meet the cut-off criteria for a desirable compound in the chemoreversal secondary ABCG2 assay.

In parallel to the above efforts, compounds were also assessed in potentiation secondary assays and associated data are presented in the preceding tables; however, the chemoreversal assay is a very low throughput assay and compound data from this assay could not be used to drive the SAR program. Key data have been collected for some of the most promising compounds (FIG. 8). Evaluation of SID 88095709 shows submicromolar ABCG2 efflux inhibition activity with ~36-fold selectivity toward ABCG2 over ABCB1. Potent submicromolar activity has also been demonstrated in the potentiated killing of both over-expressing cell lines with preference for ABCG2 from a toxicity perspective, though the degree of selectivity observed in the cell killing assay is removed (1.8 fold in chemoreversal vs. 36-fold in efflux assay). The most recently advanced analogue, SID 97301789, presents as an exceedingly potent compound in the potentiation assays with a 4.5-fold window between the observed potencies for the two transporters, but in favor of ABCB1. Interestingly, the analogue appears to be devoid of toxicity (>100 µM) and represents a promising tool for further refinement.

Figure 10:
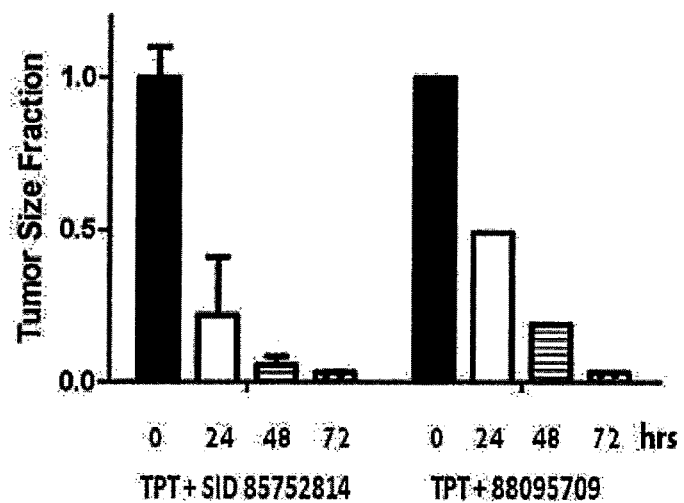
FIG. 10 depicts the response of ABCG2 resistant tumors in mice to combination therapy of TPT and ABCG2 inhibitors. The tumor size at 0, 24, 48, and 72 hours is indicated.

In Vivo Data:

To specifically demonstrate the effects of the drugs with our approach, we administered by IP injection a dose of TPT (150 nM in 75 µL) that results in the killing of parental cells, but not the resistant Igrov1/T8 cells ($EC_{50}$ for parental cells is 7 nM vs. 311 nM for resistant cells). To demonstrate efficacy of the inhibitors, we grew ABCG2 resistant cells in mice for 28 days. Tumor-bearing mice were injected with either 150 nM TPT, 100 nM SID 88095709 (probe resupply), or 500 nM SID 85752814 (original SMR hit). Tumor size remained the same or increased in each case. In contrast, injecting a combination of 150 nM TPT and 100 nM of SID 88095709 or 500 nM of SID 85752814 dramatically reduced tumor size and eliminated evidence of tumor within 2 to 3 days (FIG. 10), indicating that tumor sensitivity to TPT returned when one of the ABCG2-blocking compounds was present.

Scaffold/Moiety Chemical Liabilities:

The pyrazolo[1,5-a]pyrimidine scaffold and its derivatives have been easily handled in terms of stability to reaction conditions, exposure to acid or base, heating, and general manipulation. Most are isolated as stable solid materials. We have not observed decomposition nor have we experienced any chemical liability with these compounds. The structure does not contain moieties that are known generally to be reactive. Stability assessment was performed in 1×PBS buffer at pH 7.4 and room temperature. After 48 hours, it was determined that only 10 percent of the parent compound remained when the experiment was performed in PBS buffer alone, thus possibly indicating some structural liability that at this point in time is unknown. However, as previously mentioned, the stability assay used with PBS alone is likely not suitable for compounds with lower solubility. The experiment was repeated with acetonitrile to help solubilize the compound, leading to a favorable profile in which 100% of the sample was remaining after 48 hours and indicating no loss of integrity. Comparative assessment of the solubility in multiple assay conditions indicates moderate solubility; however this does not appear to be an issue for either primary or secondary screening protocols based both on direct observation of activity as well as the flow based experimentation briefly described above.

Kinase Profiling of SID 88095709:

Since ABC transporters are ATP dependent efflux pumps and several kinase targets have been implicated in the patent literature with structurally similar scaffolds, SID 88095709 was profiled against 50 kinases at a single concentration of 10 µM to assess promiscuity of the chemotype.[66] SID 88095709 was dissolved in DMSO and tested at a final concentration of 10 µM. Prior to initiating a profiling campaign, the compound was evaluated for false positive against split-luciferase. Profiling was done in duplicate for SID 88095709 against each kinase. The Percent Inhibition and Percent Activity Remaining are calculated using the following equation:

% Inhibition=$ALU$Control−$ALU$Sample×100 $ALU$-Control

% Activity Remaining=100−% Inhibition

The team has also submitted SID 88095709 and the analog SID 97301789 to the NIH National Cancer Institute to elucidate the effect of SID 88095709 on the cancer cell line panel.

Discussion

ABCB1, ABCC1, and ABCG2 transporters are known to significantly influence the ADME-Tox properties of drugs,[4] and although a large number of compounds have been identified possessing ABC transporter inhibitory properties, only a few of these agents are appropriate candidates for clinical use as MDR reversing agents.[67] Clinical trials with late generation modulators (e.g. biricodar, zosuquidar, dofequidar, and laniquidar) specifically developed for MDR reversal are ongoing.[38,41,68] Efflux pumps are by design highly adaptive and potentially able to adjust to a wide array of chemotypes owing to a relatively large cavity (~6000 Å$^3$) and at least three non-overlapping binding site configurations.[13] For example, rhodamine 123 has been used in combination with Hoechst 33342 to describe two functional transport sites in ABCB1 with complex allosteric interactions.[69]Concurrently, rhodamine 123 may bind to a different overlapping region, or potentially within the same large flexible binding site, as LDS 751.[70] It has also been shown that ABCB1 possesses two allosterically coupled drug acceptor sites where one binds vinblastine, doxorubucin, etoposide and cyclosporin A, and the other binds dexniguldipine and other 1,4-dihydropyridines.[71] It is thus possible that within a single chemical sub-structure class there could be multiple binding patterns leading to both the difficulty of direct structure activity relationship comparisons but also to the possibility of a tuneable synthetic system allowing selectivity and/or cross-transporter inhibition. It should be noted, however, that acquired mutations in transporter genes introduce even more complexity, altering the pattern of resistance and improving the ability of the mutants to efflux new drugs.[72] It was reported that various drug-selected human tumor cell lines expressed different ABCG2 variants, which were suggested to be gain-of-function mutations acquired during the course of drug exposure.[73] Single amino-acid changes cause an altered drug resistance profile and substrate specificity compared to the wild type ABCG2 transporter.[74] The lesson to be learned is that high efficacy and good selectivity need to be carefully compared in analogous systems and cell lines. This is readily apparent in the discrepant activity seen with FTC and Ko 143 (discussed below).

FIG. 11 summarizes the prior art comparison to SID 88095709, 85752814, and 97301789. XR9051 and MK571 were chosen to verify ABCB1 activity and counterscreen ABCC1 activity, respectively in our system. XR9051 does inhibit the efflux of JC-1 in both ABCB1 and ABCG2 overexpressing cell lines (0.6 and 2.3 µM respectivly). Potentiation data indicatessubmicromolar chemoreversal in both Jurkat-DNR and Ig-MXP3 cells with a bias toward ABCB1 at 10 nM as compared to 700 nM for ABCG2. Not surprisingly, we didn't observe any inhibition in ABCB1 or ABCG2 with MK571 but we remain interested in the MK571 response in ABCC1 over-expressing SupT1-Vin cells. It is likely that the "potentiation" seen with MK571 is simply due to general toxicity since in both cell lines the $CR_{50}$ is equivalent to the $TD_{50}$ (curves not shown).

Direct comparison of reversan in our efflux inhibition system shows low micromolar inhibition of both ABCB1 and ABCG2 (4.4 and 0.8 µM respectively) with moderate selectivity for ABCG2. In our chemoreversal potentiation assay, reversan showed micromolar activity and no apparent selectivity (2.2 and 3.6 µM in ABCB1 and ABCG2, respectively). This was coupled with significant toxicity in the Jurkat-DNR cell line. FTC showed no activity in either cell line in the efflux inhibition assay (data not shown) and was not tested in the potentiation assay. Ko 143 has been shown to potentiate mitoxantrone (MTX) at nanomolar levels in ABCG2 overexpressing cells.[11] In our potentiation assay there actually seemed to be a selectivity for ABCB1 over ABCG2 ($CR_{50}$=1.0 and 5.9 M respectively) with considerable toxicity in both cell lines. The efflux inhibition activity did not mirror this, showing no activity in ABCB1 and only 13.6 µM inhibition in ABCG2, potentially indicating a binding site difference versus JC-1.

The entire SAR series was also structurally compared via PLS analysis to the inhibitors described in FIG. 11 as well as the clinically relevant potentiators; Cyclosporin A, Biricodar, Tariquidar, Zosuquidar, Elacridar, Laniquidar, Dofequidar, and ONT093. The eight biological parameters listed in Table 1 have been used as dependent variables in the Y block of the PLS analysis which was performed. They included the normalized percent response and $IC_{50}$ values in the primary assay, and the $CR_{50}$ values in the secondary assay for both ABCB1 and ABCG2 transporters, and also the associated toxicity $TD_{50}$ data for these two targets. The goal of this analysis was not only to cluster the compounds in the physicochemical molecular descriptors space, but also to map these biological parameters and selected physicochemical parameters (computed solubility, log D7.4, MW, hydrogen bond donors and acceptors, etc) in the principal components space.

Figure 12:
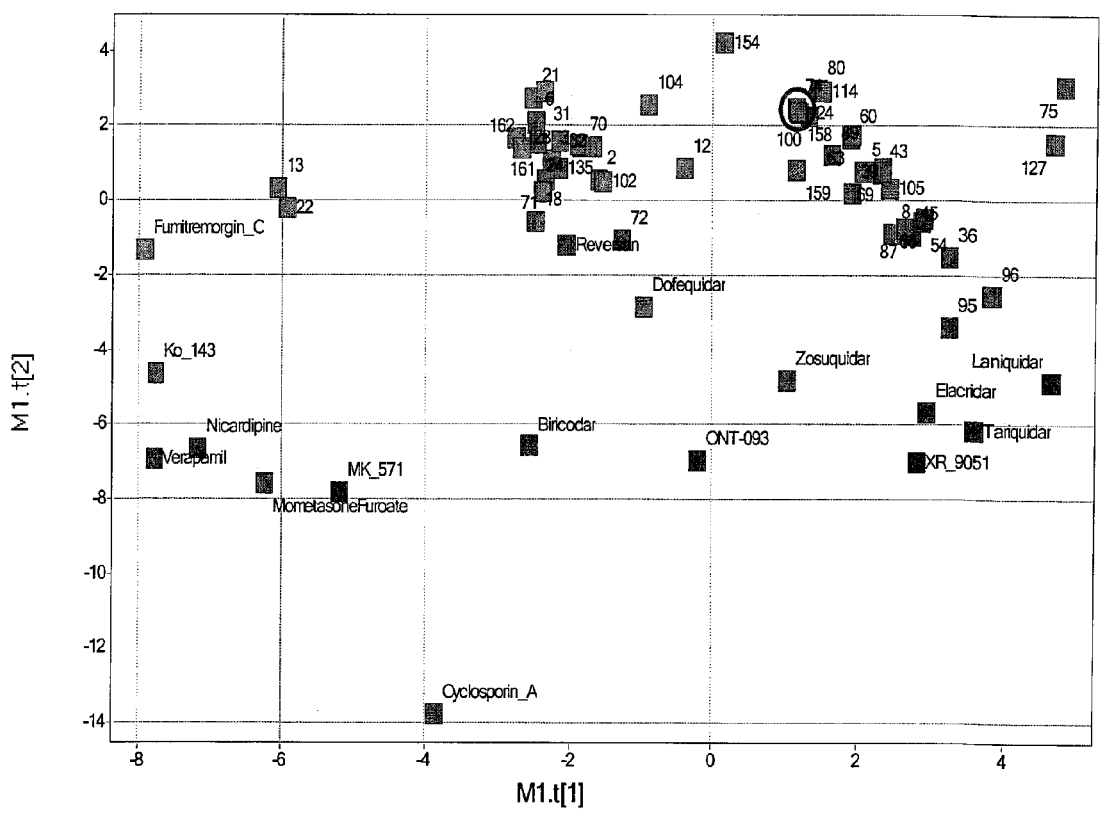
FIG. 12 is a map of the computed solubility of selected compounds in the PLS principal component space. Only prior art compounds and compounds tested in the secondary assays have been included. Most of the newly synthesized compounds show higher computed solubility (green) than prior art compounds which show a low one (red). SID 88095709 is marked with a red circle.
Figure 13:
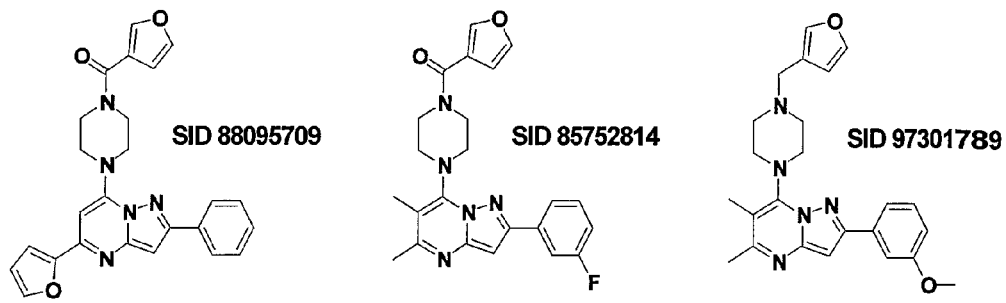
FIG. 13 (data on page 1 of disclosure) presents SAR data for SID 88095709, SID 85752814, and SID 97301789.
Figure 14:
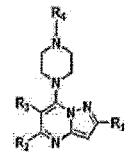
FIG. 14 shows Table 1, which summarizes SAR expansion on initial hit SID 85240370.
Figure 17:
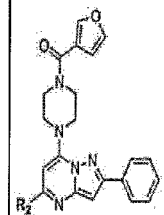
FIG. 17 shows Table 4, which summarizes a series of modifications of formula (I) variable $R_2$.
Figure 22:
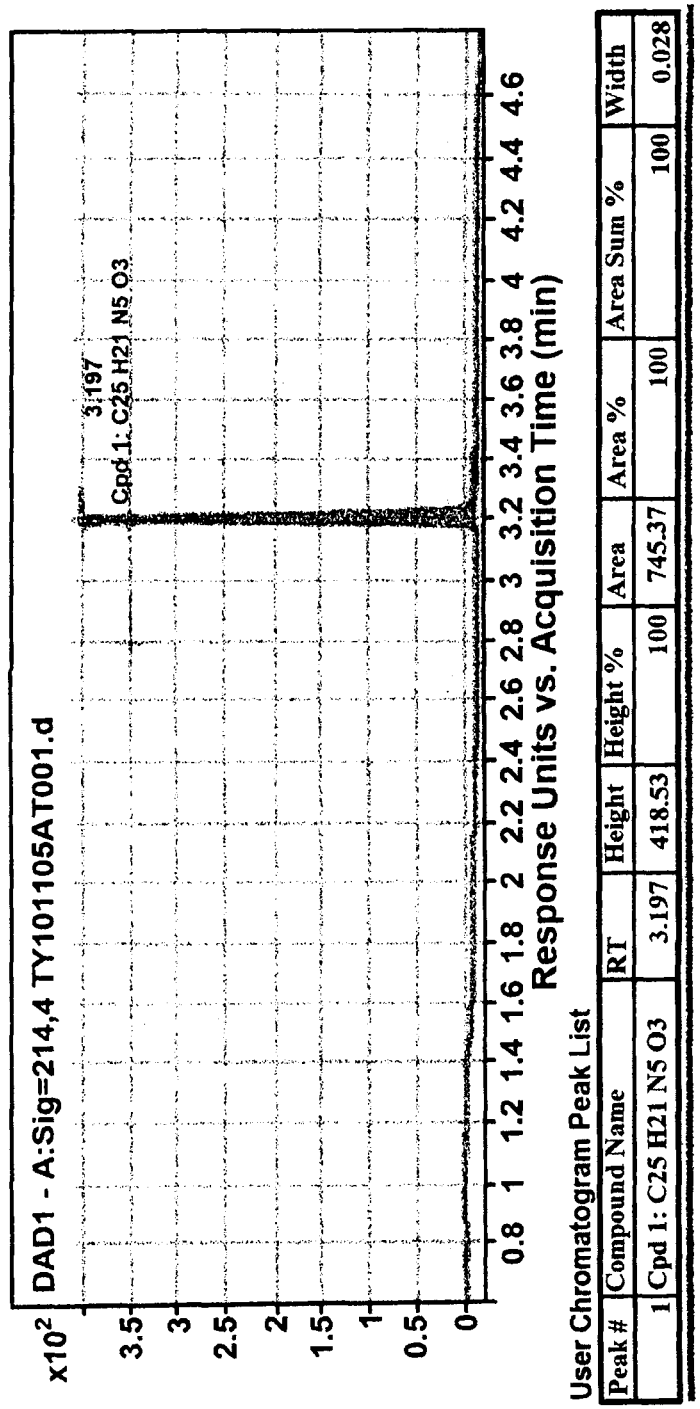
FIG. 22 illustrates LCMS purity data at 215 nm for SID 88095709; LCMS retention time: 3.20 min; purity at 215 nm=100%.
Figure 23:
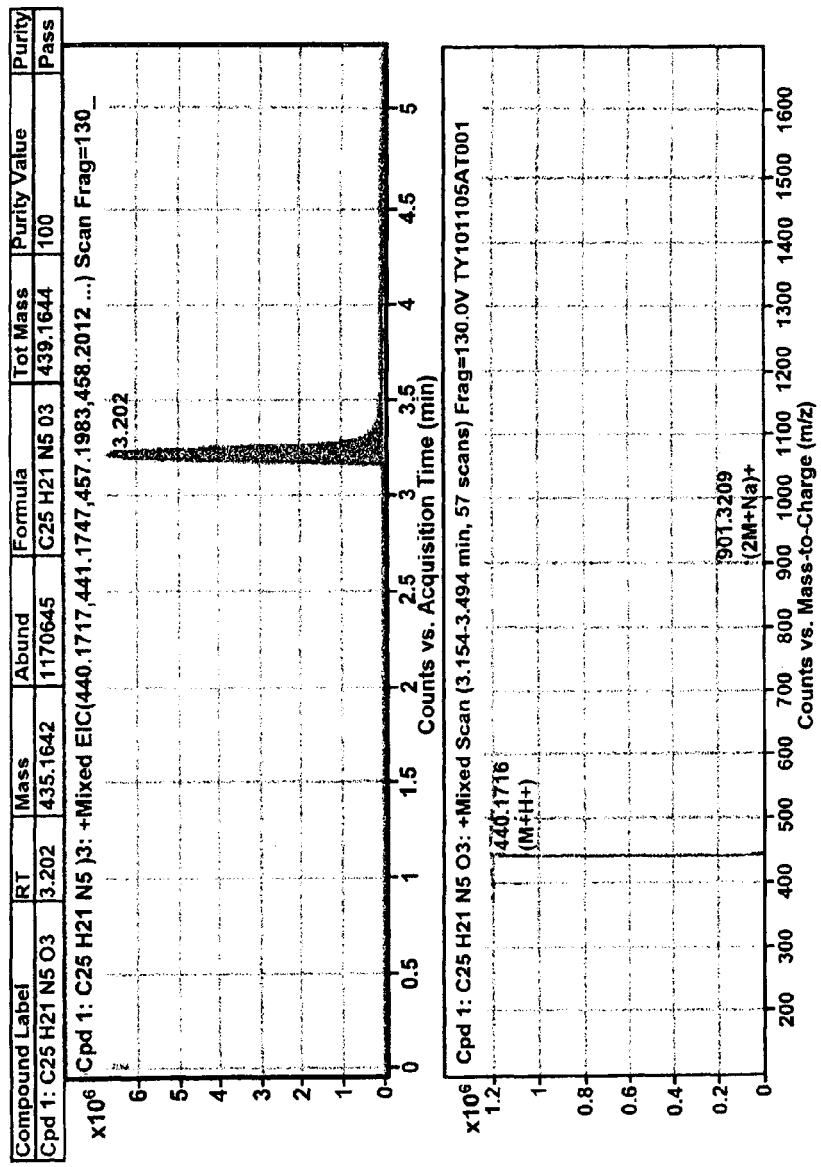
FIG. 23 shows HRMS data for SID 88095709; HRMS m/z calculated for $C_{25}H_{22}N_5O_3$ [M$^+$+H]: 440.1717. found 440.1715.
Figure 24:
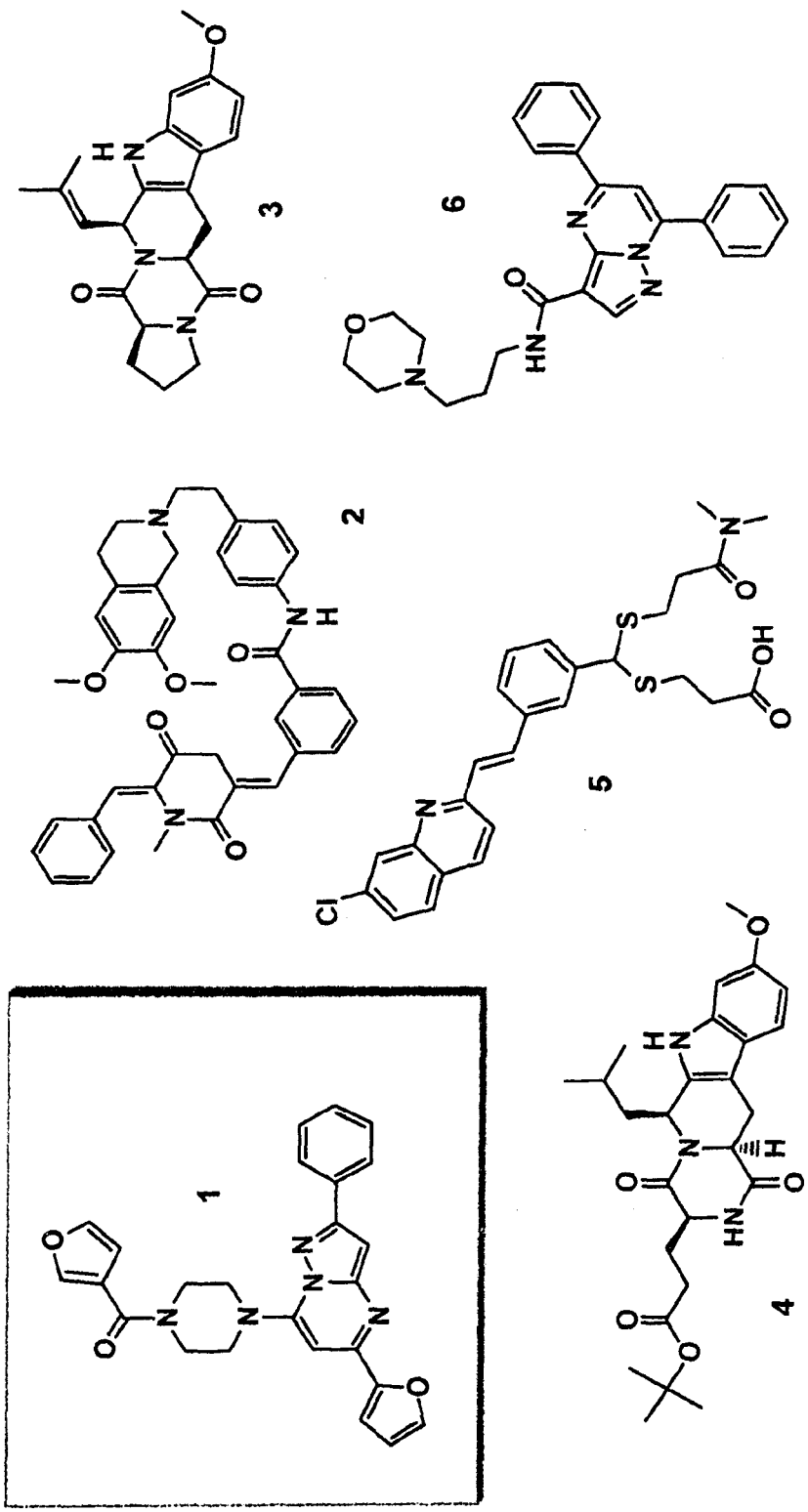
FIG. 24 (Example 2). Structures of small molecules chosen for direct experimental comparison. Probe compound CID44640177 (1), ABCB1 inhibitor XR9051 (2), ABCG2 inhibitors FTC (3) and Ko143 (4), ABCC1 inhibitor MK571 (5), and the pyrazolopyrimidine reversan (6).
Figure 25:
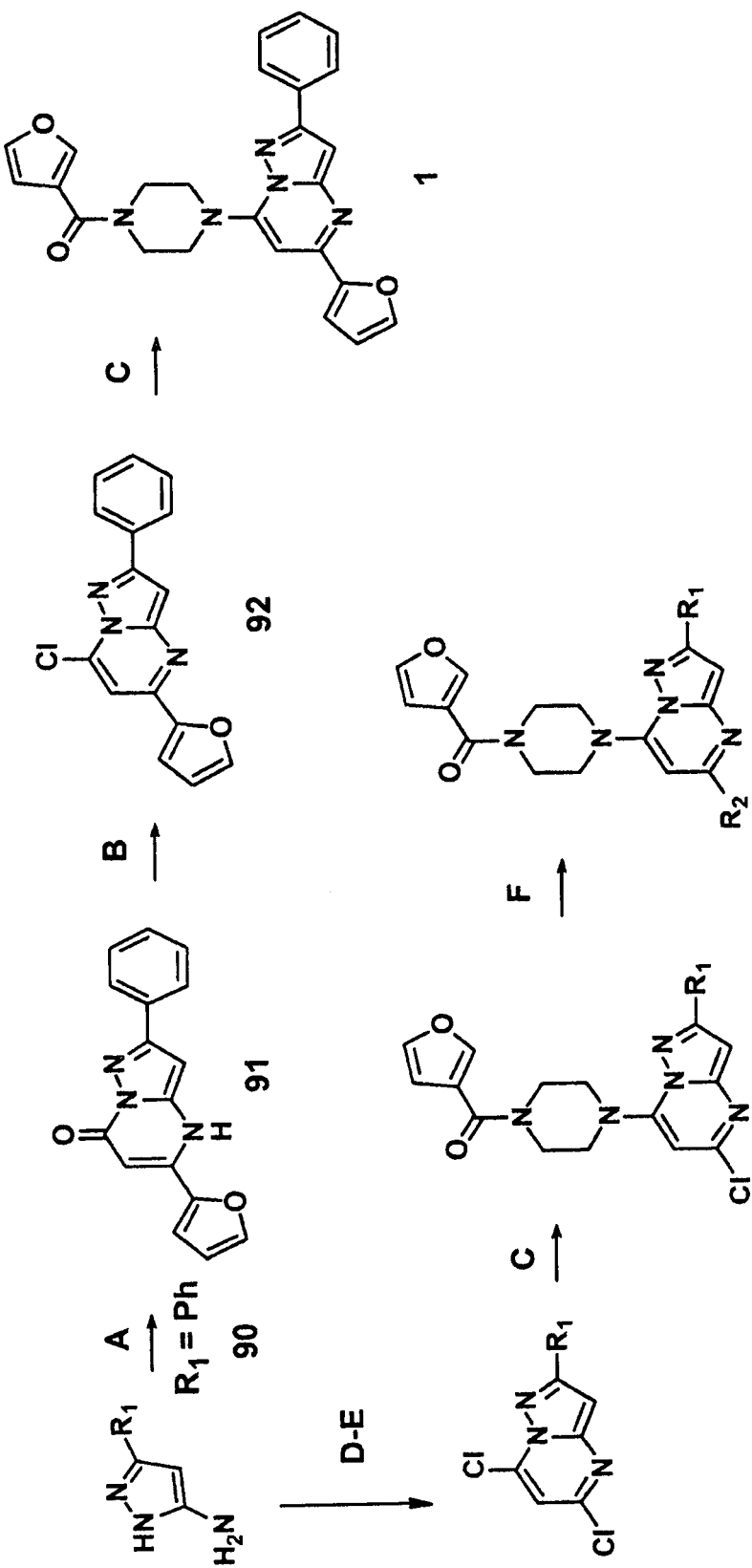
FIG. 25 (Example 2). Representative synthetic route for compound 1. (A) methyl 3-(furan-2-yl)-3-oxopropanoate, AcOH, 100° C., 2 hr (65% yield). (B) POCl$_3$, BnEt$_3$NCl, PhNMe$_2$, CH$_3$CN, 80° C., 16 hr (84% yield). (C) furan-3-yl(piperazin-1-yl)methanone, DIPEA, CH$_3$CN, 100° C., 16 hr (99% yield). (D) diethylmalonate (21% yield) NaOEt, EtOH, 80° C., 3 hr (75% yield). (E) POCl$_3$, N,N-dimethylaniline, 115° C., 16 hr (42% yield). (F) potassium aryltrifluoroborate salt, Pd(OAc)$_2$, RuPhos, Na$_2$CO$_3$, EtOH, MWI, 90° C., 6 hr.
Figure 27:
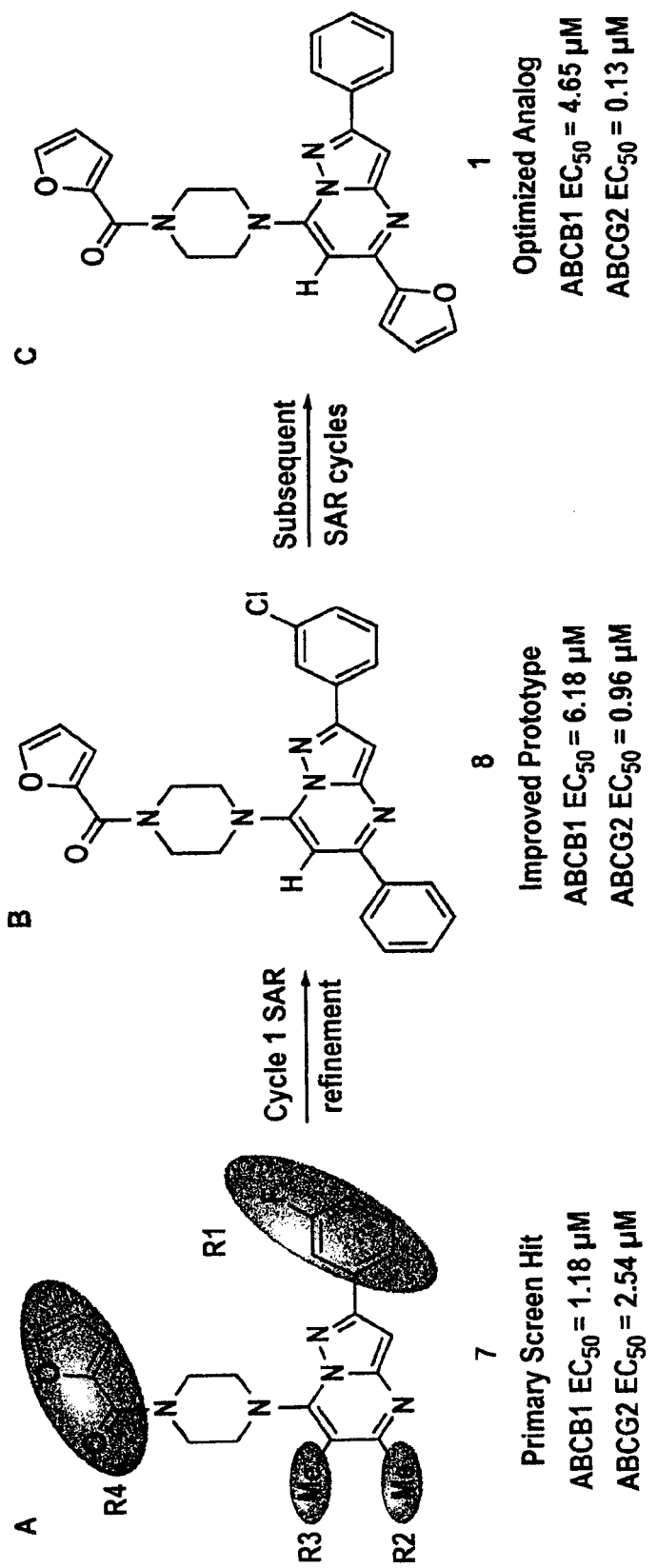
FIG. 27 (Example 2). Scaffold modification summary from primary hit to probe compound. (A) Screening hit compound 7 (CID1434724) and regions of targeted SAR optimization (shaded areas). (B) Compound 8 (CID1441553) obtained from first-generation SAR optimization. (C) SAR refinement of ABCG2 selectivity leading to compound 1 (CID44640177).
Figure 28:
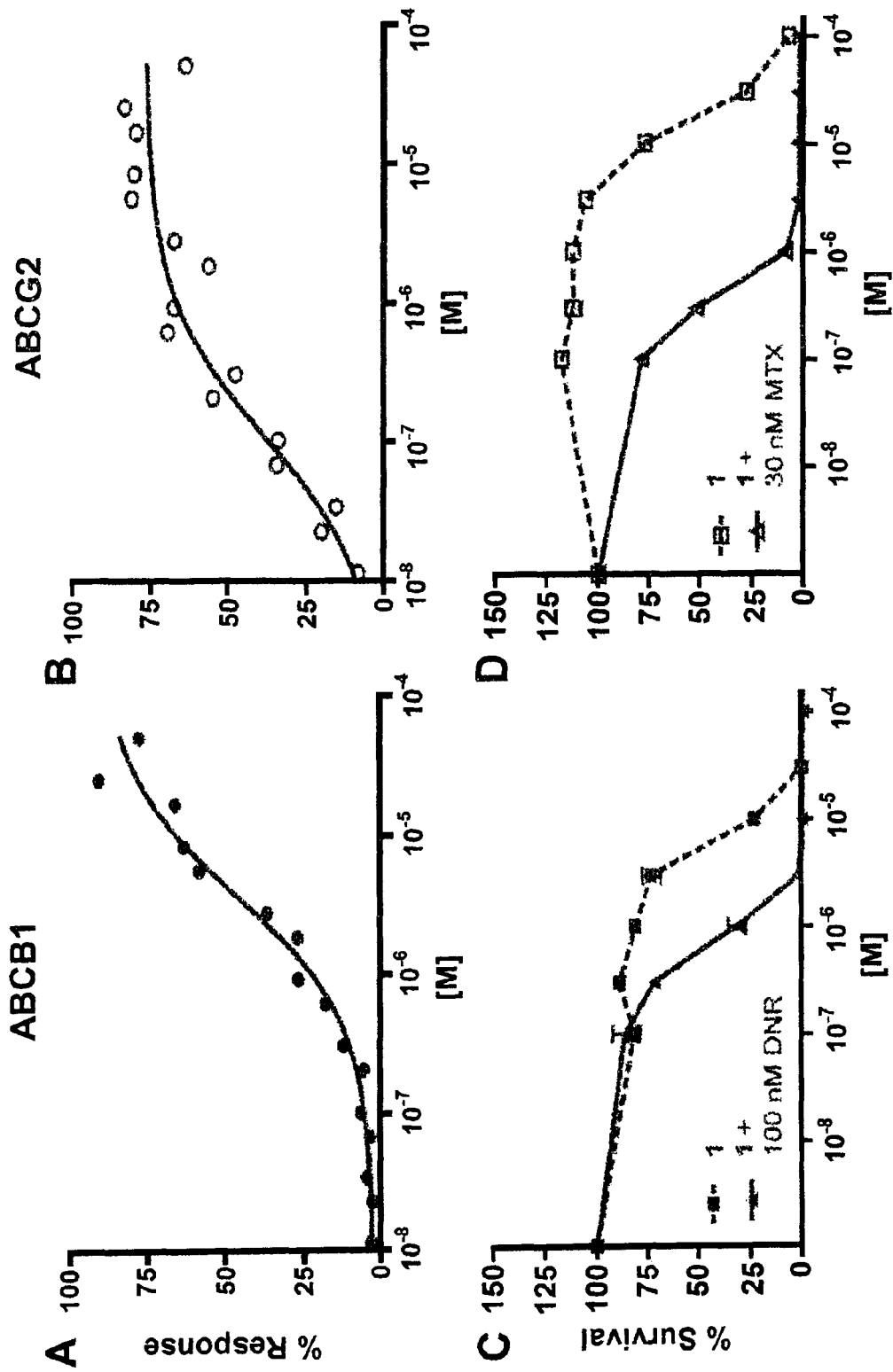
FIG. 28 (Example 2). Efflux inhibition and chemotherapeutic potentiation of 1 (CID 44640177). (28A) A representative curve showing efflux inhibition of ABCB1 in Jurkat-DNR cells (closed circles). The average $IC_{50}$ (n=3) is 4.65±0.74 µM. (28B) A representative curve showing efflux inhibition of ABCG2 in Ig-MXP3 cells (open circles). The average $IC_{50}$ (n=2) is 0.13±0.03 µM (28C) Potentiation of daunorubicin (DNR) mediated killing in Jurkat-DNR cells with 1 (n=2 per data point). The $CR_{50}$ (closed triangles) is 0.55 µM while the $TD_{50}$ (closed squares) is 5.52 µM. Minimum allowable toxicity is set at 15 µM, thus the toxicity here is below the cut-off. (28D) Potentiation of mitoxantrone (MTX) mediated killing in Ig-MXP3 cells (n=2 per data point). The $CR_{50}$ (open triangles) is 0.31 µM while the $TD_{50}$ (open squares) is 18.30 µM. The minimum toxicity and the $CR_{50}/TD_{50}$ ratio (equal to 59) meet the cut-off criteria for a desirable compound in the chemoreversal secondary ABCG2 assay.
Figure 29:
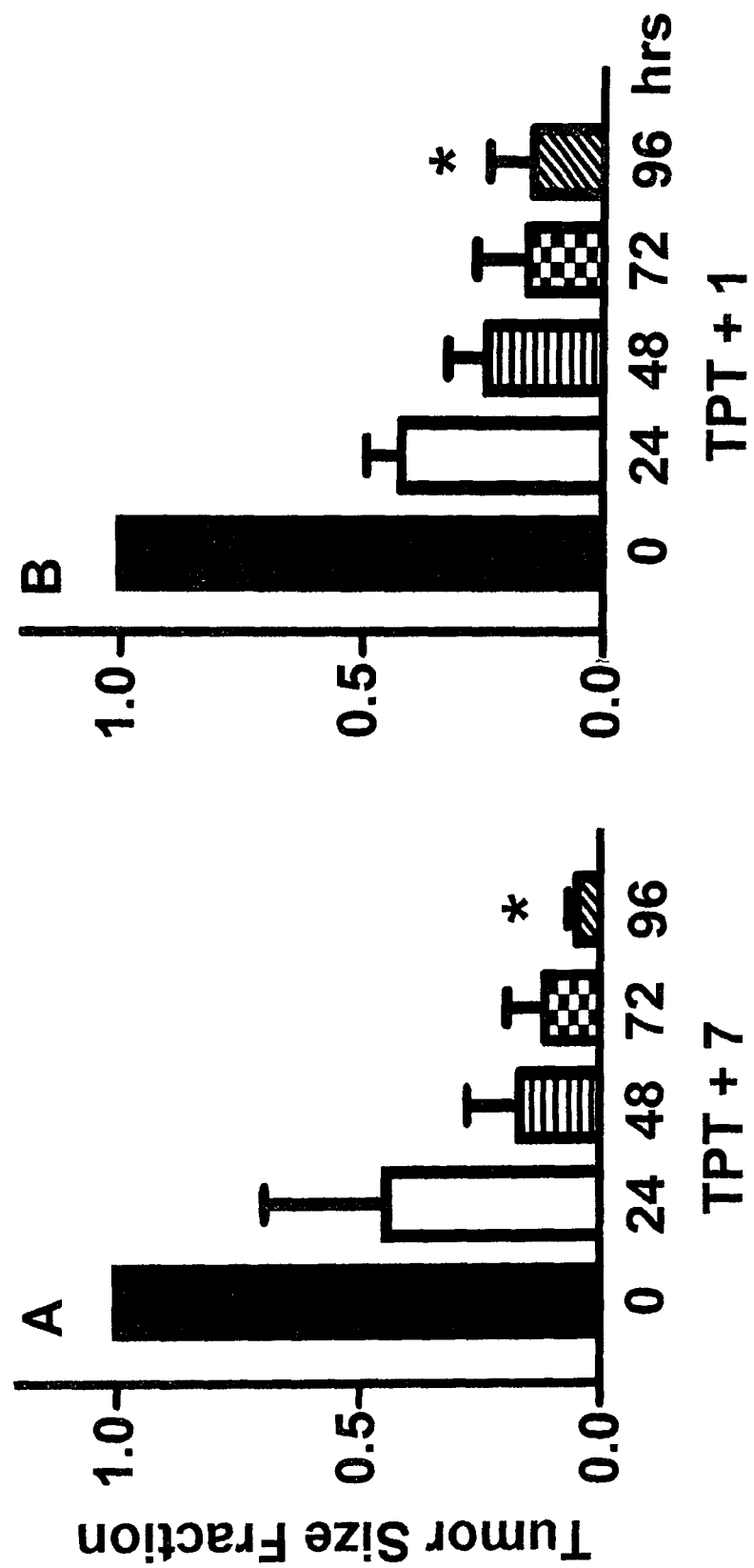
FIG. 29 (Example 2). Response of ABCG2 resistant Igrov1/T8 derived tumors in mice to combination therapy of 150 nM topotecan (TPT). The tumor size at 0, 24, 48, 72, and 96 hr is indicated (n=3) along with the standard error of the mean (SEM). The significant difference between the mean values from 0 to 96 hr is indicated by an asterisk ($p<0.001$). Inhibitor concentration was selected based on potentiation efficacy balanced with apparent cellular toxicity. Significant tumor reduction was noted in both cases. (29A) Compound 7 (original MLSMR hit) at 500 nM in conjunction with TPT. (29B) Probe compound 1 at 100 nM with TPT.
Figure 30:
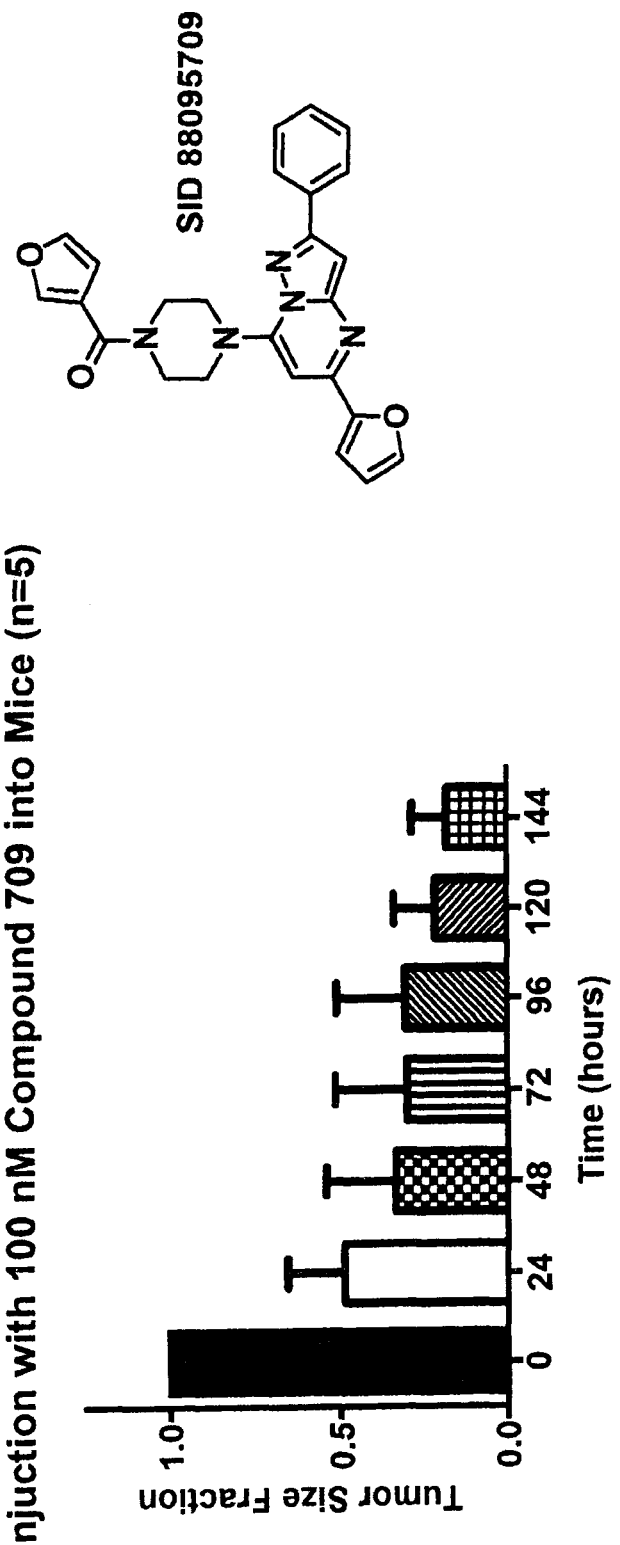
FIG. 30 (Example 3). Time course of injection of 100 nM Topotecan in conjunction with 100 nM compound SAI 88095709 into mice (n=5). Chemotherapeutic (topotecan) resistant Igrov1/TB cells over-expressing ATP binding Cassette G2 (ABCG2) were xenografted subcutaneously into the hind limbs of CB-17/SCID mice. The mice were injected intra-tumorally with 100 nM topotecan in conjunction with 100 nM compound 709 (SID 88095709) every 24 hours. The affect of this combination therapy is shown over a period of 6 days (144 hours). Tumor size was reduced by 80% ($p<0.001$). No reduction in size was observed in tumors treated with either 100 nM topotecan or 100 nM compound 709 alone.
Figure 32:
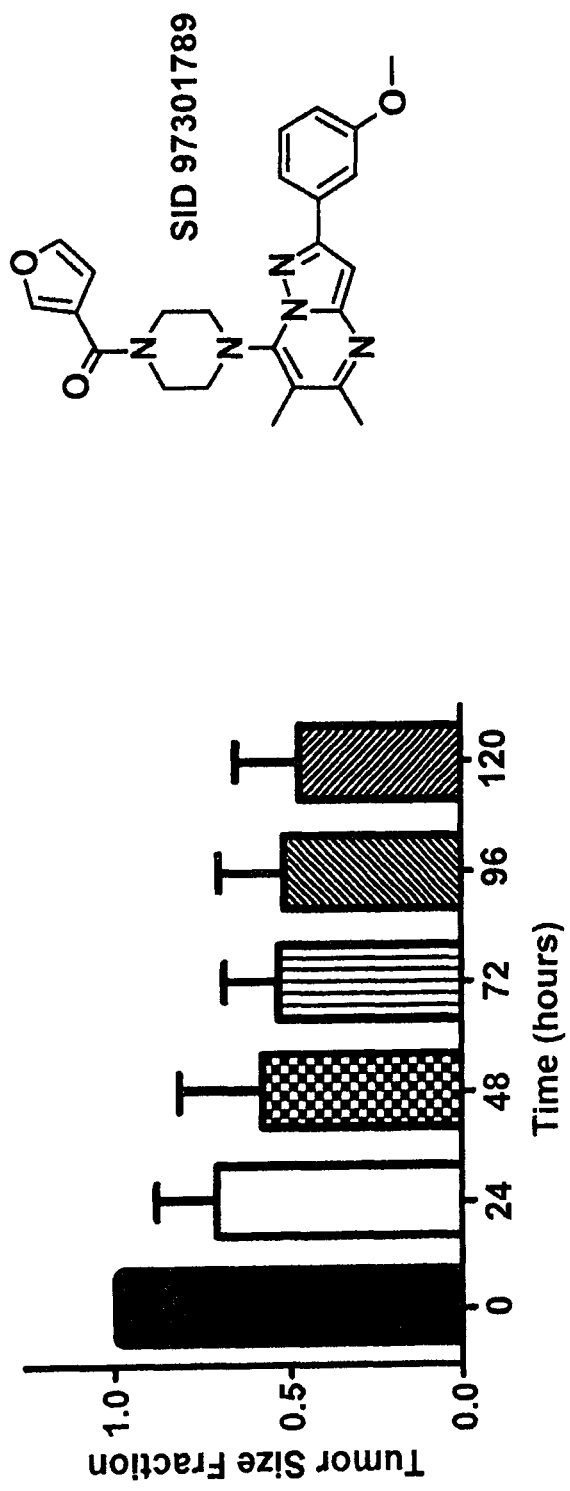
FIG. 32 (Example 3). Time course of injection of 100 nM Topotecan in conjunction with 100 nM compound SAI 97301789 into mice (n=5). Chemotherapeutic (topotecan) resistant Igrov1/T8 cells over-expressing ATP Binding Cassette G2 (ABCG2) were xenografted subcutaneously into the hind limbs of CB-17/SCID mice. The mice were injected intra-tumorally with 100 nM topotecan in conjunction with 100 nM compound 789 (SID 97301789) every 24 hours. The affect of this combination therapy is shown above a period of 5 days (120 hours). Tumor size was reduced by 55% ($p<0.001$). No reduction in size was observed in tumors treated with either 100 nM topotecan or 500 nM compound 789 alone.

FIG. 12 illustrates the clustering. This resulted in effectively three groupings based on the similarity comparisons. SID 88095709 and analogs with aryl and heteroaryl R1 and R2 groups (excluding those with modifications to the piperizine) obviously clustered together and those like SID 97301789 and SID85752814 (and to a lesser extent reversan) with alkyl R2 substituents were grouped together. The third set is included in the remainder of compared structures that did not show significant similarity to one another or the related class scaffolds. In conjunction with the unique chemical space covered, the calculated solubility for the SAR structures appear to be potentially better than those previously described in clinical trials. Interestingly, the calculated solubility of compounds with greater selectivity toward ABCG2 efflux inhibition of JC-1 seem to generally be poorer (more lipophilic) than those for ABCB1 inhibition where greater solubility/hydrophilicity appears to be required. Although the experimental solubility of SID 88095709 is less than ultimately desirable, we are confident that the availability is sufficient for all biological conditions outlined in this report. SID 88095709 also shows good solution stability and appears to not be a kinase inhibitor based on the profile outlined Section 3.6.

The primary screening conditions outlined here are a model system where JC-1 is an efflux inhibition surrogate for chemotherapeutics and it must be noted that there is not necessarily a one to one comparison of substrate recognition by either efflux pump. Previous experimentation from our group has validated the utility of such a model.[56,75] However, this does not exclude the possibility that JC-1 efflux inhibition will not match more phenotypic cell killing assay conditions such as the potentiation assays outlined in this report. Our group has extensively looked at profiling dozens of fluorescent substrates against a panel of known efflux inhibitors in several ABC transporters and observed distinctly different activities dependent on the substrate inhibitor pairing in each over-expression system (unpublished results, manuscript in preparation). This, however, does not diminish the utility of small molecules with specific efflux inhibition profiles. Such inhibitors can be useful tools to look more closely at the nature of such pump poly-specific substrate recognition, ultimately allowing for generation of better model systems.

SID 88095709 demonstrates a 36-fold better efflux inhibition of JC-1 efflux in ABCG2 over ABCB1, thus establishing its usefulness in exploration of the system from a biochemical perspective. This result, coupled with the noted cellular activity in the potentiation assay justifies the overall utility of SID 88095709 as a chemical probe for ABCG2. SID 88095709 showed greater potency and ABCG2 selectivity than any of the aforementioned literature precedent compounds in the efflux inhibition screening conditions. Only XR9051 seems to have better activity in the potentiation assay although with reversed selectivity toward ABCB1. SID 85752814, which was the orignail primary screening hit, does not posses the high level ABCG2 efflux inhibiton selectivity of SID 88095709 but submicromolar potentiation and preliminary tumor reduction data indicate potential clinical opportunities. Interestingly, the structurally-related analogue that has an improved selectivity toward ABCG2 in the efflux assessment, compound SID 97301789, was shown to have significantly more potent cell killing activity in the chemoreversal assay (with no observed toxicity), however, the efflux inhibition selectivity appears to be lost. The emergence of this compound occurred after extensive supporting SAR had been established for SID 88095709, thus limiting the expansion of another arm of SAR in support of SID 97301789; however, this development provides an exciting opportunity for refinement, particularly in the context of the observed ABCG2 tumor reduction preliminary results for SID 88095709 and SID 85752814.

References for Background of the Invention and Example 1

1. Goldman B: Multidrug resistance: can new drugs help chemotherapy score against cancer? *Journal of the National Cancer Institute* 2003; 95:255-7.
2. Krishna R, Mayer L D: Multidrug resistance (MDR) in cancer. Mechanisms, reversal using modulators of MDR and the role of MDR modulators in influencing the pharmacokinetics of anticancer drugs. *European Journal of Pharmaceutical Sciences* 2000; 11:265-283.
3. Mistry P, Plumb J, Eccles S, Watson S, Dale I, Ryder H, Box G, Charlton P, Templeton D, Bevan P B: In vivo efficacy of XR9051, a potent modulator of P-glycoprotein mediated multidrug resistance. *British Journal of Cancer* 1999; 79:1672-1678.
4. Szakacs G, Varadi A, Ozvegy-Laczka C, Sarkadi B: The role of ABC transporters in drug absorption, distribution, metabolism, excretion and toxicity (ADME-Tox). *Drug Discovery Today* 2008; 13:379-393.
5. O'Connor R: The pharmacology of cancer resistance. *Anticancer Research* 2007; 27:1267-1272.
6. Gillet J-P, Efferth T, Remade J: Chemotherapy-induced resistance by ATP-binding cassette transporter genes. *Biochimica et Biophysica Acta* 2007; 1775:237-262.
7. Sarkadi B, Homolya L, Szakacs G, Varadi A: Human multidrug resistance ABCB and ABCG transporters: participation in a chemoimmunity defense system. *Physiological Reviews* 2006; 86:1179-1236.
8. Robey R W, Polgar O, Deeken J, To K W, Bates S E: ABCG2: determining its relevance in clinical drug resistance. *Cancer Metastasis Rev.* 2007; 26:39-57.
9. Garimella T S, Ross D D, Eiseman J L, Mondick J T, Joseph E, Nakanishi T, Bates S E, Bauer K S: Plasma pharmacokinetics and tissue distribution of the breast cancer resistance protein (BCRP/ABCG2) inhibitor fumitremorgin C in SCID mice bearing T8 tumors. *Cancer Chemotherapy and Pharmacology* 2005; 55:101-109.
10. Robey R W, Medina-Perez W Y, Nishiyama K, Lahusen T, Miyake K, Litman T, Senderowicz A M, Ross D D, Bates S E: Overexpression of the ATP-binding cassette half-transporter, ABCG2 (MXR/BCRP/ABCP1), in flavopiridol-resistant human breast cancer cells. *Clinical Cancer Research* 2001; 7:145-152.
11. Allen J D, Van Loevezijn A, Lakhai J M, Van der Valk M, Van Tellingen O, Reid G, Schellens J H M, Koomen G-J, Schinkel A H: Potent and specific inhibition of the breast cancer resistance protein multidrug transporter in vitro and in mouse intestine by a novel analogue of fumitremorgin C. *Molecular Cancer Therapeutics* 2002; 1:417-425.
12. Thiessen B, Stewart C, Tsao M, Kamel-Reid S, Schaiquevich P, Mason W, Easaw J, Belanger K, Forsyth P, McIntosh L and others: A phase I/II trial of GW572016 (lapatinib) in recurrent glioblastoma multiforme: clinical outcomes, pharmacokinetics and molecular correlation. *Cancer Chemother. Pharmacol.* 2010; 65:353-361.
13. Eckford P D W, Sharom F J: ABC Efflux Pump-Based Resistance to Chemotherapy Drugs. *Chemical Reviews* 2009; 109:2989-3011.
14. Kawase M, Motohashi N: New multidrug resistance reversal agents. *Current Drug Targets* 2003; 4:31-43.
15. Avendano C, Menendez J C: Recent advances in multidrug resistance modulators. *Medicinal Chemistry Reviews* 2004; 1:419-444.
16. Broccatelli F, Carosati E, Neri A, Frosini M, Goracci L, Oprea T I, Cruciani G: A Novel Approach for Predicting P-Glycoprotein (ABCB1) Inhibition Using Molecular Interaction Fields. *J. Med. Chem.* 2011; 54:1740-1751.
17. Tsuruo T, Iida H, Tsukagoshi S, Sakurai Y: Overcoming of vincristine resistance in P388 leukemia in vivo and in vitro through enhanced cytotoxicity of vincristine and vinblastine by verapamil. *Cancer Research* 1981; 41:1967-72.
18. Yung B Y M, Chang F J, Bor A M S: Modulation of the reversibility of actinomycin D cytotoxicity in HeLa cells by verapamil. *Cancer Letters* 1991; 60:221-7.
19. Foxwell B M J, Mackie A, Ling V, Ryffel B: Identification of the multidrug resistance-related P-glycoprotein as a cyclosporine binding protein. *Mol. Pharmacol. FIELD Full Journal Title:Molecular Pharmacology* 1989; 36:543-6.
20. Twentyman P R, Fox N E, White D J G: Cyclosporin A and its analogs as modifiers of adriamycin and vincristine resistance in a multi-drug resistant human lung cancer cell line. *British Journal of Cancer* 1987; 56:55-7.
21. Naito M, Yusa K, Tsuruo T: Steroid hormones inhibit binding of Vinca alkaloid to multidrug resistance related P-glycoprotein. *Biochemical and Biophysical Research Communications* 1989; 158:1066-71.
22. Yang C P H, DePinho S G, Greenberger L M, Arceci R J, Horwitz S B: Progesterone interacts with P-glycoprotein in multidrug-resistant cells and in the endometrium of gravid uterus. *Journal of Biological Chemistry* 1989; 264:782-8.
23. Hu Y-P, Chapey C, Robert J: Relationship between the inhibition of azidopine binding to P-glycoprotein by MDR modulators and their efficiency in restoring doxorubicin intracellular accumulation. *Cancer Letters* 1996; 109:203-209.
24. Wang E j, Casciano C N, Clement R P, Johnson W W: Two transport binding sites of P-glycoprotein are unequal yet contingent: initial rate kinetic analysis by ATP hydrolysis demonstrates intersite dependence. *Biochimica et Biophysica Acta, Protein Structure and Molecular Enzymology* 2000; 1481:63-74.
25. Atadja P, Watanabe T, Xu H, Cohen D: PSC-833, a frontier in modulation of P-glycoprotein mediated multidrug resistance. *Cancer and Metastasis Reviews* 1998; 17:163-168.
26. Seiden M V, Swenerton K D, Matulonis U, Campos S, Rose P, Batist G, Ette E, Garg V, Fuller A, Harding M W and others: A Phase II study of the MDR inhibitor bricodar (INCEL, VX-710) and paclitaxel in women with advanced ovarian cancer Refractory to Paclitaxel Therapy. *Gynecologic Oncology* 2002; 86:302-310.
27. Toppmeyer D, Seidman A D, Pollak M, Russell C, Tkaczuk K, Verma S, Overmoyer B, Garg V, Ette E, Harding MW and others: Safety and efficacy of the multidrug resistance inhibitor incel (biricodar; VX-710) in combination with paclitaxel for advanced breast cancer refractory to paclitaxel. *Clinical Cancer Research* 2002; 8:670-678.
28. Germann U A, Shlyakhter D, Mason V S, Zelle R E, Duffy J P, Galullo V, Armistead D M, Saunders J O, Boger J, Harding M W: Cellular and biochemical characterization of VX-710 as a chemosensitizer: reversal of P-glycoprotein-mediated multidrug resistance in vitro. *Anti-Cancer Drugs* 1997; 8:125-140.
29. Dale I L, Tuffley W, Callaghan R, Holmes J A, Martin K, Luscombe M, Mistry P, Ryder H, Stewart A J, Charlton P and others: Reversal of P-glycoprotein-mediated multidrug resistance by XR9051, a novel diketopiperazine derivative. *British Journal of Cancer* 1998; 78:885-892.
30. Stewart A, Steiner J, Mellows G, Laguda B, Norris D, Bevan P: Phase I trial of XR9576 in healthy volunteers demonstrates modulation of P-glycoprotein in CD56+ lymphocytes after oral and intravenous administration. *Clinical Cancer Research* 2000; 6:4186-4191.
31. Agrawal M, Abraham J, Balis F M, Edgerly M, Stein W D, Bates S, Fojo T, Chen C C: Increased 99 mTc-sestamibi accumulation in normal liver and drug-resistant tumors after the administration of the glycoprotein inhibitor, XR9576. *Clinical Cancer Research* 2003; 9:650-656.
32. Mistry P, Stewart A J, Dangerfield W, Okiji S, Liddle C, Bootle D, Plumb J A, Templeton D, Charlton P: In vitro and in vivo reversal of P-glycoprotein-mediated multidrug resistance by a novel potent modulator, XR9576. *Cancer Research* 2001; 61:749-758.
33. Roe M, Folkes A, Ashworth P, Brumwell J, Chima L, Hunjan S, Pretswell I, Dangerfield W, Ryder H, Charlton P: Reversal of P-glycoprotein mediated multidrug resistance by novel anthranilamide derivatives. *Bioorganic & Medicinal Chemistry Letters* 1999; 9:595-600.
34. Jekerle V, Klinkhammer W, Reilly R M, Piquette-Miller M, Wiese M: Novel tetrahydroisoquinolin-ethyl-phenylamine based multidrug resistance inhibitors with broad-spectrum modulating properties. *Cancer Chemotherapy and Pharmacology* 2007; 59:61-69.
35. Jekerle V, Klinkhammer W, Scollard D A, Breitbach K, Reilly R M, Piquette-Miller M, Wiese M: In vitro and in vivo evaluation of WK-X-34, a novel inhibitor of P-glycoprotein and BCRP, using radio imaging techniques. *International Journal of Cancer* 2006; 119:414-422.
36. Hyafil F, Vergely C, Du Vignaud P, Grand-Perret T: In vitro and in vivo reversal of multidrug resistance by GF120918, an acridonecarboxamide derivative. *Cancer Research* 1993; 53:4595-602.
37. Starling J J, Shepard R L, Cao J, Law K L, Norman B H, Kroin J S, Ehlhardt W J, Baughman T M, Winter M A, Bell M G and others: Pharmacological characterization of LY335979: a potent cyclopropyldibenzosuberane modulator of P-glycoprotein. *Advances in Enzyme Regulation* 1997; 37:335-47.
38. Gerrard G, Payne E, Baker R J, Jones D T, Potter M, Prentice H G, Ethell M, McCullough H, Burgess M, Mehta A B and others: Clinical effects and P-glycoprotein inhibition in patients with acute myeloid leukemia treated with zosuquidar trihydrochloride, daunorubicin and cytarabine. *Haematologica* 2004; 89:782-790.
39. Sorbera L A, Castaner J, Silvestre J S, Bayes M: Zosuquidar trihydrochloride: multidrug resistance modulator P-glycoprotein (MDR-1) inhibitor. *Drugs of the Future* 2003; 28:125-136.
40. Naito M, Matsuba Y, Sato S, Hirata H, Tsuruo T: MS-209, a quinoline-type reversal agent, potentiates antitumor efficacy of docetaxel in multidrug-resistant solid tumor xenograft models. *Clinical Cancer Research* 2002; 8:582-8.
41. Saeki T, Nomizu T, Toi M, Ito Y, Noguchi S, Kobayashi T, Asaga T, Minami H, Yamamoto N, Aogi K and others: Dofequidar fumarate (MS-209) in combination with cyclophosphamide, doxorubicin, and fluorouracil for patients with advanced or recurrent breast cancer. *Journal of Clinical Oncology* 2007; 25:411-417.
42. van Zuylen L, Sparreboom A, van der Gaast A, Nooter K, Eskens F A L M, Brouwer E, Bol C J, de Vries R, Palmer P A, Verweij J: Disposition of docetaxel in the presence of P-glycoprotein inhibition by intravenous administration of R101933. *European Journal of Cancer* 2002; 38:1090-1099.
43. Van Zuylen L, Sparreboom A, Van der Gaast A, Van der Burg M E L, Van Beurden V, Bol C J, Woestenborghs R, Palmer P A, Verweij J: The orally administered P-glycoprotein inhibitor R101933 does not alter the plasma pharmacokinetics of docetaxel. *Clinical Cancer Research* 2000; 6:1365-1371.
44. Guns E S, Denyssevych T, Dixon R, Bally M B, Mayer L: Drug interaction studies between paclitaxel (Taxol) and OC144-093—a new modulator of MDR in cancer chemotherapy. *European Journal of Drug Metabolism and Pharmacokinetics* 2002; 27:119-126.
45. Newman M J, Rodarte J C, Benbatoul K D, Romano S J, Zhang C, Krane S, Moran E J, Uyeda R T, Dixon R, Guns E S and others: Discovery and characterization of OC144-093, a novel inhibitor of P-glycoprotein-mediated multidrug resistance. *Cancer Research* 2000; 60:2964-2972.
46. Sarshar S, Zhang C, Moran E J, Krane S, Rodarte J C, Benbatoul K D, Dixon R, Mjalli A M M: 2,4,5-Trisubstituted imidazoles novel nontoxic modulators of P-glycoprotein mediated multidrug resistance. Part 1. *Bioorganic & Medicinal Chemistry Letters* 2000; 10:2599-2601.
47. Zhang C, Sarshar S, Moran E J, Krane S, Rodarte J C, Benbatoul K D, Dixon R, Mjalli A M M: 2,4,5-Trisubstituted imidazoles novel nontoxic modulators of P-glycoprotein mediated multidrug resistance. Part 2. *Bioorganic & Medicinal Chemistry Letters* 2000; 10:2603-2605.
48. Vezmar M, Georges E: Reversal of MRP-mediated doxorubicin resistance with quinoline-based drugs. *Biochemical Pharmacology* 2000; 59:1245-1252.
49. Gollapudi S, Kim C H, Tran B N, Sangha S, Gupta S: Probenecid reverses multidrug resistance in multidrug resistance-associated protein-overexpressing HL60/AR and H69/AR cells but not in P-glycoprotein-overexpressing HL60/Tax and P388/ADR cells. *Cancer Chemotherapy and Pharmacology* 1997; 40:150-158.
50. Stein U, Lage H, Jordan A, Walther W, Bates S E, Litman T, Hohenberger P, Dietel M: Impact of BCRP/MXR, MRP1 and MDR1/P-glycoprotein on thermoresistant variants of atypical and classical multidrug resistant cancer cells. *International Journal of Cancer* 2002; 97:751-760.
51. Rabindran S K, Ross D D, Doyle L A, Yang W, Greenberger L M: Fumitremorgin C reverses multidrug resistance in cells transfected with the breast cancer resistance protein. *Cancer Research* 2000; 60:47-50.
52. Rabindran S K, He H, Singh M, Brown E, Collins K I, Annable T, Greenberger L M: Reversal of a novel multidrug resistance mechanism in human colon carcinoma cells by fumitremorgin C. *Cancer Research* 1998; 58:5850-5858.
53. Liu J, Cui G, Zhao M, Cui C, Ju J, Peng S: Dual-acting agents that possess reversing resistance and anticancer activities: Design, synthesis, MES-SA/Dx5 cell assay, and SAR of Benzyl 1,2,3,5,11,11a-hexahydro-3,3-dimethyl-1-oxo-6H-imidazo[3',':1,2]pyridin[3,4-b]indol-2-substituted acetates. *Bioorganic & Medicinal Chemistry* 2007; 15:7773-7788.
54. Burkhart C A, Watt F, Murray J, Pajic M, Prokvolit A, Xue C, Flemming C, Smith J, Purmal A, Isachenko N and others: Small-Molecule Multidrug Resistance-Associated Protein 1 Inhibitor Reversan Increases the Therapeutic Index of Chemotherapy in Mouse Models of Neuroblastoma. *Cancer Research* 2009; 69:6573-6580.

55. Abe T, Koike K, Ohga T, Kubo T, Wada M, Kohno K, Mori T, Hidaka K, Kuwano M: Chemosensitisation of spontaneous multidrug resistance by a 1,4-dihydropyridine analogue and verapamil in human glioma cell lines overexpressing MRP or MDR1. *British Journal of Cancer* 1995; 72:418-23.

56. Ivnitski-Steele I, Larson R S, Lovato D M, Khawaja H M, Winter S S, Oprea T I, Sklar L A, Edwards B S: High-throughput flow cytometry to detect selective inhibitors of ABCB1, ABCC1, and ABCG2 transporters. *Assay Drug Dev Technol* 2008; 6:263-276.

57. Xia C Q, Milton M N, Gan L-S: Evaluation of drug-transporter interactions using in vitro and in vivo models. *Current Drug Metabolism* 2007; 8:341-363.

58. Sharom F J: The P-glycoprotein efflux pump: how does it transport drugs? *Journal of Membrane Biology* 1997; 160: 161-175.

59. Vellenga E, Tuyt L, Wierenga B-J, Muller M, Dokter W: Interleukin-6 production by activated human monocytic cells is enhanced by MK-571, a specific inhibitor of the multi-drug resistance protein-1. *British Journal of Pharmacology* 1999; 127:441-448.

60. Estes D A, Lovato D M, Khawaja H M, Winter S S, Larson R S: Genetic alterations determine chemotherapy resistance in childhood T-ALL: modelling in stage-specific cell lines and correlation with diagnostic patient samples. *British Journal of Haematology* 2007; 139:20-30.

61. Winter S S, Jiang Z, Khawaja H M, Griffin T, Devidas M, Asselin B L, Larson R S: Identification of genomic classifiers that distinguish induction failure in T-lineage acute lymphoblastic leukemia: a report from the Children's Oncology Group. *Blood* 2007; 110:1429-1438.

62. Kuckuck F W, Edwards B S, Sklar L A: High throughput flow cytometry. *Cytometry* 2001; 44:83-90.

63. Ramirez S, Aiken Charity T, Andrzejewski B, Sklar Larry A, Edwards Bruce S: High-throughput flow cytometry: validation in microvolume bioassays. *Cytometry* 2003; 53:55-65.

64. Solubility and stability data assessment was outsourced to and data was collected by the Sanford-Burnham Center, under the direction of Dr. Layton Smith.

65. Protocol Based on BD Gentest solubility measurements—i.e. Goodwin, J. Poor Aqueous Solubility and Compound Aggregation: Detection, Differences, and Impact on In-Vitro Screens.; Crespi, et al. Aqueous Solubility by Flow Cytometry II: New Prototypes Optimized for Drug Solubility Testing. Poster Presentation: BD Gentest, A BD Biosciences Company, Woburn, Mass. 01801.

66. Data obtained from Luceome Biotechnologies using the KinaseSeeker™ assay. For information on the assay principle and method prt, Jester B W, Cox K J, Gaj A, Shomin C D, Porter J R, Ghosh I: A Coiled-Coil Enabled Split-Luciferase Three-Hybrid System: Applied Toward Profiling Inhibitors of Protein Kinases. *J. Am. Chem. Soc.* 2010; 132:11727-11735.

67. Mayur Y C, Peters G J, Prasad V V S R, Lemos C, Sathish N K: Design of new drug molecules to be used in reversing multidrug resistance in cancer cells. *Current Cancer Drug Targets* 2009; 9:298-306.

68. Seelig A, Gatlik-Landwojtowicz E: Inhibitors of multidrug efflux transporters: their membrane and protein interactions. *Mini-Reviews in Medicinal Chemistry* 2005; 5:135-151.

69. Shapiro A B, Ling V: Positively cooperative sites for drug transport by P-glycoprotein with distinct drug specificities. *European Journal of Biochemistry* 1997; 250:130-137.

70. Lugo M R, Sharom F J: Interaction of LDS-751 and Rhodamine 123 with P-Glycoprotein: Evidence for Simultaneous Binding of Both Drugs. *Biochemistry* 2005; 44:14020-14029.

71. Malkhandi J, Ferry D R, Boer R, Gekeler V, Ise W, Kerr D J: Dexniguldipine-HCl is a potent allosteric inhibitor of [3H]vinblastine binding to P-glycoprotein of CCRF ADR 5000 cells. *European Journal of Pharmacology, Molecular Pharmacology Section* 1994; 288:105-14.

72. Allen J D, Jackson S C, Schinkel A H: A mutation hot spot in the Bcrp1 (Abcg2) multidrug transporter in mouse cell lines selected for doxorubicin resistance. Cancer Research 2002; 62:2294-2299.

73. Mitomo H, Kato R, Ito A, Kasamatsu S, Ikegami Y, Kii I, Kudo A, Kobatake E, Sumino Y, Ishikawa T: A functional study on polymorphism of the ATP-binding cassette transporter ABCG2: critical role of arginine-482 in methotrexate transport. *Biochemical Journal* 2003; 373:767-774.

74. Ozvegy-Laczka C, Koblos G, Sarkadi B, Varadi A: Single amino acid (482) variants of the ABCG2 multidrug transporter: major differences in transport capacity and substrate recognition. *Biochimica et Biophysica acta* 2005; 1668:53-63.

75. Winter S S, Lovato D M, Khawaja H M, Edwards B S, Steele I D, Young S M, Oprea T I, Sklar L A, Larson R S: High-throughput screening for daunorubicin-mediated drug resistance identifies mometasone furoate as a novel ABCB1-reversal agent. *J. Biomol. Screening* 2008; 13:185-193.

Example 2

A Selective ATP-Binding Cassette Sub-Family G Member 2 Efflux Inhibitor Revealed Via High-Throughput Flow Cytometry As a result of a focused SAR-driven chemistry effort we describe compound 1 (CID44640177), an efflux inhibitor with selectivity toward ABCG2 over ABCB1. Compound 1 is also shown to potentiate the activity of mitoxantrone in vitro as well as preliminarily in vivo in an ABCG2 over-expressing tumor model. At least two analogs significantly reduce tumor size in combination with the chemotherapeutic topotecan. To our knowledge, low nanomolar chemoreversal activity coupled with direct evidence of efflux inhibition for ABCG2 is unprecedented.

We set out to develop new small molecule scaffolds with distinct efflux inhibition selectivity profiles based on multiplex transporter target assays. Early in the post-screen follow-up it was evident that ABCG2 was the desirable focus for a probe campaign based on promising preliminary selectivity. Although there has been significant progress with ABCB1 inhibitors, similar progress has not been achieved with ABCG2 inhibitors. An example was noted with the *Aspergillus fumigates* mycotoxin fumitremorgin C (FTC, 3) and its analogs Ko132, Ko134, and Ko143 (4) which have been demonstrated to be selective inhibitors for ABCG2.[17-18] Other reported ABCG2 inhibitors engage non-selectively to include biricodar and nicardipine which are cross-pump inhibitors for ABCB1, ABCC1, and ABCG2.[7,19] Further, specific relevance for ABCG2 as a clinical target has been well documented.[20] This includes a mouse model using a human ovarian xenograft with Igrove1/T8 tumors,[21] a system utilizing flavopiridol-resistant human breast cancer cells,[22] FTC (3) and Ko143 (4) inhibition in vitro and mouse intestine model,[17] and a phase I/II trial with lapatinib in glioblastoma multiforme.[23]

Given the absence of clinically relevant ABCB1 or ABCG2 specific inhibitors and as there remain gaps in understanding how inhibition of these efflux pumps can be best exploited for therapeutic gain, our team focused on vetting and optimizing novel hit scaffolds with promising preliminary ABCG2 or ABCB1 selectivity and potency. As part of that effort, several bench mark compounds were chosen for comparison during development of the pyrazolopyrimidinylpiperazine scaffold, 1. Bench mark compounds were chosen for differential selectivities on ABCB1, ABCC1 and ABCG2, so as to represent a broad panel against which analogs of 1 could be evaluated (FIG. 1A). For direct comparison of selective ABCG2 inhibition, both 3 and 4 were chosen.[17-18] The submicromolar ABCB1 modulator 2 was chosen as it is known to reverse resistance to cytotoxic drugs such as doxorubicin and vincristine.[8,24] Quinoline MK571 (5), a specific inhibitor of ABCC1, was necessary to gauge any ABCC1 activity.[25] Also, reversan (6), identified as an active inhibitor of ABCB1 and ABCC 1, was included as it contained a similar, pyrazolopyrimidine core.[26]

Materials and Methods

General Information

The ABCB1 over-expressing drug-resistant cell line, CCRF-Adr 5000, and its parental CCRF-CEM cells were kindly provided by Dr. T. Efferth (Pharmaceutical Biology, German Cancer Research Center, Heidelberg, Germany). We have previously described the generation of the Jurkat-DNR ABCB1 over-expressing cell line.[27] Ovarian ABCG2 over-expressing Ig-MXP3 and Igrov1/T8 cells as well as the parental Igrov1-sensitive cells were kindly provided by Dr. D. Ross (Department of Medicine, University of Maryland Greenebaum Cancer Center, Baltimore, Md.). Cells were grown in RPMI-1640 medium supplemented with 10% fetal bovine serum (FBS, Hyclone, Logan, Utah), 2 mM L-glutamine, 10 mM HEPES, 10 U $mL^{-1}$ penicillin, 10 µg $mL^{-1}$ streptomycin, and 4 µg $mL^{-1}$ ciprofloxacin. Selective pressure for the ABCB1 over-expressing CCRF-ADR 5000 and Jurkat-DNR cells was maintained by growth in 20 nM daunorubicin hydrochloride (DNR). Selective pressure for the ABCG2 over-expressing Ig-MXP3 cells is maintained by treatment with 340 nM mitoxantrone dihydrochloride (MTX) for 1 hr. prior to harvest.

The fluorescent reporter dye JC-1 and cell type differentiation dye CellTrace™ Far Red DDAO-SE were obtained from Invitrogen™ (Carlsbad, Calif.). Nicardipine hydrochloride, DNR, MTX, topotecan hydrochloride hydrate (TPT) and FTC (3) were purchased from Sigma-Aldrich (St. Louis, Mo.). XR9051 (2), reversan (6), MK571 (5), and Ko143 (4) were purchased from Tocris Bioscience (Minneapolis, Minn.). Compounds ordered for SAR by commerce were purchased from ChemDiv (San Diego, Calif.) and Ryan Scientific (Mt. Pleasant, S.C.). Unless otherwise indicated, all compound solutions were maintained and diluted in DMSO prior to addition to assay wells. Final DMSO concentrations were no more than 1% (v/v). A Biomek® NX Multichannel (Beckman-Coulter, Brea, Calif.) was used for all cell and compound solution transfers for volumes greater than 1 µL. Low volume transfers (100 mL) were done via pintool (V&P Scientific, San Diego, Calif.). Compound dose-response plates were generated with the Biomek® NX Span-8 (Beckman-Coulter, Brea Calif.).

The HyperCyt® high throughput flow cytometry platform (IntelliCyt™, Albuquerque, N. Mex.) was used to sequentially sample cells from 384-well microplates (2 µL per sample) for flow cytometer presentation at a rate of ~40 samples per minute.[28-29] Flow cytometric analysis was performed on a CyAn™ flow cytometer (Beckman-Coulter, Brea, Calif.). The resulting time-gated data files were analyzed with HyperView® software to determine compound activity in each well. Inhibition response curves were fitted by Prism® software (GraphPad Software, Inc., La Jolla, Calif.) using nonlinear least-squares regression in a sigmoidal dose-response model with variable slope, also known as the four-parameter logistic equation. This type of time-gated flow cytometric data analysis was described in detail for a previous ABC transporter screen from our group.[30]

Primary Assay Conditions

To facilitate a shortened screening timeline the single point assay was performed as a duplex allowing for data from both cell lines to be collected in one screening campaign. The assay was conducted in 384-well format microplates in a total volume of 15.1 µL dispensed sequentially as follows: 1) JC-1 substrate (10 µL per well); 2) test compound (100 nL per well); 3) drug-resistant cells (5 µL per well). CCRF-Adr cells (ABCB1) were color-coded with 0.5 ng $mL^{-1}$ CellTrace™ Far Red DDAO-SE for 15 minutes at room temperature, washed twice by centrifugation, and then combined with unlabeled Ig-MXP3 cells (ABCG2) in the assay buffer. Final in-well concentration of test compound was 6.6 µM, JC-1 concentration was ~1 µM. JC-1 previously proved to be an ideal fluorescent reporter substrate for both ABCB1 and ABCG2.[30] The cell concentration was $3\times10^6$ cells $mL^{-1}$ (1:1 ratio of the two cell types). Nicardipine was used as an on-plate control for both pumps at 50 µM. The plate contents were mixed, rotated end-over-end at 4 RPM at 25° C. for 10 minutes, and then cell samples were immediately analyzed. This resulted in analysis of approximately 1,000 cells of each cell type from each well. Flow cytometric data of light scatter and fluorescence emission at 530+/−20 nm (488 nm excitation, FL1) and 665+/−10 nm (633 nm excitation, FL8) were collected.

The CCRF-Adr cell line proved optimal for the duplex-Far Red DDAO-SE staining protocol but in the single-plex follow-up we preferentially used the assay provider's ABCB1 over-expressing Jurkat-DNR cell line for confirmatory dose-response. Each cell line (Jurkat-DNR and Ig-MXP3) was run separately against all compounds (no differential cell staining) in dose-response. The protocol differed from the single point screen as describe here. Cells and reagents were added sequentially as follows: 1) PBS buffer (5 µL per well); 2) test compound (100 nL per well); 3) drug-resistant cells (10 µL, per well) pre-exposed to the JC-1 substrate at 1 µM just prior to the well addition. Final in-well concentrations of test compound ranged from 50 µM to 69 nM over an 18 point dose-response and the cell concentration was $1\times10^6$ cells $mL^{-1}$. Dose response $10_{50}$ values were average for multiple runs (average n of 2 to 4).

Chemoreversal Secondary Assay

Cells (ABCB1, Jurkat-DNR or ABCG2 Ig-MXP3) were incubated with the test compound in a 3 order of magnitude concentration range over three and seven day periods in the presence of the inhibitor and chemotherapeutic (ABCB1, 100 nM DNR or ABCG2 30 nM MTX), such that a cell concentration of at least $1\times10^5$ cells $mL^{-1}$ was maintained. Cell viability was determined by trypan blue staining and enumeration under light microscopy. At day 3, wells with greater than $2\times10^5$ cells were refreshed with medium, to include readjustment of chemotherapeutic and inhibitor concentration. A chemoreversal index (Chemoreversal 50, $CR_{50}$) was determined from the viability assessment. Using a similar approach, a direct cytotoxicity index (Toxic Dose 50, $TD_{50}$)

was determined by assessment of cell death of cells grown in media alone. Results were compared with the survival of parental cells in the presence of the selective agent (chemotherapeutic; 100% cell death), as well as survival of drug-resistant cells in the presence of the chemotherapeutic drug (control yields 100% viability). As previously described by our group for an ABCB1-reversal agent the difference between the $CR_{50}$ and the $TD_{50}$ affords an approximation of the in vitro therapeutic index for the test compound.[31] The threshold for a "good" therapeutic window when comparing $CR_{50}$ and $TD_{50}$ somewhat depends on the endpoint use. For cancer treatment a low threshold, in the 10 fold (or greater) range, can still be considered acceptable due to the severity and life threatening nature of the disease.

Preliminary In Vivo Study

Igrov1/T8 cells were injected into the hind limbs of CB-17 SCID mice at a concentration of $1 \times 10^7$ cells in 200 µL, n of 3 per condition. The tumor was grown until the volume was in the range of 75 mm³ to 250 mm³. The volume of the tumor was verified with a Scienceware® Digi-Max™ slide caliper obtained from Sigma-Aldrich, and the tumor volumes were calculated by the equation: $(W^2/2)*L$.[21] Tumor-bearing mice were injected intratumorally with 150 nM topotecan alone, as well as with either 100 nM of 1 or 500 nM of 7. Injections were repeated daily and the size of the tumor was determined as a fraction of the starting size. After four days the mice were sacrificed and any recurring tumor was verified by light microscopy examination of histological sections. Mice were studied and maintained in accordance with guidelines of our Institutional Animal Research Committee at UNM HSC.

Representative Synthesis

Probe compound 1 and many analogues were synthesized by the method shown (FIG. 2, sequence A-C). Commercial substituted aminopyrazoles 90 ($R_1$=phenyl, substituted phenyl, other substituents found on differenta chemical positions) were treated with the appropriate dialkylmalonate or β-ketoester to give intermediate(s) 91, followed by chlorination to afford the pyrazolo[1,5-a]pyrimidine core intermediate(s) 92. Intermediate(s) 92 is an active compound which allows nucleophilic displacement on the chloro position of a piperazine moiety to provide Installation of the piperazine moiety afforded 1 directly. In some cases, a Suzuki or Molander type coupling was preferred to install aryl functionality at a late stage in the synthesis (FIG. 2A, sequence D-F). More detailed synthetic methods and spectral data can be found in the supplementary material.

Results and Discussion

Primary Screening

A high throughput, no wash, duplex assay was constructed in which both the ABCB1 and ABCG2 transporters were evaluated in parallel using fluorescent JC-1 as the efflux reporting substrate. ABCB1 over-expressing CCRF-Adr cells were color-coded to allow their distinction from Ig-MXP3 ABCG2 over-expressing cells as previously described.[30] FIG. 3A briefly summarizes the primary, duplex screening protocol. The primary screening results were uploaded as PubChem BioAssay Database Identifiers (AID) 1325 and 1326 for ABCG2 and ABCB1 respectively (Summary AID 1818).[32] A total of 194,393 Molecular Libraries Small Molecule Repository (MLSMR, http://mlsmr.glpg.com) compounds were tested with Z' values of 0.74±0.10 and 0.64±0.13 for ABCB1 and ABCG2 respectively. A total of 200 and 130 actives were noted in ABCG2 and ABCB1 respectively. Compounds were deemed active if the percent inhibition was greater than 80%. A subsequent cherry pick resulted in single point confirmatory testing of 273 compounds (AIDs 1453 and 1451) resulting in 16 and 18 actives in ABCG2 and ABCB1, respectively. As a fluorescence counter-screen, a set of related 488/530 nm fluorescence compound profiling data was also associated with the SMR cherry pick set in which compound fluorescence was assessed in the absence of JC-1 to rule out false positives versus actual efflux inhibitors. These data were uploaded as two AIDs (1480 and 1483) where the 273 compounds were tested with 89 and 83 compounds noted as active (i.e. fluorescent) in ABCG2 and ABCB1, respectively. Based on this single point screening data confirmatory dose-response analysis was subsequently performed on 40 compounds (AIDs 1690 and 1689) resulting in 16 actives for ABCB1 and 9 actives for ABCG2.

Efflux Inhibition Driven SAR

No discernable structure activity relationship (SAR) was revealed through the first round of cherry pick analysis or the powder resupply, and many of the compounds were observed to be fluorescent artifacts. However, preliminary chemoreversal secondary screening efforts confirmed activity of several compounds, including 7 (CID 1434724), where micromolar potentiation and low toxicity were observed but with little pump specificity. Secondary potentiation data for compound 7 and fourteen other confirmed compounds were reported in AIDs 2830 and 2833. Resynthesis, purification and retesting of 7 confirmed the efflux inhibition, and a series of compounds similar in structure was ordered around this original hit. These 31 compounds were tested in dose-response in the two efflux pump over-expressing cell lines: Jurkat-DNR (ABCB1) and Ig-MXP3 (ABCG2). A few compounds showed modest ABCG2 selectivity, but gaps in the collection did not resolve the structural functionality responsible for any significant efflux potency or selectivity towards ABCG2 or ABCB1. Due to the diversity of structural changes present in the commercial set, additional compounds were needed to construct meaningful SAR. The commercial powder set contained several members with conserved functionality that provided the basis for establishing a methodical SAR assessment.

The pyrazolo[1,5-a]pyrimidine core was preserved, and exchange of the peripheral substituents were surveyed, depicted as shaded regions (FIG. 4A, panel A). Exploratory commercial SAR expansion resulted in compounds with selectivity profiles significantly biased toward ABCG2. The initial set of hit-related compounds screened from the MLSMR and purchased from vendors predominately possessed structural differences in $R_1$-$R_3$ and the furan ring of $R_4$. Based on these structural variations around the core, we chose functional groups that would fill in the SAR gaps and further reveal pharmacological preferences based on steric interactions, lipophilicity, hydrogen bond donating or accepting character, and modulating the electronic nature of aryl substituents. Of the hits that were identified through this endeavor, 8 (CID1441553) had attractive efflux potency towards ABCG2 and marginal selectivity over ABCB1 (FIG. 5A, panel B). The KU SCC launched an SAR campaign aimed at further understanding the origin of potency and selectivity and set out to optimize the compound profile to meet the MLPCN probe criteria for potency and selectivity in the efflux assay. A suitable probe was defined as a compound that effected micromolar potentiation with a toxic-dose$_{50}$/chemoreversal$_{50}$ ($TD_{50}/CR_{50}$) ratio of greater than 10 and with overall toxicity greater than 15 µM.

Of the approximately 160 compounds assessed in the primary efflux dose-response assay (AIDs 489002, 489003, 504566, and 504569), 126 were synthesized by the KU SCC. Several compounds in the purchased collection contained a 3-chlorophenyl substituent at $R_1$, analogous to the $R_1$ moiety present in hit 8. As such, an initial series of compounds was prepared with this feature maintained while adjusting $R_2$-$R_4$ (Table 1). One compound cluster was constructed with $R_1$-$R_3$ groups (11-25) identical to that of the parent hit 8 while modulating $R_4$. Notably, the substitution of the acyl-2 furan for acyl-3-furan (11) produced a 7-fold enhancement in selectivity for ABCG2, predominately due to erosion of ABCB1 potency, while only modestly attenuating ABCG2 potency as compared to the parent hit. Improved ABCG2 potency was achieved with installation of an acyl-3-pyridine; however, the selectivity deteriorated essentially to pan inhibition (20). Following incorporation of the acyl-3-furan as the more optimal $R_4$ substituent, a survey was then done on the $R_2$ group while holding constant $R_1$ and $R_3$ (26-32). Substantial potency for ABCG2 was gained when $R_4$ was 3-pyridine (30); however, once again, selectivity was negatively impacted.

Alterations in the 3-chlorophenyl $R_1$ substituent were then made while assessing three $R_4$ head groups, specifically alternating between acyl-2-furan, acyl-3-furan, or benzoyl functionalities (33-43). No substantial improvements were noted with these changes; however, when $R_1$ was changed from 3-chlorophenyl to phenyl, and $R_2$ was varied (1, 44-49), it was discovered that a 2-furan at $R_2$ in concert with the optimized acyl-3-furan afforded a significant boost in both ABCG2 potency as well as overall ABCG2 selectivity (1, ABCB1 $EC_{50}$=4.65 µM; ABCG2 $EC_{50}$=0.13 µM, selectivity=36 fold). Representative dose-response curves for 1 are compared (FIG. 5A).

With this information in hand, the team followed up with an SAR effort aimed at demonstrating supportive SAR for compounds bearing an $R_2$=2-furyl group while also attempting to improve upon the profile of the most promising analog, 1 (FIG. 4A, panel C). The modified scaffold, represented by 1, was further studied by adjusting physiochemical and spatial elements in $R_1$ (Supplemental Table S1, compounds 1, 50-60). Replacing the phenyl ring of the lead with a t-butyl group erased much of the gains towards ABCG2 selectivity (50). Traditional phenyl replacements such as thiophene or furan were tolerated, but only led to modest selectivity and potencies. The installation of a 4-chlorophenyl substituent led to a reduced inhibition of ABCB1, resulting in selectivity in the efflux assay of 22-fold (54); however, the change also marginalized the potency on ABCG2. Renovating the phenyl substituent with electron donating groups was not beneficial.

An examination of 2-furan replacements at $R_2$ was also undertaken (Supplemental Table S1, compounds 1, 44-49, 61-66). Simple alkyl units such as methyl or t-butyl degraded potency and fold-selectivity for both transporters. Notably, use of t-butyl actually reversed selectivity for ABCB1, albeit at the expense of potency (49). Some $R_2$ revisions resulted in impressive ABCG2 selectivities and potencies. The choice of 2-F-phenyl (46) slightly degraded potency for ABCB1 as compared to the parent (1), leading to a 10-fold selectivity in favor of ABCG2. For the fluorinated series (46-48), the potency for both transporters decreased as the fluorine atom was migrated from the 2- to 3- to 4-position of the aromatic $R_2$ ring. Interestingly, the use of a 3-MeO-phenyl group impeded potency for ABCB1 activity while retaining submicromolar ABCG2 potency on par with the parent, leading to an improved 83-fold selectivity between the transporters (65). In this series (44, 45, 65), however, a trend was not observed as the substituent was shifted from each position. Additional compounds prepared with the 3-MeO-phenyl group at $R_2$ did not show a consistent SAR (data not shown).

The commercial set of compounds contained a few scaffolds bearing a methyl group at $R_3$. SAR data generated in the early experimental phases demonstrated some benefit to the presence of small alkyl groups at $R_3$; however, this was highly dependent on the identity of groups at $R_1$, $R_2$ and $R_4$. To understand the functionality changes around 1, one analogue was prepared to quickly evaluate the effect of this substitution pattern in concert with our chosen functionalities at $R_1$, $R_2$ and $R_4$). ABCB1 potency was encouragingly impaired, but not without also effecting G2, resulting in a marginal selectivity profile (data not shown).

Attention was then turned to investigating the effect of different $R_4$ functionality appended to the piperazine (Supplemental Table S1, compounds 1, 67-76). In earlier SAR sets, activity was found to be sensitive to the identity of $R_4$ and the pairing of groups at $R_2$ and $R_3$. In the context of our new lead, 1, we wanted to better understand the effect of $R_4$ with the chosen substituents. It was confirmed that an acyl-3-furan was preferred to an acyl-2-furan (67), and simple alkyl substitution of the 3-furan (70-72) or a larger benzofuran (73), while tolerated, did not reveal any benefits. However, the most influential effects on ABCB1 were observed when the acyl furan was exchanged for a benzyl ester (76). While ABCG2 potency was compromised compared to the lead, ABCB1 potency was completely lost, yielding a selectivity of ~19 fold.

In a more aggressive effort, the entire "top piece" of the scaffold, consisting of the piperazine and the $R_4$ group, was modified (Supplemental Table S2, compounds 77-86). Ring-opened piperazine equivalents, truncated amino groups, piperidine amides, ring-expanded amines (not shown) and various structural variations on a theme did not produce a profile superior to that which had already been observed.

In the process of evaluating these structural modifications, several compounds were prepared singly to target possible oversights in SAR, as every possible $R_1$-$R_4$ combination cannot be prepared and assessed in a timely way. Others were targeted as a means of inserting the best combinations as gleaned from the preceding generations of SAR. These compounds were more recently pursued to probe specific structural combinations and are summarized. (Supplemental Table S1, compounds 87-89). Data obtained early in the project had indicated that the acetyl group at $R_4$ was more advantageous than other changes that had been surveyed (including the benzyl ester modification), though later refinement of these data does not now stand out as particular SAR of interest. Based on the information available at the time, substituted phenyl derivatives with varying electronic features at $R_1$ were incorporated with the acetyl $R_4$ group in place (87, 88). No advantages were found.

Prior Art Comparison and Potentiation

In parallel to the above efforts, select compounds were also assessed in secondary assays; however, this chemoreversal assay based on potentiation of a given chemotherapeutic is a very low throughput assay and compound data from this assay could not be used to drive the SAR program. Key data have been collected (AIDs 504476 and 504477) for some of the most promising compounds (Table 2). Evaluation of probe compound 7 showed submicromolar effective potentiated killing of both over-expressing cell lines with preference for ABCG2 from a toxicity perspective, though the degree of selectivity observed in the cell killing assay is removed (1.8 fold in chemoreversal vs. 36-fold in efflux assay). Though clear SAR trends could not be gleaned from the chemoreversal and toxicity data, these experiments provided the basis for evaluating how select compounds would perform in a cellular context. Most of the compounds evaluated in the chemoreversal assay for ABCB1 registered in the 100 to 600 nM range, with only a few outliers. For ABCG2, the $CR_{50}$ was more broad, ranging from ~20 to 1400 nM. These data, coupled with several compounds that showed $TD_{50}$ values >100, provided support for the selection of compounds for preliminary in vivo studies.

Prior art for 1 includes 2 (XR9051) and MK571 which were chosen to verify both ABCB1 activity and counterscreen ABCC1 activity, respectively in our system (Table 2). Compound 2 inhibits the efflux of JC-1 in both ABCB1 and ABCG2 over-expressing cell lines (0.61±0.43 and 2.27±2.05 µM respectively). Potentiation data indicate submicromolar chemoreversal in both Jurkat-DNR and Ig-MXP3 cells with a bias toward ABCB1 at 10 nM as compared to 650 nM for ABCG2. Not surprisingly, we didn't observe any inhibition of ABCB1 or ABCG2 with MK571 (5) up to 50 µM and activity noted in the secondary assays mirrored toxicity indicating no potentiation. Direct comparison of reversan (6) in our efflux inhibition system shows low micromolar inhibition of both ABCB1 and ABCG2 (4.41±2.90 and 0.84±0.03 µM respectively) with moderate selectivity for ABCG2. In our chemoreversal potentiation assay, 6 showed micromolar activity and no ABCG2 selectivity (0.22 and 3.61 µM in ABCB1 and ABCG2, respectively). This was coupled with significant toxicity in the Jurkat-DNR cell line. FTC (3) showed no activity in either cell line in the efflux inhibition assay and was not tested in the potentiation assay. Ko143 (4) has been shown to potentiate mitoxantrone (MTX) at nanomolar levels in ABCG2 over-expressing cells[17]. In our potentiation assay there appeared to be a selectivity for ABCB1 over ABCG2 ($CR_{50}$=0.99 and 5.94 µM respectively) with considerable toxicity in both cell lines. The efflux inhibition activity did not emulate this, showing no activity for ABCB1 and only 13.55 µM inhibition for ABCG2, potentially indicating a binding site difference versus JC-1. Probe compound 1 demonstrates a 36-fold better inhibition of JC-1 efflux for ABCG2 over ABCB1, thus establishing its usefulness for biochemical exploration. This result, coupled with the noted cellular activity in the potentiation assay justifies the overall utility of 1 as a probe for ABCG2. Compound 1 showed greater potency and ABCG2 selectivity than any of the aforementioned literature precedent compounds in the efflux inhibition screening conditions. Only 2 appears to have better activity in the potentiation assay although with reversed selectivity toward ABCB1.

Preliminary In Vivo Mouse Data

To specifically demonstrate the direct effect of a chemotherapeutic agent relevant to these studies, we administered an intratumoral dose of topotecan (TPT, 150 nM). This concentration of TPT was slow to kill non-resistant (ABCG2 non-expressing) parental tumor cells, but not the drug resistant (ABCG2 expressing) tumor cells ($EC_{50}$ for parental is 7 nM vs. 311 nM for resistant cells). To demonstrate efficacy of the inhibitors, we grew ABCG2 resistant tumor cells to a volume between 75 and 250 mm³ in CB-17 SCID mice. Tumor size was determined immediately prior to the first injection. Tumor-bearing mice were injected with 150 nM TPT and either 100 nM of 1 or 500 nM of 7. Such treatment dramatically reduced tumor size the over a 96 hour observatory period (FIG. 6A), indicating that tumor sensitivity of TPT returned when either of the ABCG2-blocking compounds were present (p<0.001). A concentration of 150 nM TPT alone did not affect the growth of tumors (data not shown). Compounds 1 and 7 were chosen as representative molecules from this scaffold, with 7 being the initial hit from the screening campaign and 1 being the efflux inhibition optimized molecule. As previously stated, the low throughput nature of the in vitro chemoreversal secondary assay did not allow for exhaustive testing of all members in the scaffold and thus specific correlation between efflux inhibition and potentiated activity of known chemotherapeutics was not readily accessible. However, similar in vivo activity of 1 and 7 (note there is a five-fold concentration difference for the two, see FIG. 6A) despite dissimilar efflux inhibition profiles indicates that the efflux reporting via JC-1 may not represent activity for both MTX and DNR in Ig-MXP3 and Jurkat-DNR cell lines respectively. This in conjunction with the reported in vitro chemoreversal data in Supplemental Table S1 indicates a need for further analysis of the in vitro to in vivo correlation. A subsequent manuscript detailing activity of molecules from this scaffold in this animal model is forthcoming.

SUMMARY

As a result of a duplex, high-throughput flow cytometric screening campaign and subsequent medicinal chemistry optimization we report herein the discovery of an ABCG2 efflux inhibitor 1 which demonstrates a 36-fold selectivity over ABCB1 toward blocking efflux of the fluorescent substrate JC-1. Furthermore, in the same JC-1 efflux reporter system, 1 maintains approximately 100-fold higher potency in ABCG2 than the prior art Ko143. Subsequent in vitro assays using the known chemotherapeutic mitoxantrone demonstrate the ability of 1 to potentiate cell death of the ABCG2 expressing Ig-MXP3 cells at submicromolar concentration levels. We believe that selective transport inhibitors may allow for more targeted and effective therapy. Preliminary in vivo mouse model data indicate dramatic tumor reduction with co-treatment of TPT with 1. Future studies will focus on several related scaffold members as well as on selectivity profiles in both in vitro and in vivo potentiation.

TABLE 1

(Example 2). SAR expansion on initial hit compound 8 (CID1441553).

| Cpd | CID | $R_1$ | $R_2$ | $R_3$ | $R_4$ | $IC_{50}$ (µM)[a] ABCB1 | ABCG2 | ~Fold G2 Selective[b] |
|---|---|---|---|---|---|---|---|---|
| 8 | CID1441553 | 3-Cl—Ph | Ph | H | CO-2-furyl | 6.18 ± 4.92 | 0.96 ± 0.37 | 6.4 |
| 9 | CID644556 | 3-Cl—Ph | Me | Me | CO-2-furyl | 8.40 ± 0.70 | 2.65 ± 1.07 | 3.2 |
| 10 | CID652994 | 3-Cl—Ph | Me | H | CO-2-furyl | 5.88 ± 1.17 | 2.78 ± 0.82 | 2.1 |
| 11 | CID44640182 | 3-Cl—Ph | Ph | H | CO-3-furyl | 8.58 ± 0.63 | 1.19 ± 0.26 | 7.2 |
| 12 | CID44607976 | 3-Cl—Ph | Ph | H | CO-3-thiophene | 3.97 ± 0.80 | 1.40 ± 0.32 | 2.8 |
| 13 | CID44602407 | 3-Cl—Ph | Ph | H | CO—Ph | 3.42 ± 1.64 | 1.45 ± 0.59 | 2.4 |
| 14 | CID45105078 | 3-Cl—Ph | Ph | H | CO-2-MeO—Ph | 4.73 ± 1.78 | 4.92 ± 4.28 | 1.0 |
| 15 | CID45105074 | 3-Cl—Ph | Ph | H | CO-3-MeO—Ph | 2.64 ± 0.64 | 4.45 ± 4.68 | 0.6 |
| 16 | CID45105073 | 3-Cl—Ph | Ph | H | CO-4-MeO—Ph | 2.89 ± 0.55 | 2.82 ± 1.91 | 1.0 |
| 17 | CID45105075 | 3-Cl—Ph | Ph | H | CO-2-Cl—Ph | 1.85 ± 0.75 | 1.31 ± 0.23 | 1.4 |
| 18 | C1D45105080 | 3-Cl—Ph | Ph | H | CO-3-Cl—Ph | 4.19 ± 1.88 | 2.95 ± 0.57 | 1.4 |
| 19 | CID45105081 | 3-Cl—Ph | Ph | H | CO-4-Cl—Ph | 2.36 ± 0.70 | 2.67 ± 0.85 | 0.9 |
| 20 | CID44623842 | 3-Cl—Ph | Ph | H | CO-3-pyridyl | 0.57 ± 0.08 | 0.23 ± 0.15 | 2.5 |
| 21 | CID44630540 | 3-Cl—Ph | Ph | H | CO-4-pyridyl | 1.16 ± 0.30 | 1.03 ± 0.23 | 1.1 |

TABLE 1-continued (Example 2). SAR expansion on initial hit compound 8 (CID1441553).

|  |  |  |  |  |  | IC$_{50}$ (μM)$^a$ | | ~Fold G2 |
|---|---|---|---|---|---|---|---|---|
| Cpd | CID | R$_1$ | R$_2$ | R$_3$ | R$_4$ | ABCB1 | ABCG2 | Selective$^b$ |
| 22 | CID45281172 | 3-Cl—Ph | Ph | H | CO-cyclohexyl | 3.31 ± 1.86 | 2.67 ± 1.26 | 1.2 |
| 23 | CID44602405 | 3-Cl—Ph | Ph | H | COCH$_3$ | 5.67 ± 2.21 | 6.07 ± 0.73 | 0.9 |
| 24 | CID45105082 | 3-Cl—Ph | Ph | H | CO—Bn | 4.68 ± 2.69 | 5.76 ± 3.40 | 0.8 |
| 25 | CID44607585 | 3-Cl—Ph | Ph | H | SO$_2$Ph | >50 | >50 | NA |
| 26 | CID44631077 | 3-Cl—Ph | 2-F—Ph | H | CO-3-furyl | 4.69 ± 1.50 | 1.93 ± 0.48 | 2.4 |
| 27 | CID44629741 | 3-Cl—Ph | 4-F—Ph | H | CO-3-furyl | 5.65 ± 0.11 | 2.41 ± 0.52 | 2.3 |
| 28 | CID44630538 | 3-Cl—Ph | 3-MeO—Ph | H | CO-3-furyl | 2.17 ± 1.02 | 1.14 ± 0.54 | 1.9 |
| 29 | CID44629740 | 3-Cl—Ph | 4-MeO—Ph | H | CO-3-furyl | 4.12 ± 1.05 | 1.71 ± 0.58 | 2.4 |
| 30 | CID44629742 | 3-Cl—Ph | 3-pyridyl | H | CO-3-furyl | 0.77 ± 0.28 | 0.27 ± 0.12 | 2.9 |
| 31 | CID44630541 | 3-Cl—Ph | 4-pyridyl | H | CO-3-furyl | 3.68 ± 0.35 | 1.46 ± 0.35 | 2.5 |
| 32 | CID44631078 | 3-Cl—Ph | ethynyl | H | CO-3-furyl | 10.16 ± 3.99 | 2.36 ± 0.53 | 4.3 |
| 33 | CID44623844 | 4-Br—Ph | Ph | H | CO-3-furyl | 1.31 ± 0.35 | 0.76 ± 0.43 | 1.7 |
| 34 | CID44640183 | 2-MeO—Ph | Ph | H | CO-3-furyl | 2.17 ± 0.76 | 0.45 ± 0.17 | 4.8 |
| 35 | CID44623840 | 3-MeO—Ph | Ph | H | CO-3-furyl | 2.26 ± 0.83 | 1.14 ± 0.59 | 2.0 |
| 36 | CID44607592 | 4-MeO—Ph | Ph | H | CO-3-furyl | 1.44 ± 0.70 | 1.16 ± 0.66 | 1.2 |
| 37 | CID44640176 | 2-MeO—Ph | Ph | H | CO-2-furyl | 3.00 ± 0.57 | 1.03 ± 0.17 | 2.9 |
| 38 | CID44968166 | 3-MeO—Ph | Ph | H | CO-2-furyl | 4.77 ± 0.63 | 1.40 ± 0.32 | 3.4 |
| 39 | CID492424 | 4-Cl—Ph | Ph | H | CO-2-furyl | 3.64 ± 1.47 | 1.37 ± 0.53 | 2.7 |
| 40 | CID45105079 | 3-Me—Ph | Ph | H | CO-2-furyl | 3.88 ± 1.67 | 2.46 ± 1.09 | 1.6 |
| 41 | CID44640179 | 2-MeO—Ph | Ph | H | CO—Ph | 2.31 ± 0.79 | 0.76 ± 0.06 | 3.0 |
| 42 | CID44968164 | 3-F—Ph | Ph | H | CO—Ph | 4.34 ± 2.09 | 2.27 ± 0.06 | 1.9 |
| 43 | CID44968158 | 4-F—Ph | Ph | H | CO—Ph | 3.99 ± 2.31 | 2.03 ± 0.11 | 2.0 |
| 1 | CID44640177 | Ph | 2-furyl | H | CO-3-furyl | 4.65 ± 0.74 | 0.13 ± 0.03 | 35.8 |
| 44 | CID46905002 | Ph | 2-MeO—Ph | H | CO-3-furyl | 4.52 | 3.66 ± 2.54 | 1.2 |
| 45 | CID46905009 | Ph | 4-MeO—Ph | H | CO-3-furyl | 4.55 | 2.37 ± 1.80 | 1.9 |
| 46 | CID46904993 | Ph | 2-F—Ph | H | CO-3-furyl | 5.61 | 0.56 | 10.0 |
| 47 | CID46905008 | Ph | 3-F—Ph | H | CO-3-furyl | 7.07 | 1.68 ± 0.61 | 4.2 |
| 48 | CID46904994 | Ph | 4-F—Ph | H | CO-3-furyl | 11.82 | 6.45 | 1.8 |

$^a$Efflux inhibition activity (IC$_{50}$) of the JC-1 substrate is reported using Jurkat-DNR cells over-expressing ABCB1 and Ig-MXP3 cells over-expressing ABCG2. Replicates of two to four are reported as averages.
$^b$Selectivity is indicated by the quotient of the average ABCB1 IC$_{50}$ and the average of ABCG2 IC$_{50}$.

TABLE 2

(Example 2). Potentiation data and prior art comparison.

| | | ABCB1 | | | ABCG2 | | |
|---|---|---|---|---|---|---|---|
| Cpd | CID | IC$_{50}^a$ (μM) | CR$_{50}^b$ (μM) | TD$_{50}^c$ (μM) | IC$_{50}^a$ (μM) | CR$_{50}^b$ (μM) | TD$_{50}^c$ (μM) |
| 1 | CID44640177 | 4.65 | 0.55 | 5.52 | 0.13 | 0.31 | 18.30 |
| 8 | CID1441553 | 6.18 | 0.25 | 6.77 | 0.96 | 0.14 | 6.00 |
| 9 | CID644556 | 8.40 | 1.58 | >100 | 2.65 | 0.17 | 47.40 |
| 15 | CID45105074 | 2.64 | 0.35 | >100 | 4.45 | 0.21 | >100 |
| 20 | CID44623842 | 0.57 | 0.17 | 4.72 | 0.23 | 0.13 | 10.30 |
| 21 | CID44630540 | 1.16 | 0.25 | 10.90 | 1.03 | 0.15 | 28.30 |
| 24 | CID45105082 | 4.68 | 0.51 | 17.80 | 5.76 | 0.60 | >100 |
| 30 | CID44629742 | 0.77 | 0.20 | 5.33 | 0.27 | 0.02 | 5.77 |
| 31 | CID44630541 | 3.68 | 0.60 | 13.50 | 1.46 | 0.89 | 57.80 |
| 34 | CID44640183 | 2.17 | 0.45 | 4.37 | 0.45 | 0.49 | 6.50 |
| 36 | CID44607592 | 1.44 | 0.23 | 5.54 | 1.16 | 0.38 | >100 |
| 44 | CID46905002 | 4.52 | 0.17 | 3.73 | 3.66 | 0.68 | 7.62 |
| 52 | CID46905000 | 1.70 | 0.19 | 1.93 | 2.35 | 1.21 | >100 |
| 53 | CID45105077 | 6.42 | 0.53 | 8.53 | 2.55 | 1.38 | 10.80 |
| 56 | CID45281176 | 7.40 | 0.47 | 5.52 | 2.26 | 1.00 | >100 |
| 57 | CID45489721 | 3.45 | 5.77 | >100 | 0.89 | 0.76 | >100 |
| 61 | CID46905005 | 1.60 | 0.42 | 7.33 | 1.40 | 0.76 | 18.30 |
| 65 | CID46904996 | 16.42 | 0.18 | 5.77 | 0.20 | 0.68 | 67.80 |

TABLE 2-continued (Example 2). Potentiation data and prior art comparison.

| Cpd | CID | ABCB1 | | | ABCG2 | | |
| --- | --- | --- | --- | --- | --- | --- | --- |
| | | $IC_{50}{}^a$ (μM) | $CR_{50}{}^b$ (μM) | $TD_{50}{}^c$ (μM) | $IC_{50}{}^a$ (μM) | $CR_{50}{}^b$ (μM) | $TD_{50}{}^c$ (μM) |
| 74 | CID46173053 | 3.64 | 0.19 | 10.10 | 0.52 | 0.93 | >100 |
| 87 | CID46912089 | 0.80 | 0.08 | 17.60 | 0.56 | 0.58 | >100 |
| 88 | CID46912090 | 1.64 | 0.32 | 49.30 | 1.90 | 1.18 | >100 |
| 2 | XR9051 | 0.61 | 0.01 | 1.97 | 2.27 | 0.65 | 21.40 |
| 4 | Ko143 | >50 | 0.99 | 2.84 | 13.55 | 5.94 | 20.00 |
| 5 | MK571 | >50 | 20.40 | 20.40 | >50 | 57.40 | 57.40 |
| 6 | reversan | 4.41 | 0.22 | 7.04 | 0.84 | 3.61 | >100 |

[a] Efflux inhibition activity ($IC_{50}$) of the JC-1 substrate is reported using Jurkat-DNR cells over-expressing ABCB1 and Ig-MXP3 cells over-expressing ABCG2. Replicates of two to four are reported as averages (standard deviation has been removed in this table for clarity).
[b] Chemoreversal$_{50}$ values are calculated as compared to day zero viability across varied dose of inhibitor and constant dose of chemotherapeutic (100 nM DNR for ABCB1 and 30 nM MTX for ABCG2). Each data point was the average of two replicates.
[c] Toxic-dose$_{50}$ values are calculated as compared to day zero viability across varied dose of inhibitor without chemotherapeutic.

Chemicals, Reagents, and General Methods for Synthesis.

$^1$H and $^{13}$C NMR spectra were recorded on a Bruker AM 400 spectrometer (operating at 400 and 101 MHz respectively) or Bruker AM 500 spectrometer (operating at 500 and 125 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 μm column; UV detection wavelength=214 nm; flow rate=0.4 mL min$^{-1}$; gradient=5-100% acetonitrile over 3 min with a hold of 0.8 min at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3H-tetrafluoropropoxy) phosphazine; and a make-up solvent of 90:10:0.1 MeOH:Water:Formic Acid which was introduced to the LC flow prior to the source to assist ionization. The melting point was determined on a Stanford Research Systems OptiMelt apparatus.

5-(furan-2-yl)-2-phenylpyrazolo[1,5-a]pyrimidin-7(4H)-one (91):

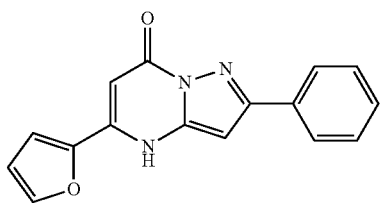

A mixture of 3-phenyl-1H-pyrazol-5-amine (90: 0.318 g, 2.0 mmol, 1.0 eq) and methyl 3-(furan-2-yl)-3-oxopropanoate (0.370 g, 2.2 mmol, 1.10 eq) was heated in acetic acid (2.0 mL) at 100° C. for 4 hr. After cooling down to rt, the precipitate was collected by filtration. The precipitate was rinsed with EtOH (15 mL) and dried under air to afford 5-(furan-2-yl)-2-phenylpyrazolo[1,5-a]pyrimidin-7(4H)-one (0.358 g, 65%) as a white solid. $^1$H-NMR (400 MHz, DMSO-d$_6$) δ 12.70 (s, 1H), 8.06 (m, 1H), 8.00 (m, 1H), 7.98 (m, 1H), 7.51-7.47 (m, 3H), 7.44-7.42 (m, 1H), 6.81 (dd, J=3.7, 1.8 Hz, 1H), 6.64 (s, 1H), 6.15 (s, 1H).

7-chloro-5-(furan-2-yl)-2-phenylpyrazolo[1,5-a]pyrimidine (92):

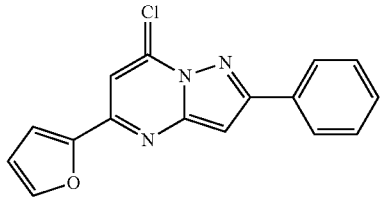

A mixture of 5-(furan-2-yl)-2-phenylpyrazolo[1,5-a]pyrimidin-7(4H)-one (0.277 g, 1.0 mmol, 1.0 eq), POCl$_3$ (0.613 g, 4.0 mmol, 4.0 eq), N-benzyl-N,N,N-triethylethanaminium chloride (0.456 g, 2.0 mmol, 2.0 eq) and N,N-dimethylaniline (0.121 g, 1.0 mmol, 1.0 eq) in acetonitrile (5.0 mL) was heated at 80° C. for 4 hr. The completed reaction was diluted with CHCl$_3$ (20 mL), washed with H$_2$O (10 mL), and the separated organic layers were dried (MgSO$_4$) and concentrated. The residue was purified by chromatography (Biotage25 g, EtOAc/Hexane) to afford 7-chloro-5-(furan-2-yl)-2-phenylpyrazolo[1,5-a]pyrimidine (0.247 g, 84%) as a yellow solid. $^1$H-NMR (400 MHz, CDCl$_3$) δ 7.97-7.94 (m, 2H), 7.56 (m, 1H), 7.43-7.39 (m, 2H), 7.36-7.34 (m, 1H), 7.19 (s, 1H), 7.17 (dd, J=3.5, 0.5 Hz, 1H), 6.97 (s, 1H), 6.54 (dd, J=3.5, 1.7 Hz, 1H).

(4-(5-(furan-2-yl)-2-phenylpyrazolo[1,5-a]pyrimidin-7-yl)piperazin-1-yl)(furan-3-yl)methanone(1):

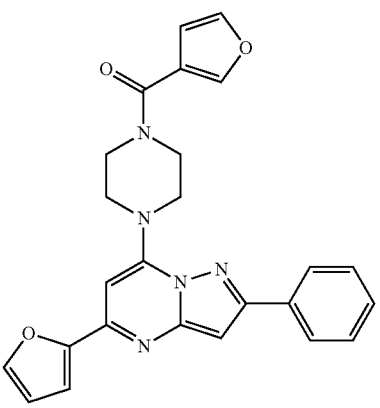

A mixture of 7-chloro-5-(furan-2-yl)-2-phenylpyrazolo[1,5-a]pyrimidine (0.148 g, 0.5 mmol, 1.0 eq), furan-3-yl(piperazin-1-yl)methanone (0.180 g, 1.0 mmol, 2.0 eq,) and N-ethyl-N-isopropylpropan-2-amine (0.129 g, 1.0 mmol, 2.0 eq) in acetonitrile (5.0 mL) was heated at 100° C. for 3 hr. The completed reaction was purified by chromatography (Biotage 25 g, EtOAc/Hexane) to afford (4-(5-(furan-2-yl)-2-phenylpyrazolo[1,5-a]pyrimidin-7-yl)piperazin-1-yl)(furan-3-yl)methanone (0.218 g, 99%) as a white solid. $^1$H-NMR (400 MHz, CDCl$_3$) δ 8.03-8.00 (m, 2H), 7.83 (m, 1H), 7.62 (m, 1H), 7.52-7.47 (m, 3H), 7.45-7.41 (m, 1H), 7.23 (dd, J=3.5, 0.7 Hz, 1H), 6.93 (s, 1H), 6.65 (m, 1H), 6.62 (dd, J=3.5, 1.8 Hz, 1H), 6.60 (s, 1H), 4.08 (b, 4H), 3.92 (b, 4H). $^{13}$C NMR (125 MHz, CDCl$_3$) δ 164.1, 155.4, 152.4, 151.8, 150.1, 148.5, 144.3, 143.8, 143.2, 132.9, 129.0, 128.7, 126.4, 120.6, 112.6, 110.9, 110.1, 92.9, 88.9, 48.3. LCMS retention time: 3.20 min; purity at 215 nm=100%. HRMS m/z calculated for $C_{24}H_{27}N_5O_2$ ([M+H]$^+$): 440.1717. found 440.1715.

TABLE S1

Continuation of SAR expansion, R1-R4 modification.

| Cpd | CID | $R_1$ | $R_2$ | $R_3$ | $R_4$ | IC$_{50}$ (μM)$^a$ ABCB1 | ABCG2 | B1/G2$^a$ | CR$_{50}$ (μM)$^b$ ABCB1 | ABCG2 | TD$_{50}$ (μM)$^c$ ABCB1 | ABCG2 |
|---|---|---|---|---|---|---|---|---|---|---|---|---|
| 1 | CID44640177 | Ph | 2-furyl | H | CO-3-furyl | 4.65 ± 0.74 | 0.13 ± 0.03 | 35.8 | 0.55 | 0.31 | 5.52 | 18.30 |
| 8 | CID1441553 | 3-Cl—Ph | Ph | H | CO-2-furyl | 6.18 ± 4.92 | 0.96 ± 0.37 | 6.4 | 0.25 | 0.14 | 6.77 | 6.00 |
| 9 | CID644556 | 3-Cl—Ph | Me | Me | CO-2-furyl | 8.40 ± 0.70 | 2.65 ± 1.07 | 3.2 | 1.68 | 0.17 | >100 | 47.40 |
| 10 | CID652994 | 3-Cl—Ph | Me | H | CO-2-furyl | 5.88 ± 1.17 | 2.78 ± 0.82 | 2.1 | NT | NT | NT | NT |
| 11 | CID44640182 | 3-Cl—Ph | Ph | H | CO-3-furyl | 8.58 ± 0.63 | 1.19 ± 0.26 | 7.2 | NT | NT | NT | NT |
| 12 | CID44607976 | 3-Cl—Ph | Ph | H | CO-3-thiophenyl | 3.97 ± 0.80 | 1.40 ± 0.32 | 2.8 | NT | NT | NT | NT |
| 13 | CID44602407 | 3-Cl—Ph | Ph | H | CO—Ph | 3.42 ± 1.64 | 1.45 ± 0.59 | 2.4 | NT | NT | NT | NT |
| 14 | CID45105078 | 3-Cl—Ph | Ph | H | CO-2-MeO—Ph | 4.73 ± 1.78 | 4.92 ± 4.28 | 1.0 | NT | NT | NT | NT |
| 15 | CID45105074 | 3-Cl—Ph | Ph | H | CO-3-MeO—Ph | 2.64 ± 0.64 | 4.45 ± 4.58 | 0.6 | 0.35 | 0.21 | >100 | >100 |
| 16 | CID45105073 | 3-Cl—Ph | Ph | H | CO-4-MeO—Ph | 2.89 ± 0.55 | 2.82 ± 1.91 | 1.0 | NT | NT | NT | NT |
| 17 | CID45105075 | 3-Cl—Ph | Ph | H | CO-2-Cl—Ph | 1.85 ± 0.75 | 1.31 ± 0.23 | 1.4 | NT | NT | NT | NT |
| 18 | CID45105080 | 3-Cl—Ph | Ph | H | CO-3-Cl—Ph | 4.19 ± 1.88 | 2.95 ± 0.57 | 1.4 | NT | NT | NT | NT |
| 19 | CID45106081 | 3-Cl—Ph | Ph | H | CO-4-Cl—Ph | 2.36 ± 0.70 | 2.67 ± 0.86 | 0.9 | NT | NT | NT | NT |
| 20 | CID44623842 | 3-Cl—Ph | Ph | H | CO-3-pyridyl | 0.57 ± 0.06 | 0.23 ± 0.15 | 2.5 | 0.17 | 0.13 | 4.72 | 10.30 |
| 21 | CID44630540 | 3-Cl—Ph | Ph | H | CO-4-pyridyl | 1.16 ± 0.30 | 1.03 ± 0.23 | 1.1 | 0.25 | 0.15 | 10.90 | 28.30 |
| 22 | CID45281172 | 3-Cl—Ph | Ph | H | CO-cyclohexyl | 3.31 ± 1.86 | 2.67 ± 1.26 | 1.2 | NT | NT | NT | NT |
| 23 | CID44602405 | 3-Cl—Ph | Ph | H | COCH$_3$ | 5.67 ± 2.21 | 6.07 ± 0.73 | 0.9 | NT | NT | NT | NT |
| 24 | CID45105082 | 3-Cl—Ph | Ph | H | CO—Bn | 4.68 ± 2.69 | 5.76 ± 3.40 | 0.8 | 0.51 | 0.60 | 17.80 | >100 |
| 25 | CID44607585 | 3-Cl—Ph | Ph | H | SO$_2$—Ph | >50 | >50 | NA | NT | NT | NT | NT |
| 26 | CID44631077 | 3-Cl—Ph | 2-F—Ph | H | CO-3-furyl | 4.69 ± 1.50 | 1.93 ± 0.48 | 2.4 | NT | NT | NT | NT |
| 27 | CID44629741 | 3-Cl—Ph | 4-F—Ph | H | CO-3-furyl | 5.65 ± 0.11 | 2.41 ± 0.52 | 2.3 | NT | NT | NT | NT |
| 28 | CID44630538 | 3-Cl—Ph | 3-MeO—Ph | H | CO-3-furyl | 2.17 ± 1.02 | 1.14 ± 0.54 | 1.9 | NT | NT | NT | NT |
| 29 | CID44629740 | 3-Cl—Ph | 4-MeO—Ph | H | CO-3-furyl | 4.12 ± 1.05 | 1.71 ± 0.58 | 2.4 | NT | NT | NT | NT |
| 30 | CID44629742 | 3-Cl—Ph | 3-pyridyl | H | CO-3-furyl | 0.77 ± 0.28 | 0.27 ± 0.12 | 2.9 | 0.20 | 0.02 | 5.33 | 5.77 |
| 31 | CID44630541 | 3-Cl—Ph | 4-pyridyl | H | CO-3-furyl | 3.68 ± 0.35 | 1.46 ± 0.35 | 2.5 | 0.60 | 0.89 | 13.50 | 57.80 |
| 32 | CID44631078 | 3-Cl—Ph | ethynyl | H | CO-3-furyl | 10.16 ± 3.99 | 2.36 ± 0.53 | 4.3 | NT | NT | NT | NT |
| 33 | CID44623844 | 4-Br—Ph | Ph | H | CO-3-furyl | 1.31 ± 0.35 | 0.76 ± 0.43 | 1.7 | NT | NT | NT | NT |
| 34 | CID44640183 | 2-MeO—Ph | Ph | H | CO-3-furyl | 2.17 ± 0.76 | 0.45 ± 0.17 | 4.8 | 0.45 | 0.49 | 4.37 | 6.50 |
| 35 | CID44623840 | 3-MeO—Ph | Ph | H | CO-3-furyl | 2.26 ± 0.83 | 1.14 ± 0.59 | 2.0 | NT | NT | NT | NT |
| 36 | CID44607592 | 4-MeO—Ph | Ph | H | CO-3-furyl | 1.44 ± 0.70 | 1.16 ± 0.66 | 1.2 | 0.23 | 0.38 | 5.54 | >100 |
| 37 | CID44640176 | 2-MeO—Ph | Ph | H | CO-2-furyl | 3.00 ± 0.57 | 1.03 ± 0.17 | 2.9 | NT | NT | NT | NT |
| 38 | CID44958166 | 3-MeO—Ph | Ph | H | CO-2-furyl | 4.77 ± 0.63 | 1.40 ± 0.32 | 3.4 | NT | NT | NT | NT |
| 39 | CID141456 | 4-Cl—Ph | Ph | H | CO-2-furyl | 3.64 ± 1.47 | 1.37 ± 0.63 | 2.7 | NT | NT | NT | NT |
| 40 | CID45105079 | 3-Me—Ph | Ph | H | CO-2-furyl | 3.88 ± 1.67 | 2.46 ± 1.09 | 1.6 | NT | NT | NT | NT |
| 41 | CID44963164 | 2-MeO—Ph | Ph | H | CO—Ph | 2.31 ± 0.79 | 0.76 ± 0.06 | 3.0 | NT | NT | NT | NT |
| 42 | CID44963164 | 3-F—Ph | Ph | H | CO—Ph | 4.34 ± 2.09 | 2.27 ± 0.06 | 1.9 | NT | NT | NT | NT |
| 43 | CID44968158 | 4-F—Ph | Ph | H | CO—Ph | 3.99 ± 2.31 | 2.03 ± 0.11 | 2.0 | NT | NT | NT | NT |
| 44 | CID46905002 | Ph | 2-MeO—Ph | H | CO-3-furyl | 4.62 | 3.66 ± 2.54 | 1.2 | 0.17 | 0.68 | 3.73 | 7.62 |
| 45 | CID46905009 | Ph | 4-MeO—Ph | H | CO-3-furyl | 4.55 | 2.37 ± 1.80 | 1.9 | NT | NT | NT | NT |
| 46 | CID46904008 | Ph | 2-F—Ph | H | CO-3-furyl | 5.61 | 0.56 | 10.0 | NT | NT | NT | NT |
| 47 | CID46906008 | Ph | 3-F—Ph | H | CO-3-furyl | 7.07 | 1.68 ± 0.61 | 4.2 | NT | NT | NT | NT |
| 48 | CID46904994 | Ph | 4-F—Ph | H | CO-3-furyl | 11.82 | 6.45 | 1.8 | NT | NT | NT | NT |
| 49 | CID46905006 | Ph | $^t$Bu | H | CO-3-furyl | 5.62 | 11.50 | 0.5 | NT | NT | NT | NT |

TABLE S1-continued

Continuation of SAR expansion, R1-R4 modification.

$$\text{Structure with } R_1, R_2, R_3, R_4 \text{ substituents on pyrazolopyrimidine-piperazine core}$$

| Cpd | CID | $R_1$ | $R_2$ | $R_3$ | $R_4$ | IC$_{50}$ (μM)[a] ABCB1 | IC$_{50}$ (μM)[a] ABCG2 | B1/G2[d] | CR$_{50}$ (μM)[b] ABCB1 | CR$_{50}$ (μM)[b] ABCG2 | TD$_{50}$ (μM)[c] ABCB1 | TD$_{50}$ (μM)[c] ABCG2 |
|---|---|---|---|---|---|---|---|---|---|---|---|---|
| 50 | CID46912088 | $^t$Bu | 2-furyl | H | CO-3-furyl | 3.31 | 1.97 | 1.7 | NT | NT | NT | NT |
| 51 | CID46905003 | 2-thiopheneyl | 2-furyl | H | CO-3-furyl | 8.42 | 1.56 ± 1.30 | 5.4 | NT | NT | NT | NT |
| 52 | CID46905000 | 2-furyl | 2-furyl | H | CO-3-furyl | 1.70 | 2.35 ± 2.33 | 0.7 | 0.19 | 1.21 | 1.93 | >100 |
| 53 | CID45105077 | 3-Cl—Ph | 2-furyl | H | CO-3-furyl | 6.42 ± 2.87 | 2.55 ± 2.22 | 2.5 | 0.53 | 1.38 | 8.53 | 10.80 |
| 54 | CID46904995 | 4-Cl—Ph | 2-furyl | H | CO-3-furyl | 41.54 | 1.89 ± 1.18 | 22.0 | NT | NT | NT | NT |
| 55 | CID46905004 | 2-MeO—Ph | 2-furyl | H | CO-3-furyl | 5.57 | 2.76 ± 2.14 | 2.0 | NT | NT | NT | NT |
| 56 | CID45281176 | 3-MeO—Ph | | H | CO-3-furyl | 7.40 ± 3.34 | 2.26 ± 1.00 | 3.3 | 0.47 | 1.00 | 5.52 | >100 |
| 57 | CID45489121 | 4-MeO—Ph | 2-furyl | H | CO-3-furyl | 3.45 ± 1.11 | 0.89 ± 0.61 | 3.9 | 5.77 | 0.76 | >100 | >100 |
| 58 | CID46905007 | 3-Me—Ph | 2-furyl | H | CO-3-furyl | 3.45 | 0.58 | 5.9 | NT | NT | NT | NT |
| 59 | CID46904998 | 4-Me—Ph | 2-furyl | H | CO-3-furyl | 11.27 | 5.19 ± 4.22 | 2.2 | NT | NT | NT | NT |
| 60 | CID44640180 | 3-(2-furyl)-Ph | 2-furyl | H | CO-3-furyl | 3.98 ± 1.30 | 0.93 ± 0.27 | 4.3 | NT | NT | NT | NT |
| 61 | CID46905005 | Ph | 3-furyl | H | CO-3-furyl | 1.60 | 1.40 ± 0.27 | 1.1 | 0.42 | 0.76 | 7.33 | 18.30 |
| 62 | CID44602406 | Ph | Ph | H | CO-3-furyl | 4.79 ± 4.23 | 1.58 ± 0.63 | 3.0 | NT | NT | NT | NT |
| 63 | CID44607586 | Ph | Me | H | CO-3-furyl | 15.81 ± 3.33 | 7.27 ± 3.01 | 2.2 | NT | NT | NT | NT |
| 64 | CID46905001 | Ph | 2-thiopheneyl | H | CO-3-furyl | 3.46 | 1.64 ± 0.03 | 2.1 | NT | NT | NT | NT |
| 65 | CID46904996 | Ph | 3-MeO—Ph | H | CO-3-furyl | 16.42 | 0.20 | 82.1 | 0.18 | 0.68 | 5.77 | 67.80 |
| 66 | CID46904999 | Ph | 2-(5-Me-furyl) | H | CO-3-furyl | 0.68 | 0.84 ± 0.87 | 0.8 | NT | NT | NT | NT |
| 67 | CID46173049 | Ph | 2-furyl | H | CO-2-furyl | 6.57 ± 2.13 | 2.77 ± 4.01 | 2.4 | NT | NT | NT | NT |
| 68 | CID46173055 | Ph | 2-furyl | H | CO-3-thiopheneyl | 4.93 ± 1.76 | 1.38 ± 1.04 | 3.6 | NT | NT | NT | NT |
| 69 | CID46173043 | Ph | 2-furyl | H | CO—Ph | 5.56 ± 1.25 | 1.62 ± 1.27 | 3.4 | NT | NT | NT | NT |
| 70 | CID46173050 | Ph | 2-furyl | H | CO-3-(2-Me-furyl) | 11.90 ± 7.40 | 2.33 ± 2.23 | 5.1 | NT | NT | NT | NT |
| 71 | CID46173047 | Ph | 2-furyl | H | CO-3-(2,4-diMe-furyl) | 7.32 ± 2.52 | 3.68 ± 2.21 | 2.0 | NT | NT | NT | NT |
| 72 | CID46173046 | Ph | 2-furyl | H | CO-3-(2,5-diMe-furyl) | 12.00 ± 6.11 | 3.37 ± 1.19 | 3.6 | NT | NT | NT | NT |
| 73 | CID46173052 | Ph | 2-furyl | H | CO-3-benzofuryl | 8.83 ± 6.63 | 2.84 ± 0.96 | 3.1 | NT | NT | NT | NT |
| 74 | CID46173053 | Ph | 2-furyl | H | CO—Me | 3.64 ± 2.55 | 0.52 ± 0.16 | 7.0 | 0.19 | 0.93 | 10.10 | >100 |
| 75 | CID45489722 | Ph | 2-furyl | H | CH$_2$—Ph | 8.99 ± 3.67 | 3.07 ± 1.88 | 2.9 | NT | NT | NT | NT |
| 76 | CID45489719 | Ph | 2-furyl | H | CO$_2$—Bn | >50 | 2.71 ± 1.95 | 18.5 | NT | NT | NT | NT |
| 87 | CID46912089 | 3-Cl—Ph | 2-furyl | H | CO—Me | 0.80 | 0.56 ± 0.09 | 1.4 | 0.08 | 0.58 | 17.60 | >100 |
| 88 | CID46912093 | 3-MeO—Ph | 2-furyl | H | CO—Me | 1.64 | 1.90 ± 1.42 | 0.9 | 0.32 | 1.18 | 49.30 | >100 |
| 89 | CID44629743 | Ph | Me | Me | CO-3-furyl | 1.63 ± 0.59 | 2.18 ± 1.93 | 0.7 | NT | NT | NT | NT |

[a]Efflux inhibition activity (IC$_{50}$) of the JC-1 substrate is reported using Jurkat-DNR cells over-expressing ABCB1 and Ig-MXP3 cells over-expressing ABCG2. Replicates of two to four are reported as averages (standard deviation has been removed in this table for clarity).
[b]Chemoreversal$_{50}$ values are calculated as compared to day zero viability across varied dose of inhibitor and constant dose of chemotherapeutic (100 nM DNR for ABCB1 and 30 nM MIX for ABCG2).
[c]Toxic-dose$_{50}$ values are calculated as compared to day zero viability across varied dose of inhibitor without chemotherapeutic.
[d]Selectivity is indicated by the quotient of the average ABCB1 IC$_{50}$ and the average of ABCG2 IC$_{50}$.

TABLE S2

SAR expansion, modifications to piperazine moiety.

| Cpd | CID | X | IC$_{50}$ (μM)$^a$ ABCB1 | ABCG2 | ~Fold G2 Selective$^b$ |
|---|---|---|---|---|---|
| 1 | CID44640177 | piperazine-N-C(O)-3-furyl | 4.65 ± 0.74 | 0.13 ± 0.03 | 35.8 |
| 77 | CID45489714 | piperazine-NH | 23.56 ± 12.07 | 5.71 ± 1.80 | 4.1 |
| 78 | CID45489720 | -N(Me)CH$_2$CH$_2$N(Me)Me | >50 | 8.88 ± 2.82 | 5.6 |
| 79 | CID45489718 | -N(Me)CH$_2$CH$_2$CH$_2$NH(Me) | 11.92 ± 8.94 | 25.47 ± 13.39 | 0.5 |
| 80 | CID45489715 | -N(Me)CH$_2$CH$_2$N(Me)C(O)-3-furyl | 17.54 ± 5.88 | 13.05 ± 7.88 | 1.3 |
| 81 | CID46173046 | -N(Me)CH$_2$CH$_2$CH$_2$N(Me)C(O)-3-furyl | 13.06 ± 6.27 | 5.43 ± 4.11 | 2.4 |
| 82 | CID45489712 | -N(Me)N(Me)Me | 27.67 ± 14.47 | 7.68 ± 1.69 | 3.6 |
| 83 | CID45489716 | 3-oxo-4-phenylpiperazin-1-yl | 4.06 ± 1.78 | 1.64 ± 0.52 | 2.5 |
| 84 | CID46173044 | 4-(phenylcarbamoyl)piperidin-1-yl | >50 | 8.03 ± 2.18 | 6.2 |

TABLE S2-continued

SAR expansion, modifications to piperazine moiety.

IC$_{50}$ (μM)$^a$

| Cpd | CID | X | ABCB1 | ABCG2 | ~Fold G2 Selective$^b$ |
|---|---|---|---|---|---|
| 85 | CID46173054 | (piperazine with furan-3-carbonyl) | 19.14 ± 9.52 | 2.25 ± 1.90 | 8.5 |
| 86 | CID46245506 | (2-methylpiperazine with furan-3-carbonyl) | 3.27 ± 1.43 | 4.65 ± 3.96 | 0.7 |

$^a$Efflux inhibition activity (IC$_{50}$) of the JC-1 substrate is reported using Jurkat-DNR cells over-expressing ABCB1 and Ig-MXP3 cells over-expressing ABCG2. Replicates of two to four are reported as averages (standard deviation has been removed in this table for clarity).
$^b$Selectivity is indicated by the quotient of the average ABCB1 IC$_{50}$ and the average of ABCG2 IC$_{50}$.

References For Example 2

1. Sarkadi, B., Homolya, L., Szakacs, G., Varadi, A.: Human multidrug resistance ABCB and ABCG transporters: Participation in a chemoimmunity defense system. *Physiol Rev* 2006; 86:1179-1236.
2. Krishna, R., Mayer, L. D.: Multidrug resistance (MDR) in cancer. Mechanisms, reversal using modulators of MDR and the role of MDR modulators in influencing the pharmacokinetics of anticancer drugs. *Eur J Pharm Sci* 2000; 11:265-283.
3. Gillet, J.-P., Efferth, T., Remade, J.: Chemotherapy-induced resistance by ATP-binding cassette transporter genes. *Biochim Biophys Acta* 2007; 1775:237-262.
4. Szakacs, G., Varadi, A., Ozvegy-Laczka, C., Sarkadi, B.: The role of ABC transporters in drug absorption, distribution, metabolism, excretion and toxicity (ADME-Tox). *Drug Discov Today* 2008; 13:379-393.
5. Eckford, P. D. W., Sharom, F. J.: ABC efflux pump-based resistance to chemotherapy drugs. *Chem Rev* 2009; 109: 2989-3011.
6. Atadja, P., Watanabe, T., Xu, H., Cohen, D.: PSC-833, a frontier in modulation of P-glycoprotein mediated multidrug resistance. *Cancer Metastasis Rev* 1998; 17:163-168.
7. Germann, U. A., Shlyakhter, D., Mason, V. S., Zelle, R. E., Duffy, J. P., Galullo, V., et al.: Cellular and biochemical characterization of VX-710 as a chemosensitizer: Reversal of P-glycoprotein-mediated multidrug resistance in vitro. *Anti-Cancer Drugs* 1997; 8:125-140.
8. Dale, I. L., Tuffley, W., Callaghan, R., Holmes, J. A., Martin, K., Luscombe, M., et al.: Reversal of P-glycoprotein-mediated multidrug resistance by XR9051, a novel diketopiperazine derivative. *Br J Cancer* 1998; 78:885-892.
9. Mistry, P., Stewart, A. J., Dangerfield, W., Okiji, S., Liddle, C., Bootle, D., et al.: In vitro and in vivo reversal of P-glycoprotein-mediated multidrug resistance by a novel potent modulator, XR9576. *Cancer Res* 2001; 61:749-758.
10. Stewart, A., Steiner, J., Mellows, G., Laguda, B., Norris, D., Bevan, P.: Phase I trial of XR9576 in healthy volunteers demonstrates modulation of P-glycoprotein in CD56+ lymphocytes after oral and intravenous administration. *Clin Cancer Res* 2000; 6:4186-4191.
11. Jekerle, V., Klinkhammer, W., Scollard, D. A., Breitbach, K., Reilly, R. M., Piquette-Miller, M., et al.: In vitro and in vivo evaluation of WK-X-34, a novel inhibitor of P-glycoprotein and BCRP, using radio imaging techniques. *Int J Cancer* 2006; 119:414-422.
12. Hyafil, F., Vergely, C., Du Vignaud, P., Grand-Perret, T.: In vitro and in vivo reversal of multidrug resistance by GF 120918, an acridonecarboxamide derivative. *Cancer Res* 1993; 53:4595-4602.
13. Gerrard, G., Payne, E., Baker, R. J., Jones, D. T., Potter, M., Prentice, H. G., et al.: Clinical effects and P-glycoprotein inhibition in patients with acute myeloid leukemia treated with zosuquidar trihydrochloride, daunorubicin and cytarabine. *Haematologica* 2004; 89:782-790.
14. Saeki, T., Nomizu, T., Toi, M., Ito, Y., Noguchi, S., Kobayashi, T., et al.: Dofequidar fumarate (MS-209) in combination with cyclophosphamide, doxorubicin, and fluorouracil for patients with advanced or recurrent breast cancer. *J Clin Oncol* 2007; 25:411-417.
15. van Zuylen, L., Sparreboom, A., van der Gaast, A., Nooter, K., Eskens, F. A. L. M., Brouwer, E., et al.: Disposition of docetaxel in the presence of P-glycoprotein inhibition by intravenous administration of R101933. *Eur J Cancer* 2002; 38:1090-1099.

16. Guns, E. S., Denyssevych, T., Dixon, R., Bally, M. B., Mayer, L.: Drug interaction studies between paclitaxel (Taxol) and OC144-093—A new modulator of MDR in cancer chemotherapy. *Eur J Drug Metab Pharmacokinet* 2002; 27:119-126.
17. Allen, J. D., Van Loevezijn, A., Lakhai, J. M., Van der Valk, M., Van Tellingen, 0., Reid, G., et al.: Potent and specific inhibition of the breast cancer resistance protein multidrug transporter in vitro and in mouse intestine by a novel analogue of fumitremorgin C. *Mol Cancer Ther* 2002; 1:417-425.
18. Rabindran, S. K., Ross, D. D., Doyle, L. A., Yang, W., Greenberger, L. M.: Fumitremorgin C reverses multidrug resistance in cells transfected with the breast cancer resistance protein. *Cancer Res* 2000; 60:47-50.
19. Abe, T., Koike, K., Ohga, T., Kubo, T., Wada, M., Kohno, K., et al.: Chemosensitisation of spontaneous multidrug resistance by a 1,4-dihydropyridine analogue and verapamil in human glioma cell lines overexpressing MRP or MDR1. *Br J Cancer* 1995; 72:418-423.
20. Robey, R. W., Polgar, O., Deeken, J., To, K. W., Bates, S. E.: ABCG2: Determining its relevance in clinical drug resistance. *Cancer Metastasis Rev* 2007; 26:39-57.
21. Garimella, T. S., Ross, D. D., Eiseman, J. L., Mondick, J. T., Joseph, E., Nakanishi, T., et al.: Plasma pharmacokinetics and tissue distribution of the breast cancer resistance protein (BCRP/ABCG2) inhibitor fumitremorgin C in SCID mice bearing T8 tumors. *Cancer Chemother Pharmacol* 2005; 55:101-109.
22. Robey, R. W., Medina-Perez, W. Y., Nishiyama, K., Lahusen, T., Miyake, K., Litman, T., et al.: Overexpression of the ATP-binding cassette half-transporter, ABCG2 (MXR/BCRP/ABCP1), in flavopiridol-resistant human breast cancer cells. *Clin Cancer Res* 2001; 7:145-152.
23. Thiessen, B., Stewart, C., Tsao, M., Kamel-Reid, S., Schaiquevich, P., Mason, W., et al.: A phase I/II trial of GW572016 (lapatinib) in recurrent glioblastoma multiforme: Clinical outcomes, pharmacokinetics and molecular correlation. *Cancer Chemother Pharmacol* 2010; 65:353-361.
24. Mistry, P., Plumb, J., Eccles, S., Watson, S., Dale, I., Ryder, H., et al.: In vivo efficacy of XR9051, a potent modulator of P-glycoprotein mediated multidrug resistance. *Br J Cancer* 1999; 79:1672-1678.
25. Vellenga, E., Tuyt, L., Wierenga, B.-J., Muller, M., Dokter, W.: Interleukin-6 production by activated human monocytic cells is enhanced by MK-571, a specific inhibitor of the multi-drug resistance protein-1. *Br J Pharmacol* 1999; 127:441-448.
26. Burkhart, C. A., Watt, F., Murray, J., Pajic, M., Prokvolit, A., Xue, C., et al.: Small-molecule multidrug resistance-associated protein 1 inhibitor reversan increases the therapeutic index of chemotherapy in mouse models of neuroblastoma. *Cancer Res* 2009; 69:6573-6580.
27. Estes, D. A., Lovato, D. M., Khawaja, H. M., Winter, S. S., Larson, R. S.: Genetic alterations determine chemotherapy resistance in childhood T-ALL: modelling in stage-specific cell lines and correlation with diagnostic patient samples. *Br J Haematol* 2007; 139:20-30.
28. Kuckuck, F. W., Edwards, B. S., Sklar, L. A.: High throughput flow cytometry. *Cytometry* 2001; 44:83-90.
29. Ramirez, S., Aiken Charity, T., Andrzejewski, B., Sklar Larry, A., Edwards Bruce, S.: High-throughput flow cytometry: validation in microvolume bioassays. *Cytometry* 2003; 53:55-65.
30. Ivnitski-Steele, I., Larson, R. S., Lovato, D. M., Khawaja, H. M., Winter, S. S., Oprea, T. I., et al.: High-throughput flow cytometry to detect selective inhibitors of ABCB1, ABCC1, and ABCG2 transporters. *Assay Drug Dev Technol* 2008; 6:263-276.
31. Winter, S. S., Lovato, D. M., Khawaja, H. M., Edwards, B. S., Steele, I. D., Young, S. M., et al.: High-throughput screening for daunorubicin-mediated drug resistance identifies mometasone furoate as a novel ABCB1-reversal agent. *J Biomol Screen* 2008; 13:185-193.
32. National Center for Biotechnology Information. PubChem BioAssay Database; AID-4818, Source=University of New Mexico Center for Molecular Discovery, http://pubchem.ncbi.nlm.nih.gov/assay/assay.cgi?aid=1818&loc=ea_ras.

Example 3

Combination Therapies

FIG. 1B depicts the time course of injection of 100 nM Topotecan in conjunction with 100 nM compound 709 (SID 88095709) into mice (n=5). Experimental conditions were as described in the figure legend. The effect of this combination therapy is shown in FIG. 1B over a period of six days (144 hours). Tumor size was reduced by 89% (p less than 0.001). No reduction in size was observed in tumors treated with either 100 nM Topotecan or 100 nM compound 709 alone.

FIG. 2B depicts the time course of injection of 100 nM Topotecan in conjunction with 500 nM compound 37 (SID 85752814) into mice (n=5). Experimental conditions were as described in the figure legend. The effect of this combination therapy is shown in FIG. 2B over a period of five days (120 hours). Tumor size was reduced by 81% (p less than 0.001). No reduction in size was observed in tumors treated with either 100 nM Topotecan or 100 nM compound 37 alone.

FIG. 3B depicts the time course of injection of 100 nM Topotecan in conjunction with 100 nM compound 789 (SID 97301789) into mice (n=5). Experimental conditions were as described in the figure legend. The effect of this combination therapy is shown in FIG. 3B over a period of five days (120 hours). Tumor size was reduced by 55% (p less than 0.001). No reduction in size was observed in tumors treated with either 100 nM Topotecan or 100 nM compound 789 alone.

The invention claimed is:

1. A pharmaceutical composition comprising an effective amount of a compound according to the chemical structure:

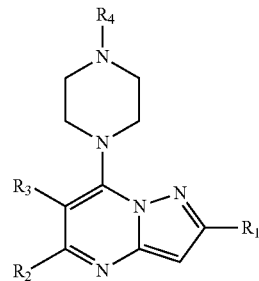

Where $R_1$ is an optionally substituted aryl group;
$R_2$ is an optionally substituted alkyl, aryl or heteroaryl group;
$R_3$ is H or an optionally substituted $C_1$-$C_6$ alkyl group; and
$R_4$ is an optionally substituted heteroarylalkyl or heteroaryl group wherein said heteroarylalkyl group is attached to the amine group of the piperazine moiety through a $CH_2$ group and said heteroaryl group is attached to the amine group of the piperazine moiety through an acyl group;
or an enantiomer, diastereomer, tautomer, or pharmaceutically-acceptable salt,
in combination with one or more pharmaceutically-acceptable excipients, optionally in combination with at least one additional anticancer agent.

2. The composition of claim 1 wherein $R_4$ is an optionally substituted heteroaryl group attached to the amine group of the piperazine moiety through an acyl group, or a pharmaceutically acceptable salt thereof.

3. The composition of claim 1 wherein $R_2$ is an optionally substituted $C_1$-$C_3$ alkyl or an optionally substituted heteroaryl, $R_3$ is hydrogen, $R_4$ is an optionally substituted 5 or 6-membered heteroaryl group which is attached to the amine group of the piperazine moiety through an acyl group, or a pharmaceutically acceptable salt thereof.

4. The composition of claim 1 wherein $R_2$ is an optionally substituted furan, $R_3$ is hydrogen, and $R_4$ is a substituted or unsubstituted furan which is attached to the amine group of the piperazine moiety through an acyl or a $CH_2$ group, or a pharmaceutically acceptable salt thereof.

5. The composition of claim 1 wherein the compound is:

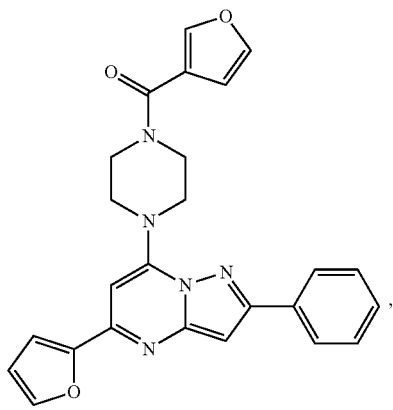

SID 88095709 or a pharmaceutically acceptable salt thereof.

6. The composition according to claim 1 wherein the compound is:

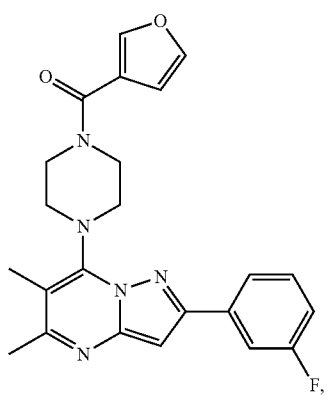

SID 85752814 or a pharmaceutically acceptable salt thereof.

7. The composition of claim 1 wherein the compound is:

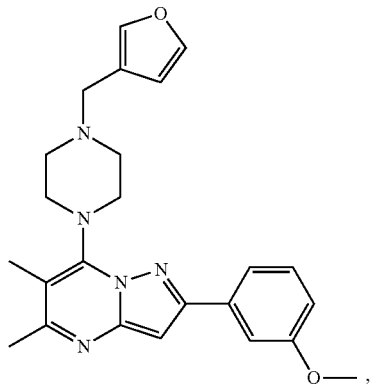

SID 97301789 or a pharmaceutically acceptable salt thereof.

8. The composition of claim 1, wherein $R_1$ and $R_2$ are substituted or unsubstituted phenyl, $R_3$ is hydrogen and $R_4$ is CO-3-pyridyl,
or a pharmaceutically acceptable salt thereof.

9. The composition of claim 1, wherein $R_1$ is 3-Cl-phenyl, $R_2$ is phenyl, $R_3$ is hydrogen and $R_4$ is CO-3-pyridyl,
or a pharmaceutically acceptable salt thereof.

10. The composition according to claim 1, wherein $R_1$ is phenyl, $R_2$ is 3-2-F-phenyl, $R_3$ is hydrogen and $R_4$ is CO-3-furyl,
or a pharmaceutically acceptable salt thereof.

11. The composition of claim 1, wherein $R_1$ is 3-Cl-phenyl, $R_2$ is 3-pyridyl, $R_3$ is hydrogen and $R_4$ is CO-3-furyl,
or a pharmaceutically acceptable salt thereof.

12. The composition of claim 1, wherein $R_1$ is phenyl, $R_2$ is 3-MeO-phenyl, $R_3$ is hydrogen and $R_4$ is CO-3-furyl,
or a pharmaceutically acceptable salt thereof.

13. The composition according to claim 1, wherein $R_1$ is an optionally substituted phenyl; $R_2$ is lower alkyl, optionally substituted phenyl or an optionally substituted five-membered heteroaryl containing one or two ring heteroatoms selected from the group consisting of O and N; $R_3$ is hydrogen or lower alkyl; and $R_4$ is a five-membered, optionally substituted heteroaryl containing one or two ring heteroatoms selected from the group consisting of O and N, wherein said heteroaryl group is attached to the amine group of the piperazine moiety through an acyl group, or a pharmaceutically acceptable salt thereof.

14. The composition according to claim 1, wherein $R_1$ is phenyl which is optionally substituted by halogen or lower alkoxy; $R_2$ is phenyl which is optionally by halogen or lower alkoxy, or $R_2$ is furyl; $R_3$ is hydrogen; and $R_4$ is furanoyl, or a pharmaceutically acceptable salt thereof.

15. The composition of claim 1, wherein $R_1$ is phenyl which is optionally substituted by Cl, F or methoxy; $R_2$ is phenyl which is optionally substituted by Cl, F or methoxy, or $R_2$ is furyl; $R_3$ is hydrogen; and $R_4$ is furanoyl, or a pharmaceutically acceptable salt thereof.

16. The pharmaceutical composition of claim 1 wherein $R_4$ is an optionally substituted heteroarylalkyl group wherein said heteroarylalkyl group is attached to the amine group of the piperazine moiety through a $CH_2$ group, or a pharmaceutically acceptable salt thereof.

* * * * *